(12) United States Patent
Neidle et al.

(10) Patent No.: US 7,300,930 B2
(45) Date of Patent: Nov. 27, 2007

(54) THERAPEUTIC ACRIDONE AND ACRIDINE COMPOUNDS

(75) Inventors: Stephen Neidle, Hertfordshire (GB); Richard John Harrison, Berkshire (GB); Lloyd Royston Kelland, Surrey (GB); Sharon Michele Gowan, Surrey (GB); Martin Anthony Read, Minster (GB); Anthony Reszka, London (GB)

(73) Assignee: Cancer Research Technology Limited, London (GB)

(*) Notice: Subject to any disclaimer, the term of this patent is extended or adjusted under 35 U.S.C. 154(b) by 209 days.

(21) Appl. No.: 11/157,977

(22) Filed: Jun. 22, 2005

(65) Prior Publication Data

US 2006/0111389 A1 May 25, 2006

Related U.S. Application Data

(62) Division of application No. 10/332,261, filed as application No. PCT/GB01/03046 on Jul. 6, 2001.

(60) Provisional application No. 60/216,624, filed on Jul. 7, 2000.

(51) Int. Cl.
*A61K 31/5377* (2006.01)
*A61K 31/435* (2006.01)
*C07D 413/14* (2006.01)
*C07D 219/10* (2006.01)

(52) U.S. Cl. .................. 514/232.5; 544/106; 544/126; 544/224; 544/336; 546/102; 546/104; 546/105; 514/231.2; 514/252.11; 514/290; 514/297

(58) Field of Classification Search ................ 544/106, 544/111, 124, 126, 224, 336; 546/102, 104, 546/105; 514/231.2, 231.5, 232.5, 252.11, 514/290, 297
See application file for complete search history.

(56) References Cited

U.S. PATENT DOCUMENTS 7,160,896 B2 * 1/2007 Neidle et al. ................ 514/297
7,205,311 B2 * 4/2007 Neidle et al. ................ 514/297

FOREIGN PATENT DOCUMENTS

DE 488 890 12/1929

OTHER PUBLICATIONS

Autexier, C., 1999, "Telomerase as a Possible Target for Anticancer Therapy," *Chemistry & Biology*, Nov. 1999, vol. 6, pp. R299-R303.
Bogert, M.T., et al., 1930, "Researches in the Acridine Series. The Synthesis of Isomers of Proflavine and of Neutral Acriflavine," *Collect. Czech. Chem. Comm.*, vol. 2, pp. 383-395.
Bostock-Smith, C.E., et al., 1999, "Molecular Recognition between a New Pentacyclic Acridinium Salt and DNA Sequences Investigated by Optical Spectroscopic Techniques, Proton Nuclear Magnetic Resonance Spectroscopy, and Molecular Modeling," *Biochemistry*, vol. 38, No. 21, pp. 6723-6731.
Cain, B.F., et al., 1974, "Potential Antitumor Agents. 14. Acridylmethanesulfonanilides," *J. Med. Chem.*, vol. 17, No. 9, pp. 922-930.
Cain, B.F., et al., 1976, "Potential Antitumor Agents. 17. 9-Anilino-10-methylacridinium salts," *J. Med. Chem.*, vol. 19, No. 6, pp. 772-777.
Cain, B.F., et al., 1976, "Potential Antitumor Agents. 19. Multiply Substituted 4'-(9-Acridinylamino)methanesulfonanilides," *J. Med. Chem.*, vol. 19, No. 9, pp. 1124-1129.
Denny, W.A., et al., 1982, "Potential Antitumour Agents. 36. Quantitative Relationships between Experimental Antitumour Activity, Toxicity, and Structure for the General Class of 9-Anilinoacridine Antitumor Agents," *J. Med. Chem.*, vol. 25, pp. 276-315.
Gamage, S.A., et al., 1994, "Synthesis and in Vitro Evaluation of 9-Anilino-3,6-diaminoacridines Active Against a Multidrug Resistant Strain of the Malaria Parasite *Plasmodium falciparum*," *J. Med. Chem.*, vol. 37, No. 10, pp. 1486-1494.
Gimenez-Arnau, E. et al., 1998, "Antitumour Polycyclic Acridines, Part 2," *Anti-Cancer Drug Design*, vol. 13, pp. 125-143.
Gimenez-Arnau, E., et al., 1998, "Antitumour Polycyclic Acridines, Part 4," *Anti-Cancer Drug Design*, vol. 13, pp. 431-451.
Goldberg, A.A. and Kelly, W., 1946, "29. Synthesis of Diaminoacridines. Part 1," *J. Chem. Soc.*, p. 102-111.
Goldstein, H., and de Simo, M., 1927, "Quelques derives de l'acide phenyl-anthranilique III," *Helv. Chim. Acta.*, vol. 10, p. 603-606.
Hagan, D.H., et al., 1997, "Antitumour Polycyclic Acridines, Part 1," *J. Chem. Soc., Perkin Trans. 1*, pp. 2739-2746.

(Continued)

Primary Examiner—Golam M. M. Shameem
(74) Attorney, Agent, or Firm—Nixon & Vanderhye P.C.

(57) ABSTRACT

The present invention pertains to acridone and acridine compounds of formula (I), wherein either: (a) K is =O, L is —H, alpha is a single bond, beta is a double bond, gamma is a single bond (acridones); or, (b) K is a 9-substituent, L is absent, alpha is a double bond, beta is a single bond, gamma is a double bond (acridines); and wherein: $J^1$ is a 2- or 3-substituent; $J^2$ is a 6- or 7-substituent; $J^1$ and $J^2$ are each independently a group of the formula —NHCO(CH$_2$)$_n$NR$^1$R$^2$, wherein: n is an integer from 1 to 5; and, $R^1$ and $R^2$ are independently hydrogen, $C_{1-7}$alkyl, $C_{3-20}$heterocyclyl, or $C_{5-20}$aryl, or $R^1$ and $R^2$, taken together with the nitrogen atom to which they are attached, form a heterocyclic ring having from 3 to 8 ring atoms; and wherein, when K is a 9-substituent, K is a group of the formula —N(R$^N$)Q, wherein: $R^N$ is an amino substituent and is hydrogen, $C_{1-7}$alkyl, $C_{3-20}$heterocyclyl, or $C_{5-20}$aryl; and, Q is $C_{1-7}$alkyl, $C_{3-20}$heterocyclyl, or $C_{5-20}$aryl, and is optionally substituted; and pharmaceutically acceptable salts, esters, amides, solvates, hydrates and protected forms thereof. The present invention also pertains to pharmaceutical compositions comprising such compounds, and the use of such compounds and compositions, both in vitro and in vivo, to inhibit telomerase, to regulate cell proliferation, and in the treatment of proliferative conditions, such as cancer.

58 Claims, 7 Drawing Sheets

OTHER PUBLICATIONS

Hagan, D.H., et al., 1998, "Antitumour Polycyclic Acridines, Part 3," *J. Chem. Soc., Perkin Trans. 1*, pp. 915-923.

Harrison, R.J., et al., 1999, "Human Telomerase Inhibition by Substituted Acridine Derivatives," *Bioorganic & Medicinal Chemistry Letters*, vol. 9, pp. 2463-2468.

Hoffmann, S., et al., 1986, "Synthese bisbasisch-substituierter Acridine als potentielle Nucleinsaureeffecktoren," *Zeitschrift fur Chemie*, vol. 26, No. 9, pp. 331-332. (Partial English Translation Enclosed).

Julino, M., et al., 1998, "Antitumour Polycyclic Acridines, Part 5," *J. Chem. Soc., Perkin Trans. 1*, pp. 1677-1684.

Klopman, G., et al., 1987, "Computer-Automated Structure Evaluation of Antiluekemic 9-Anilinoacridines," *Molecular Pharmacology*, vol. 31, pp. 457-476.

Korolev, B.A., et al., 1976, "Preparation of 2-Aminoacridan by the Reduction of 2-Amino-9-Acridanone with Biborane," *J. Gen. Chem. USSR (Engl. Trans.)*, vol. 46, pp. 2250-2252.

Korolev, B.A., et al., 1977, "Acridines. II. Selective Reduction of Nitro Derivatives of 2-Amino-9-Acridanone with Diborane," *J. Gen. Chem. USSR (Engl. Trans.)*, vol. 47, pp. 2118-2122.

Matsumura, K., 1929, "The Synthesis of Certain Acridine Compounds," *J. Amer. Chem. Soc.*, vol. 51, pp. 816-820.

Moisan, M., et al., 1993, "New α,ω-Diamido and α,ω-Diamino Mono- and Di-Bridged Acridine Dimers," *Monatshefte fur Chemie*, vol. 124, pp. 23-35.

Neidle, S., et al., 1999, "Telomerase as an Anti-Cancer Target: Current Status and Future Prospects," *Anti-Cancer Drug Design*, vol. 14, pp. 341-347.

Perry, P.J., et al., 1998, "1,4- and 2,6-Disubstituted Amidoanthracene-9,10-dione Derivatives as Inhibitors of Human Telomerase," *J. Med. Chem.*, vol. 41, No. 17, pp. 3253-3260.

Perry, P.J., et al., 1998, "Human Telomerase Inhibition by Regioisomeric Disubstitued Amidoanthracene-9,10-diones," *J. Med. Chem.*, vol. 41, No. 24, pp. 4873-4884.

Perry, P.J. 1998, "Telomeres and Telomerase: Targets for Cancer Chemotherapy?," *Exp. Opin. Ther. Patents*, vol. 8, No. 12, pp. 1567-1586.

Perry, P.J., et al., 1999, "2,7-Disubstituted Amidofluorenone Derivatives as Inhibitors of Human Telomerase," *J. Med. Chem.*, vol. 42, No. 14, pp. 2679-2684.

Perry, P.J., et al., 1999, "Design, Synthesis and Evaluation of Human Telomerase Inhibitors Based Upon a Tetracyclic Structural Motif," *Anti-Cancer Drug Design*, vol. 14, pp. 373-382.

Read et al., Apr. 24, 2001, "Structure-based design of selective and potent G quadruplex-mediated telomerase inhibitors," *Proceedings of the National Academy of Science*, vol. 98, No. 9, pp. 4844-4849.

Read, M.A., et al., 1999, "Molecular Modeling Studies on G-Quadruplex Complexes of Telomerase Inhibitors: Structure-Activity Relationships," *J. Med. Chem.*, vol. 42, pp. 4538-4546.

Sharma, S., et al., 1997, "Preclinical and Clinical Strategies for Development of Telomerase and Telomere Inhibitors," *Annals of Oncology*, vol. 8, pp. 1063-1074.

Sun, D., et al., 1997, "Inhibition of Human Telomerase by a G-Quadruplex-Interactive Compound," *J. Med. Chem.*, vol. 40, pp. 2113-2116.

Urquidi, V., et al., 1998, "Telomerase in Cancer: Clinical Applications," *Ann. Med.*, vol. 30, pp. 419-430.

Lorente et al, Tetrahedron Letters, 1996, vol. 37, No. 25, pp. 4417-4420.

Perry et al, J. Med. Chem., 1998, vol. 41, pp. 3253-3260.

Read et al, PNAS, Apr. 24, 2001, 98(9), pp. 4844-4849.

Li et al, (2001): Biochemistry, vol. 40, pp. 15194-15202.

* cited by examiner

THERAPEUTIC ACRIDONE AND ACRIDINE COMPOUNDS

RELATED APPLICATION

This application is a divisional of U.S. application Ser. No. 10/332,261, filed 4 Apr. 2003 (allowed), which is a U.S. national phase of international application PCT/GB01/03046, filed 6 Jul. 2001, which designated the U.S. and claims benefit of U.S. provisional application Ser. No. 60/216,624, filed 7 Jul. 2000, the entire contents of each of which are incorporated herein by reference.

TECHNICAL FIELD

This invention pertains generally to the field of telomerase inhibitors and antiproliferative agents, and more specifically to certain acridone and acridine compounds which inhibit telomerase and/or regulate cell proliferation. The present invention also pertains to pharmaceutical compositions comprising such compounds, and the use of such compounds and compositions, both in vitro and in vivo, to inhibit telomerase, to regulate cell proliferation, and in the treatment of proliferative conditions, such as cancer.

BACKGROUND

Mammalian cells are normally subject to tight controls regulating replication in order to maintain organ structure and function. Conversely, the disease of cancer is characterized by uncontrolled proliferation. Compromise of any of the steps involved in cell cycle regulation could be involved in escape from regulatory mechanisms and therefore lead to neoplasia. However, even if a cell escapes proliferation suppression, there are limitations to the number of replicative cycles it can progress through before safety mechanisms cause cell cycle shutdown, and this restriction is thought to be a component of the process of organismal aging. Although aging is a complex process, a major candidate for the molecular signal for replicative senescence is that of telomere shortening. Telomeres are nucleoprotein structures at the ends of linear chromosomes consisting of DNA sequences arranged in tandemly repeated units which extend from less than 100 to several thousands of bases. In contrast to chromosome ends created by random breakage, telomeres are stable structures not prone to degradation or fusion with other chromosome ends and are not subject to DNA repair mechanisms.

During each round of cellular replication, both strands of DNA separate and daughter strands are synthesized in a slightly different manner on the leading and lagging strand. While the lead strand replicates in a continuous fashion using conventional DNA polymerase, the lagging strand replicates in a discontinuous fashion using Okazaki fragments. The gaps between individual Okazaki fragments are filled by the regular DNA polymerase. However, this sets the stage for a potential "end replication problem." This arises because Okazaki fragment priming will not necessarily start at the very end of the DNA and because the RNA primer, once removed, would result in a portion of unreplicated 3'-DNA (an unrepaired 3'-overhang). This can lead to a loss of 50-200 base pairs with every round of somatic cell division, with eventual shortening of telomeres to a length that coincides with the activation of an antiproliferative mechanism termed "mortality stage 1" (M1), and at this stage, senescence in somatic cells occurs. Thus, telomere shortening functions as a "mitotic clock" and limits division in somatic cells to about 50-70 times, thereby contributing to cell aging.

In some cells, due to various mechanisms, the M1 stage is bypassed and cells can continue to divide until telomeres become critically shortened ("mortality stage 2," M2). At this M2 stage, in many immortalized cells, a specialized DNA polymerase called "telomerase" appears and utilizes its internal RNA template to synthesize the telomeric sequence and compensate for the loss of telomeric DNA due to incomplete replication. This prevents further shortening of telomeres, and the resulting stabilization of their length contributes to immortalization.

Telomerase is not expressed, or if it is, its activity is repressed, in most normal mammalian somatic cells. Exceptions to this rule include male germ line cells and some epithelial stem cells (e.g., as in the intestinal crypts, the basal layer of the epidermis, and within human hair follicles).

Nonetheless, both telomerase activity and shortened but stabilized telomeres have been detected in the majority of tumours examined (and in over 90% of all human cancers examined), and consequently, telomeres and telomerase are recognized targets for anti-neoplastic (e.g., cancer) chemotherapy.

The absence of telomerase in most normal cells makes this enzyme a particularly attractive target, considering that its inhibition would probably cause minimal damage to the whole patient. The fact that tumour cells have shorter telomeres and higher proliferation rates than normal replicative cell populations suggests that a therapeutic telomerase inhibitor may cause tumour cell death well before damage to regenerative tissues occurs, thereby minimizing undesirable side-effects.

For a more detailed discussion of telomeres and telomerase, and their role as anti-proliferative targets, see, for example, Sharma et al., 1997; Urquidi et al., 1998; Perry et al., 1998c; Autexier, 1999; and Neidle et al., 1999, and references therein.

A number of polycyclic compounds, including polycyclic acridines, anthraquinones, and fluorenones have been shown to inhibit telomerase and/or to have anti-tumour effects in vitro. See, for example, Bostock-Smith et al., 1999; Gimenez-Arnau et al., 1998; Gimenez-Arnau et al., 1998;. Hagan et al., 1997; Hagan et al., 1998; Harrison et al., 1999; Julino et al., 1998; Perry et al., 1998a, 1998b, 1999a, 1999b; Sun et al., 1997.

Harrison et al., 1999, describe certain 3,6-disubstituted acridines which are shown to inhibit telomerase, and to inhibit cell growth in certain ovarian carcinoma cell lines.

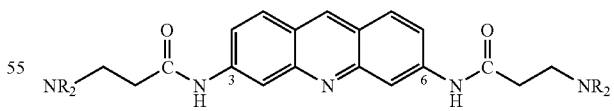

Read et al., April 2001, describe certain 3,6,9-trisubstituted acridines (see compounds 3 and 4 in FIG. 1 therein), including BR-ACO-19 and BR-ACO-20 which are shown to have potent in vitro inhibitory activity against human telomerase.

Although many are known, there remains a great need for potent telomerase inhibitors and antitumour agents, particularly for such compounds which offer additional pharmacological advantages. For example, particularly preferred telomerase inhibitors are ones which are characterized by one or more of the following properties:

(a) no inhibition of Taq polymerase at 10-50 μM (in order to provide specificity and eliminate broad-spectrum polymerase inhibitors);
(b) cell free telomerase inhibition (at <1 μM) at concentrations more than 5 to 10-fold less than for concentrations for acute cytotoxicity;
(c) shortening of telomere length in tumour cells at concentrations 5 to 10-fold less than concentrations for acute cytotoxicity;
(d) telomere shortening in human tumour xenografts; and,
(e) oral bioavailability.

SUMMARY OF THE INVENTION

One aspect of the invention pertains to active compounds as described herein.

Another aspect of the invention pertains to a composition comprising an active compound as described herein and a pharmaceutically acceptable carrier or diluent.

Another aspect of the invention pertains to an active compound as described herein for use in a method of treatment of the human or animal body.

Another aspect of the invention pertains to use of an active compound as described herein for the manufacture of a medicament for use in the treatment of a proliferative condition.

Another aspect of the invention pertains to a method of inhibiting telomerase in vitro or in vivo, comprising contacting a cell with an effective amount of an active compound as described herein.

Another aspect of the invention pertains to a method of regulating cell proliferation, in vitro or in vivo, comprising contacting a cell with an effective amount of an active compound as described herein.

Another aspect of the invention pertains to a method for the treatment of a proliferative condition comprising administering to a subject suffering from said proliferative condition a therapeutically-effective amount of an active compound as described herein.

As will be appreciated by one of skill in the art, features and preferred embodiments of one aspect of the invention will also pertain to other aspect of the invention.

DETAILED DESCRIPTION OF THE INVENTION

Compounds

Figure 1:
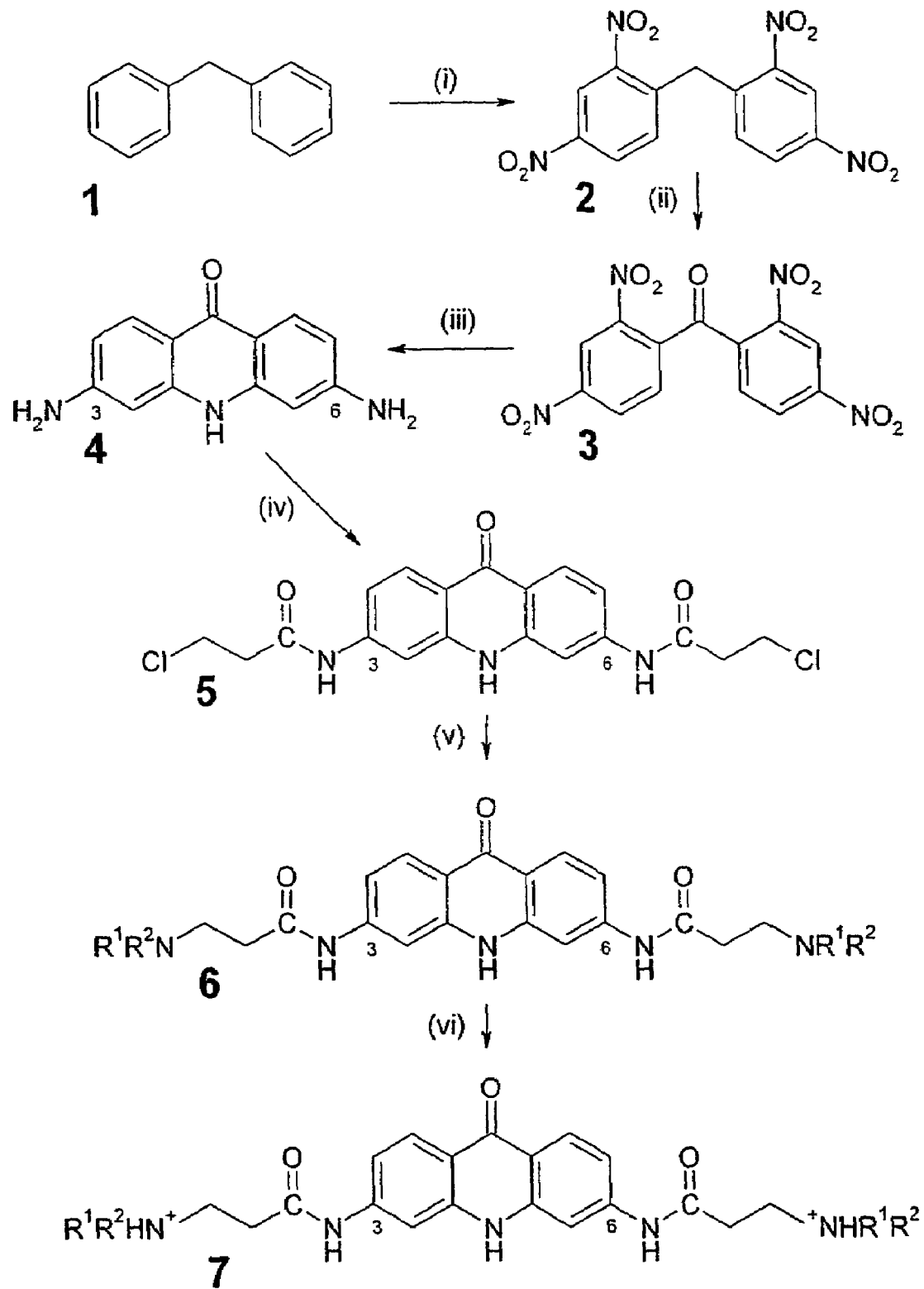
FIG. 1 is a scheme illustrating a chemical synthesis method for certain 3,6-disubstituted acridones of the present invention.

The present invention pertains generally to a class of compounds referred to herein as "acridones" and "acridines" which have the following general formula:

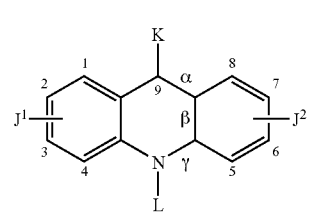

(1)

wherein either:

(a) K is =O, L is —H, α is a single bond, β is a double bond, γ is a single bond (i.e., "acridones"); or,
(b) K is a 9-substituent, L is absent, α is a double bond, β is a single bond, γ is a double bond (i.e., "acridines"); and, $J^1$ is a 2- or 3-substituent; and, $J^2$ is a 6- or 7-substituent;

and pharmaceutically acceptable salts, esters, amides, solvates, hydrates, and protected forms thereof.

As will be appreciated by the skilled artisan, the above structure is one of many possible resonance structures which may be drawn to depict the same compound. As used herein, a reference to one such structure is to be considered a reference to all possible corresponding resonance structures.

Thus, in one embodiment, the compounds are "acridines" of the following formula:

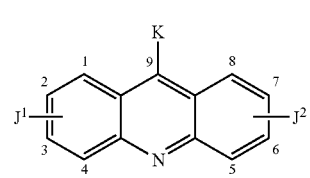

(2)

In another embodiment, the compounds are "acridones" of the following formula:

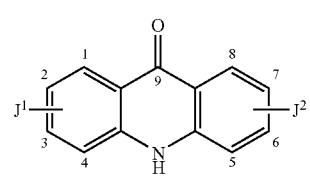

(3)

In one preferred embodiment, whether acridine or acridone, $J^1$ is a 2-substituent and $J^2$ is a 6-substituent (i.e., 2,6-disubstituted). In one preferred embodiment, $J^1$ is a 3-substituent and $J^2$ is a 7-substituent (i.e., 3,7-disubstituted). These embodiments may conveniently be referred to as "symmetrical" compounds.

In one preferred embodiment, whether acridine or acridone, $J^1$ is a 2-substituent and $J^2$ is a 7-substituent (i.e., 2,7-disubstituted), or, equivalently, $J^1$ is a 3-substituent and $J^2$ is a 6-substituent (i.e., 3,6-disubstituted). These embodiments may conveniently be referred to as "non-symmetrical" compounds.

In the compounds of the present invention, $J^1$ and $J^2$ are each independently a group of the formula:

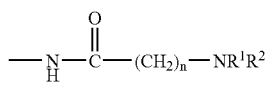

wherein n is an integer from 1 to 5, and —$NR^1R^2$ is a terminal amino group.

In one preferred embodiment, n is an integer from 1 to 4.
In one preferred embodiment, n is an integer from 1 to 3.
In one preferred embodiment, n is 1 or 2.
In one preferred embodiment, n is 1.
In one preferred embodiment, n is 2.
In one preferred embodiment, n is 3.
In one preferred embodiment, n is 4.
In one preferred embodiment, n is 5.

In one preferred embodiment, n is 2, and $J^1$ and $J^2$ are each independently a group of the following formula, wherein —$NR^1R^2$ is a terminal amino group:

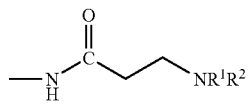

In one preferred embodiment, $J^1$ and $J^2$ are the same.

Thus, in one embodiment, the compounds are acridones, and have the following formula, wherein n is as defined above, and —$NR^1R^2$ is a terminal amino group:

(4)

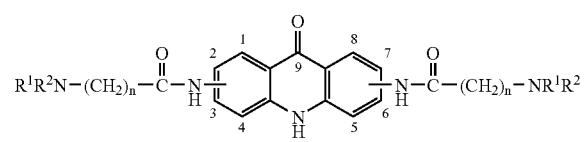

In one preferred embodiment, the compounds are acridones and have the following formula, wherein —$NR^1R^2$ is a terminal amino group:

(5)

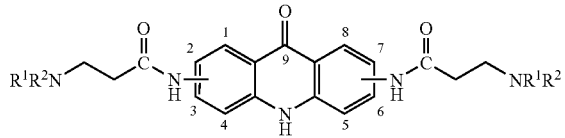

In one preferred embodiment, the compounds are 3,6-disubstituted acridones, and have the following formula, wherein —$NR^1R^2$ is a terminal amino group:

(6)

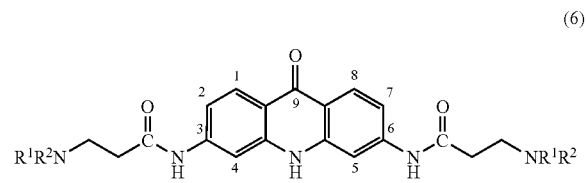

In one preferred embodiment, the compounds are 2,7-disubstituted acridones, and have the following formula, wherein —$NR^1R^2$ is a terminal amino group:

(7)

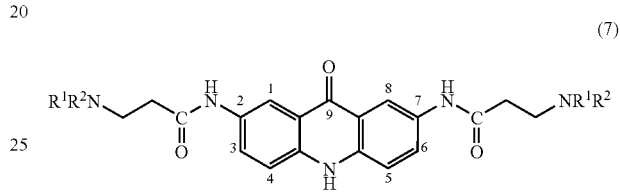

In one preferred embodiment, the compounds are 2,6-disubstituted acridones (alternatively referred to as 3,7-disubstituted acridones), and have the following formula, wherein —$NR^1R^2$ is a terminal amino group:

(8)

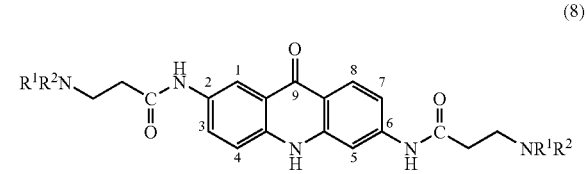

In another embodiment, the compounds are acridines, and have the following formula, wherein n is as defined above, —$NR^1R^2$ is a terminal amino group, and K is a 9-substituent:

(9)

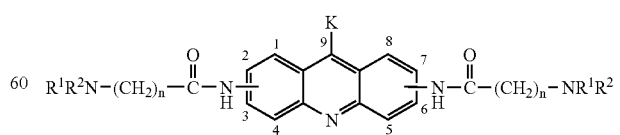

In one preferred embodiment, the compounds are acridines, and have the following formula, wherein —$NR^1R^2$ is a terminal amino group and K is a 9-substituent:

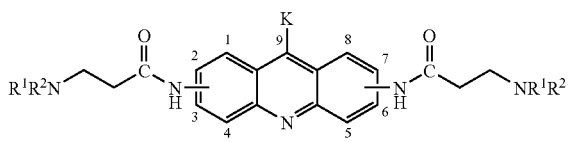

(10)

In one preferred embodiment, the compounds are 3,6,9-trisubstituted acridines, and have the following formula, wherein —NR$^1$R$^2$ is a terminal amino group and K is a 9-substituent:

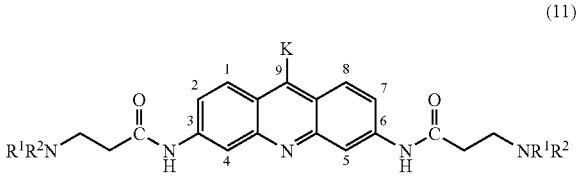

(11)

In one preferred embodiment, the compounds are 2,7,9-trisubstituted acridines, and have the following formula, wherein —NR$^1$R$^2$ is a terminal amino group and K is a 9-substituent:

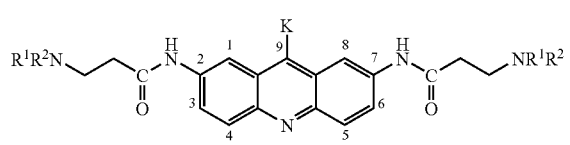

(12)

In one preferred embodiment, the compounds are 2,6,9-trisubstituted acridines (also referred to as 3,7,9-trisubstituted acridines), and have the following formula, wherein —NR$^1$R$^2$ is a terminal amino group and K is a 9-substituent:

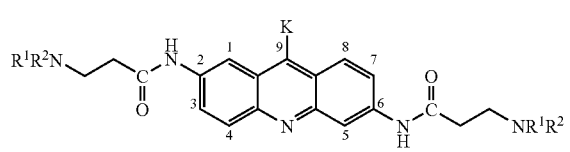

(13)

Terminal Amino Groups, —NR$^1$R$^2$

The term "terminal amino group," as used herein, pertains to a amino group of the formula —NR$^1$R$^2$, wherein R$^1$ and R$^2$ are independently amino substituents, for example, hydrogen, $C_{1-7}$alkyl, $C_{3-20}$heterocyclyl, or $C_{5-20}$aryl, which may themselves be substituted.

In one preferred embodiment, the terminal amino group, —NR$^1$R$^2$, is a secondary amino group, and one of R$^1$ and R$^2$ is —H.

In one preferred embodiment, the terminal amino group, —NR$^1$R$^2$, is a tertiary amino group, and neither R$^1$ nor R$^2$ is —H.

In one preferred embodiment, the terminal amino, group, —NR$^1$R$^2$, is a tertiary amino group, neither R$^1$ nor R$^2$ is —H, and R$^1$ and R$^2$ are the same.

In one preferred embodiment, R$^1$ and R$^2$ are each independently $C_{1-7}$alkyl, which is optionally substituted.

In one preferred embodiment, R$^1$ and R$^2$ are each independently aliphatic saturated $C_{1-7}$alkyl, which is optionally substituted.

In one preferred embodiment, R$^1$ and R$^2$ are each independently aliphatic saturated unsubstituted $C_{1-7}$alkyl.

In one preferred embodiment, R$^1$ and R$^2$ are each independently -Me, -Et, -nPr, -iPr, -nBu, or -tBu.

In one preferred embodiment, the terminal amino group, —NR$^1$R$^2$, is —N(Me)$_2$, —N(Et)$_2$, —N(nPr)$_2$, —N(iPr)$_2$, —N(nBu)$_2$, or —N(tBu)$_2$.

In one preferred embodiment, R$^2$ is H and R$^1$ and is $C_{1-7}$alkyl, which is optionally substituted.

In one preferred embodiment, R$^2$ is H and R$^1$ and is aliphatic saturated $C_{1-7}$alkyl, which is optionally substituted.

In one preferred embodiment, R$^2$ is H and R$^1$ and is aliphatic saturated unsubstituted $C_{1-7}$alkyl.

In one preferred embodiment, R$^2$ is H and R$^1$ and is -Me, -Et, -nPr, -iPr, -nBu, or -tBu.

In one preferred embodiment, the terminal amino group, —NR$^1$R$^2$, is —NHMe, —NHEt, —NH(nPr), —NH(iPr), —NH(nBu), or —NH(tBu).

In one preferred embodiment, R$^1$ and R$^2$ are each independently $C_{5-20}$aryl, which is optionally substituted.

In one preferred embodiment, R$^1$ and R$^2$ are each independently $C_{5-20}$carboaryl, which is optionally substituted.

In one preferred embodiment, R$^1$ and R$^2$ are each independently $C_{5-20}$heteroaryl, which is optionally substituted.

In one preferred embodiment, R$^1$ and R$^2$ are each independently phenyl, which is optionally substituted.

Alternatively, R$^1$ and R$^2$, taken together with the nitrogen atom to which they are attached, may form a heterocyclic ring having from 3 to 8 ring atoms (e.g., a $C_{3-8}$heterocyclyl group), more preferably 5 to 8 ring atoms (e.g., a $C_{5-8}$heterocyclyl group), which heterocyclic ring may be saturated, partially unsaturated, or fully unsaturated, and is optionally substituted.

In one preferred embodiment, R$^1$ and R$^2$, taken together with the nitrogen atom to which they are attached, form a saturated heterocyclic ring having from 3 to 8 ring atoms (e.g., a $C_{3-8}$heterocyclyl group), more preferably 5 to 8 ring atoms (e.g., a $C_{5-8}$heterocyclyl group), which heterocyclic ring is optionally substituted.

In one preferred embodiment, R$^1$ and R$^2$, taken together with the nitrogen atom to which they are attached, form a saturated heterocyclic ring having from 3 to 8 ring atoms (e.g., a $C_{3-8}$heterocyclyl group), more preferably 5 to 8 ring atoms (e.g., a $C_{5-8}$heterocyclyl group), wherein only one of said ring atoms is nitrogen, and all others are carbon, and which heterocyclic ring is optionally substituted.

In one preferred embodiment, R$^1$ and R$^2$, taken together with the nitrogen atom to which they are attached form a cyclic amino group of the following formula, wherein q is an integer from 2 to 7, and wherein said group is optionally substituted:

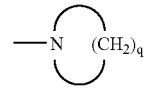

In one preferred embodiment, q is an integer from 3 to 7.
In one preferred embodiment, q is an integer from 4 to 7.
In one preferred embodiment, q is an integer from 4 to 6.
In one preferred embodiment, q is 4 or 5.

In one preferred embodiment, the terminal amino group, —NR$^1$R$^2$, is one of the following cyclic amino groups, and is optionally substituted:

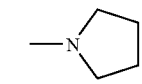
azolidino
(pyrrolidino)

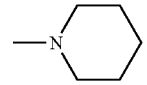
perhydroazino
(piperidino)

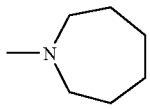
perhydroazepino

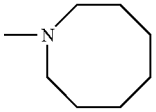
perhydroazocino

In one preferred embodiment, R$^1$ and R$^2$, taken together with the nitrogen atom to which they are attached, form a heterocyclic ring having from 3 to 8 ring atoms (e.g., a C$_{3-8}$heterocyclyl group), more preferably 5 to 8 ring atoms (e.g., a C$_{3-8}$heterocyclyl group), wherein said ring has at least two heteroatoms selected from nitrogen, oxygen, and sulfur, which heterocyclic ring may saturated, partially unsaturated, or fully unsaturated, and is optionally substituted.

In one preferred embodiment, R$^1$ and R$^2$, taken together with the nitrogen atom to which they are attached, form a saturated heterocyclic ring having from 3 to 8 ring atoms (e.g., a C$_{3-8}$heterocyclyl group), more preferably 5 to 8 ring atoms (e.g., a C$_{3-8}$heterocyclyl group), wherein said ring has at least two heteroatoms selected from nitrogen, oxygen, and sulfur, which heterocyclic ring is optionally substituted.

In one preferred embodiment, the terminal amino group, —NR$^1$R$^2$, is one of the following groups, and is optionally substituted:

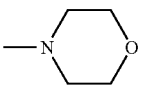
morpholino

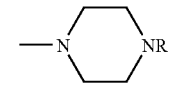
piperazino wherein R is an amino substituent, for example, hydrogen, C$_{1-7}$alkyl, C$_{3-20}$heterocyclyl, or C$_{5-20}$aryl.

In one preferred embodiment, —NR$^1$R$^2$, is piperazino, and R is -Me or -Et.

When R$^1$ and R$^2$, taken together with the nitrogen atom, form a heterocyclic ring, the ring may optionally be bridged, fused, and/or spiro in nature, and is optionally substituted. An example of such a terminal amino group, —NR$^1$R$^2$, is shown below:

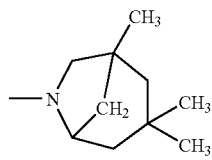

As mentioned above, the groups R$^1$ and R$^2$, or the heterocyclic ring formed from R$^1$ and R$^2$ and the nitrogen atom to which they are attached, are optionally substituted.

For example, in one preferred embodiment, R$^1$ and R$^2$ and the nitrogen atom to which they are attached form a cyclic amino group, —NR$^1$R$^2$, which has one or more substituents selected from: C$_{1-7}$alkyl, C$_{3-20}$aryl-C$_{1-7}$alkyl, C$_{3-20}$aryl, C$_{1-7}$alkyl-C$_{3-20}$aryl, hydroxy C$_{1-7}$hydroxyalkyl, and C$_{1-7}$aminoalkyl.

In one preferred embodiment, R$^1$ and R$^2$ and the nitrogen atom to which they are attached form a cyclic amino group, —NR$^1$R$^2$, which has one or more substituents selected from: -Me, -Et, —CH$_2$Ph, —OH, —CH$_2$OH, —CH$_2$CH$_2$OH, —CH$_2$NH$_2$, and —CH$_2$CH$_2$NH$_2$.

In one preferred embodiment, the terminal amino group, —NR$^1$R$^2$, is one of the following substituted cyclic amino groups:

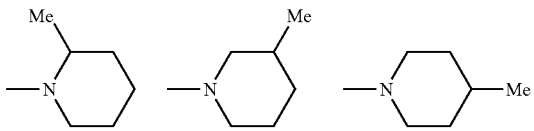

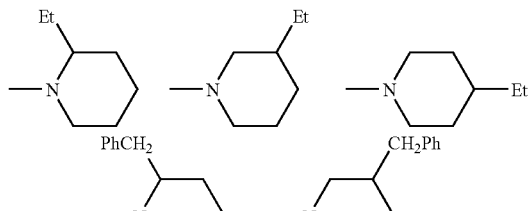

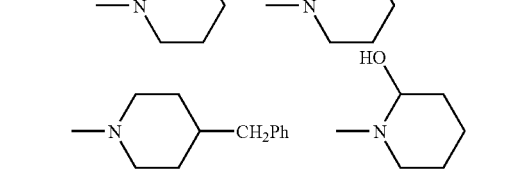

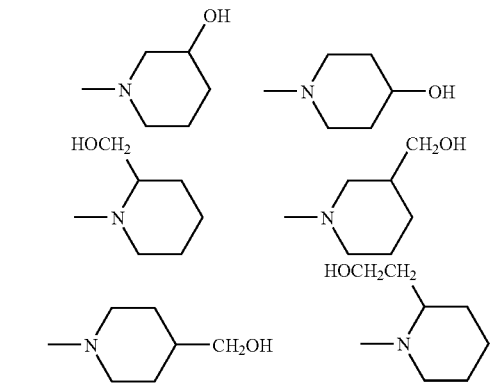

-continued

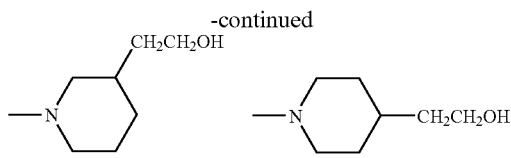

9-Substituents, K

In the above acridine compounds, wherein K is a 9-substituent, K is a group of the formula:

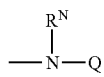

wherein:
R$^N$ is an amino substituent and is hydrogen, C$_{1-7}$alkyl, C$_{3-20}$heterocyclyl, or C$_{5-20}$aryl; and,
Q is C$_{1-7}$alkyl, C$_{3-20}$heterocyclyl, or C$_{5-20}$aryl, and is optionally substituted.

Thus, the acridine compounds have the following formula:

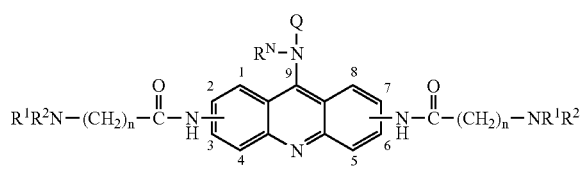

(14)

And, as mentioned above, in one preferred embodiment wherein n is 2, the acridine compounds have the following formula:

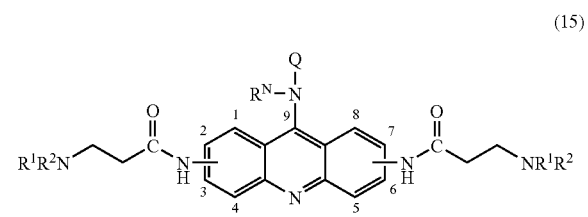

(15)

The Nitrogen Substituent, R$^N$

In one preferred embodiment, R$^N$ is hydrogen, C$_{1-7}$alkyl, C$_{3-20}$heterocyclyl, or C$_{5-20}$aryl.

In one preferred embodiment, R$^N$ is hydrogen or C$_{1-7}$alkyl.

In one preferred embodiment, R$^N$ is hydrogen or aliphatic saturated C$_{1-7}$alkyl.

In one preferred embodiment, R$^N$ is —H, -Me, -Et, -nPr, or -iPr.

In one preferred embodiment, R$^N$ is —H.

The Moiety, Q, as Optionally Substituted Aryl Group

In one embodiment, Q is a C$_{5-20}$aryl group, which is optionally substituted. In one embodiment, Q is a C$_6$aryl group (e.g., C$_6$carboaryl or C$_6$heteroaryl), which is optionally substituted.

In one embodiment, Q is an azinyl (pyridyl) group which is optionally substituted, and K is a group of the formula:

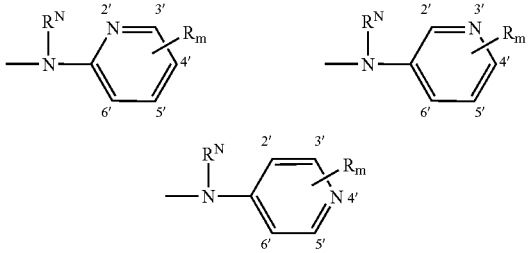

wherein m is an integer from 0 to 4, and each R is independently a substituent as defined herein.

In one embodiment, Q is a substituted diazinyl (e.g., pyridazinyl, pyrimidinyl, pyrazinyl) group which is optionally substituted, and K is, for example, a group having one of the following formulae:

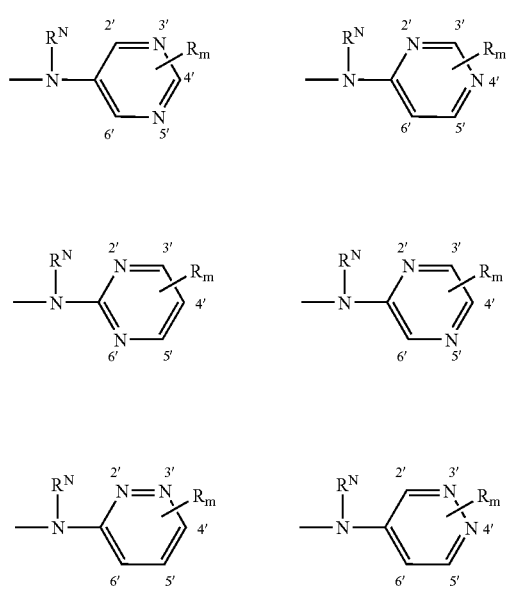

wherein m is an integer from 0 to 3, and each R is independently a substituent as defined herein.

In one embodiment, Q is a phenyl group which is optionally substituted, and K is a group of the formula:

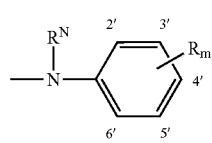

wherein m is an integer from 0 to 5, and each R is independently a substituent as defined herein.

In this embodiment, the acridine compounds have the formula:

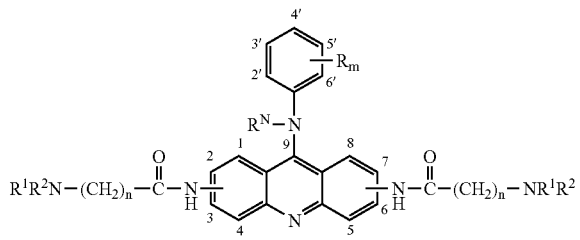

(16)

In one preferred embodiment wherein n is 2, the acridine compounds have the following formula:

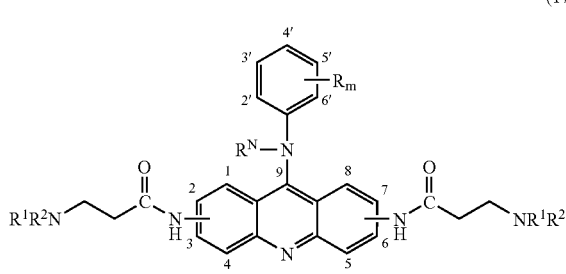

(17)

In one preferred embodiment, m is an integer from 0 to 4.
In one preferred embodiment, m is an integer from 0 to 3.
In one preferred embodiment, m is an integer from 0 to 2.
In one preferred embodiment, m is 0 or 1.
In one preferred embodiment, m is an integer from 1 to 5.
In one preferred embodiment, m is an integer from 1 to 4.
In one preferred embodiment, m is an integer from 1 to 3.
In one preferred embodiment, m is 1 or 2.
In one preferred embodiment, m is 5.
In one preferred embodiment, m is 4.
In one preferred embodiment, m is 3.
In one preferred embodiment, m is 2.
In one preferred embodiment, m is 1.
In one preferred embodiment, m is 0.

If the phenyl group has less than the full complement of ring substituents, R, they may be arranged in any combination. For example, if m is 1, R may be in the 2'-, 3'-, 4'-, 5'-, or 6'-position. Similarly, if m is 2, the two R groups may be in, for example, the 2',3'-, 2',4'-, 2',5'-, 2',6'-, 3',4'-, or 3',5'-positions. If m is 3, the three R groups may be in, for example, the 2',3',4'-, 2',3',5'-, 2',3',6'-, or 3',4',5'-positions.

Examples of some preferred phenyl substituents include, but are not limited to, halo, amino, hydroxy, ether (e.g., $C_{1-7}$alkoxy), thio, thioether (e.g., $C_{1-7}$alkylthio), $C_{1-7}$alkyl, $C_{1-7}$haloalkyl, acyl (e.g., $C_{1-7}$alkylacyl), amido (e.g., $C_{1-7}$alkylamido), carboxy, cyano, and aminoalkyl.

Examples of substituted phenyl groups which are suitable as Q include, but are not limited to, the following:
monohalophenyl, for example,
4'-fluorophenyl, 3'-fluorophenyl, 2'-fluorophenyl;
4'-chlorophenyl, 3'-chlorophenyl, 2'-chlorophenyl;
4'-bromophenyl, 3'-bromophenyl, 2'-bromophenyl.
dihalophenyl, for example,
2',3'-difluorophenyl, 2',3'-dichlorophenyl;
2',4'-difluorophenyl, 2',4'-dichlorophenyl;
2',5'-difluorophenyl, 2',5'-dichlorophenyl;
3',4'-difluorophenyl, 3',4'-dichlorophenyl;
3',5'-difluorophenyl, 3',5'-dichlorophenyl.
monoaminophenyl, for example,
4'-aminophenyl, 3'-aminophenyl, 2'-aminophenyl.
diaminophenyl, for example,
2',3'-diaminophenyl, 2',4'-diaminophenyl, 2',5'-diaminophenyl,
3',4'-diaminophenyl, 3',5'-diaminophenyl.
monohydroxyphenyl, for example,
4'-hydroxyphenyl, 3'-hydroxyphenyl, 2'-hydroxyphenyl.
monomethoxyphenyl, for example,
4'-methoxyphenyl, 3'-methoxyphenyl, 2'-methoxyphenyl.
monothiophenyl, for example,
4'-thiophenyl, 3'-thiophenyl, 2'-thiophenyl.
monomethylthiophenyl, for example,
4'-methylthiophenyl, 3'-methylthiophenyl, 2'-methylthiophenyl.
monomethylphenyl, for example,
4'-methylphenyl, 3'-methylphenyl, 2'-methylphenyl.
monotrifluoromethylphenyl, for example,
4'-trifluoromethylphenyl, 3'-trifluoromethylphenyl, 2'-trifluoromethylphenyl.
monoacetylphenyl, for example,
4'-acetylphenyl, 3'-acetylphenyl, 2'-acetylphenyl.
monoamidophenyl, for example,
4'-amidophenyl, 3'-amidophenyl, 2'-amidophenyl.
4'-(methylamido)phenyl, 3'-(methylamido)phenyl, 2'-(methylamido)phenyl.
monocarboxyphenyl, for example,
4'-carboxyphenyl, 3'-carboxyphenyl, 2'-carboxyphenyl.
monocyanophenyl, for example,
4'-cyanophenyl, 3'-cyanophenyl, 2'-cyanophenyl.
mono(aminoalkyl)phenyl, for example,
4'-aminoalkylphenyl, 3'-aminoalkylphenyl, 2'-aminoalkylphenyl;
4'-aminomethylphenyl, 3'-aminomethylphenyl, 2'-aminomethylphenyl;
4'-aminoethylphenyl, 3'-aminoethylphenyl, 2'-aminoethylphenyl.
monohalo-mono(aminoalkyl)phenyl, for example,
2'-halo-4'-aminoalkylphenyl, 2'-halo-3'-aminoalkylphenyl, 3'-halo-2'-aminoalkylphenyl, 3'-halo-4'-aminoalkylphenyl,
4'-halo-2'-aminoalkylphenyl, 4'-halo-3'-aminoalkylphenyl.

In one preferred embodiment, Q is a 4'-aminophenyl group, and K is a group of the formula:

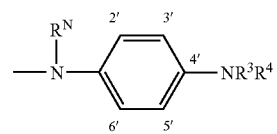

wherein $-NR^3R^4$ is as defined above for $-NR^1R^2$.

In this embodiment, the acridine compounds have the formula:

(18)

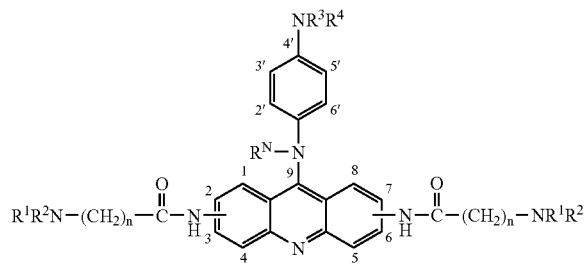

In one preferred embodiment wherein n is 2, the acridine compounds have the following formula:

(19)

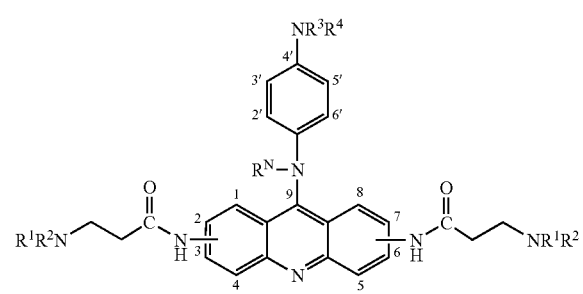

In one preferred embodiment, Q is an (amino-alkyl-amido) phenyl group, and K is a group of the formula:

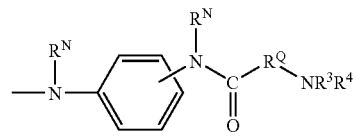

wherein $R^Q$ is a $C_{1-10}$alkylene group, and —$NR^3R^4$ is as defined above for —$NR^1R^2$.

In one preferred embodiment, Q is a 4'-(amino-alkyl-amido)phenyl group, and K is a group of the formula:

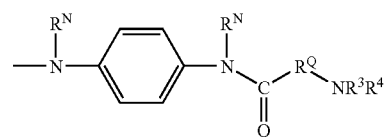

wherein $R^Q$ is a $C_{1-10}$alkylene group, and —$NR^3R^4$ is as defined above for —$NR^1R^2$.

In one preferred embodiment, Q is —$(CH_2)_p$—, wherein p is an integer from 1 to 10, and K has the following formula:

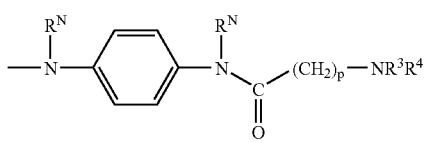

In this embodiment, the acridine compounds have the formula:

(20)

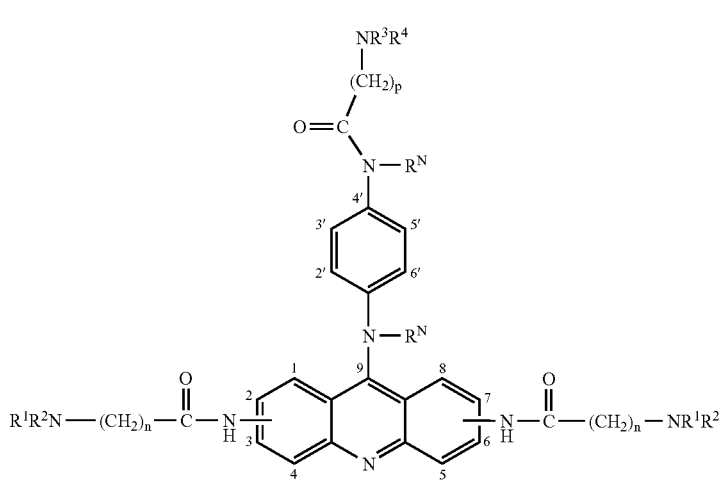

In one preferred embodiment wherein n is 2, the acridine compounds have the following formula:

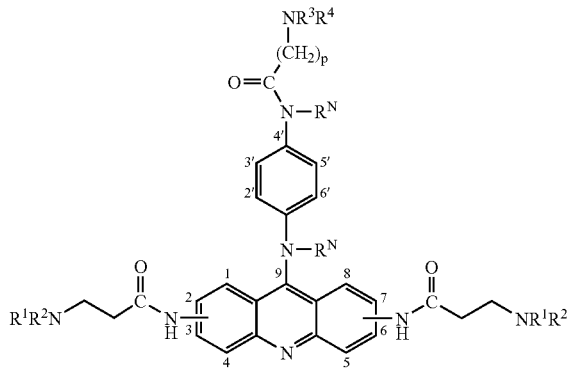

(21)

In one embodiment, p is an integer from 1 to 8. In one embodiment, p is an integer from 1 to 6. In one embodiment, p is an integer from 1 to 4. In one embodiment, p is an integer from 2 to 6. In one embodiment, p is an integer from 2 to 4. In one embodiment, p is 2 or 3.

In one embodiment, p is 2, and K is a group of the formula:

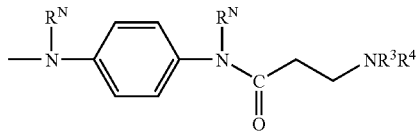

In one embodiment, K is a group of the formula:

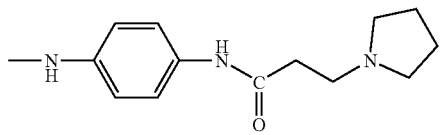

In one preferred embodiment, Q is a certain substituted phenyl group, and K is a group of the formula:

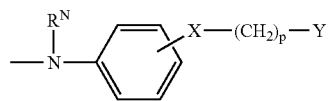

wherein:
X is $-N(N^R)-$, $-CH_2-$, $-O-$, or $-S-$;
Y is $-OH$, $-ORY$, or $-NR^3R^4$;
$R^Y$ is $C_{1-7}$alkyl, $C_{3-20}$heterocyclyl, or $C_{5-20}$aryl;
$-NR^3R^4$ is as defined above for $-NR^1R^2$; and,
p is an integer from 1 to 10, as defined above.

In one preferred embodiment, the substituent is para, and K is a group of the formula:

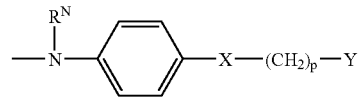

In one embodiment, X is $-N(N^R)-$, $-CH_2-$, $-O-$, or $-S-$, and Y is $-NR^3R^4$.
In one embodiment, X is $-O-$, or $-S-$, and Y is $-OH$, $-OR^Y$, or $-NR^3R^4$.
In one embodiment, X is $-O-$, or $-S-$, and Y is $-NR^3R^4$.
In one embodiment, X is $-O-$, and Y is $-NR^3R^4$.
In one embodiment, X is $-N(N^R)-$ and Y is $-OH$, $-OR^Y$, or $-NR^3R^4$.
In one embodiment, X is $-N(N^R)-$ and Y is $-NR^3R^4$:

The Moiety, Q, as Optionally Substituted Alkyl Group

In one embodiment, Q is a $C_{1-7}$alkyl group, which is optionally substituted.

In one embodiment, Q is a substituted $C_{1-7}$alkyl group, for example, a $C_{1-7}$alkyl group substituted with one or more amino groups, one or more hydroxy groups, one more ether groups, one or more carboxy groups, one or more $C_{3-20}$heterocyclyl groups, one or more $C_{5-20}$aryl, etc.

In one embodiment, Q is an amino substituted $C_{1-7}$alkyl group, that is, a $C_{1-7}$alkyl group substituted with one or more amino groups.

In one embodiment, Q is a hydroxy substituted $C_{1-7}$alkyl group, that is, a $C_{1-7}$alkyl group substituted with one or more hydroxy groups.

In one embodiment, Q is a ether substituted $C_{1-7}$alkyl group, that is, a $C_{1-7}$alkyl group substituted with one or more ether groups. For example, Q may be $-CH_2CH_2-OMe$.

In one embodiment, Q is a carboxy substituted $C_{1-7}$alkyl group, that is, a $C_{1-7}$alkyl group substituted with one or more carboxy groups.

In one embodiment, Q is a $C_{3-20}$heterocyclyl substituted $C_{1-7}$alkyl group, that is, a $C_{1-7}$alkyl group substituted with one or more $C_{3-20}$heterocyclyl groups. For example, Q may be $-CH_2CH_2-$(N-methyl-pyrrolidin-2-yl).

In one embodiment, Q is a $C_{5-20}$aryl substituted $C_{1-7}$alkyl group, that is, a $C_{1-7}$alkyl group substituted with one or more $C_{5-20}$aryl groups. For example, Q may be $-CH_2CH_2$-(pyrid-3-yl).

In one embodiment, Q is an amino substituted aliphatic saturated $C_{1-7}$alkyl group, that is, an aliphatic saturated $C_{1-7}$alkyl group substituted with one or more amino groups.

In one embodiment, Q is an amino substituted linear saturated $C_{1-7}$alkyl group, that is, a linear saturated $C_{1-7}$alkyl group substituted with one or more amino groups.

In one embodiment, Q is a terminally amino substituted linear saturated $C_{1-7}$alkyl group, that is, a linear saturated $C_{1-7}$alkyl group substituted with a terminal amino group, and K is a group of the formula:

wherein p is an integer from 1 to 10, and the group $-NR^3R^4$ is as defined above for $-NR^1R^2$.

In this embodiment, the acridine compounds have the formula:

(22)

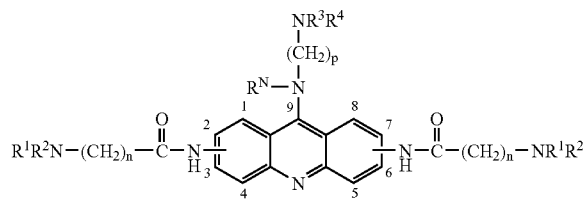

In one preferred embodiment wherein n is 2, the acridine compounds have the following formula:

(23)

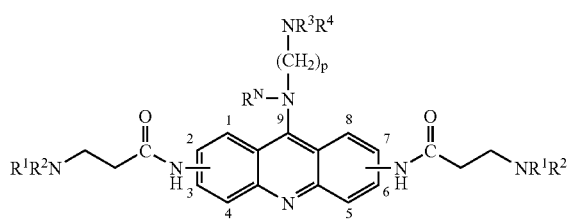

In one embodiment, p is an integer from 1 to 8. In one embodiment, p is an integer from 1 to 6. In one embodiment, p is an integer from 1 to 4. In one embodiment, p is an integer from 2 to 6. In one embodiment, p is an integer from 2 to 4. In one embodiment, p is 2 or 3.

In one embodiment, Q is an amino substituted branched saturated $C_{1-7}$alkyl group, that is, a branched saturated $C_{1-7}$alkyl group substituted with one or more amino groups.

In one embodiment, Q is an amino disubstituted branched saturated $C_{1-7}$alkyl group, that is, a branched saturated $C_{1-7}$alkyl group substituted with two amino groups.

In one embodiment, Q is an amino disubstituted branched saturated $C_{1-7}$alkyl group, and K is a group of the formula:

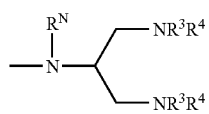

wherein each group —$NR^3R^4$ is as defined above for —$NR^1R^2$.

In one embodiment, Q is, or comprises, an alicyclic saturated $C_{1-7}$alkyl group, which is optionally substituted. In one embodiment, Q is an alicyclic saturated $C_{1-7}$alkyl group, which is optionally substituted. In one embodiment, Q is a saturated $C_{1-7}$cycloalkyl-$C_{1-7}$alkyl group, which is optionally substituted.

In one embodiment, Q is, or comprises, an alicyclic saturated $C_{1-7}$alkyl group, and K is a group of the formula:

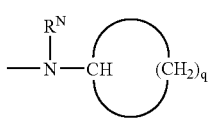

wherein q is as defined above, and wherein the cyclic group is optionally substituted. Examples of preferred substituents include halo, hydroxy, amino, and $C_{1-7}$alkyl.

In one embodiment, Q is, or comprises, an alicyclic saturated $C_{1-7}$alkyl group, and K is a group of one of the following formulae:

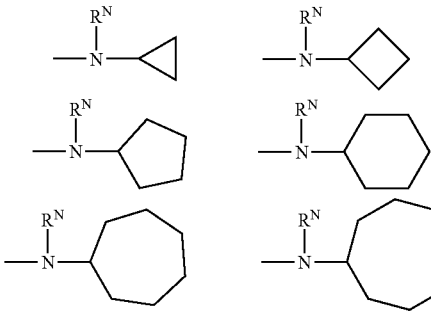

In one embodiment, Q is, or comprises, an alicyclic saturated $C_{1-7}$alkyl group, and K is a group of the formula:

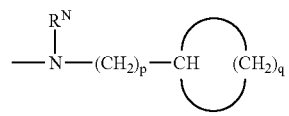

wherein p and q are as defined above, and wherein the cyclic group is optionally substituted. Examples of preferred substituents include halo, hydroxy, amino, and $C_{1-7}$alkyl.

In one embodiment, Q is, or comprises, an alicyclic saturated $C_{1-7}$alkyl group, and K is a group of one of the following formulae:

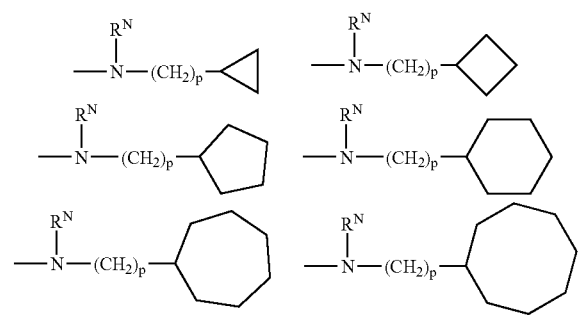

wherein p is as defined above, and wherein the cyclic group is optionally substituted.

Examples of other embodiments, wherein Q is, or comprises, an alicyclic saturated $C_{1-7}$alkyl group, which is optionally substituted include the following:

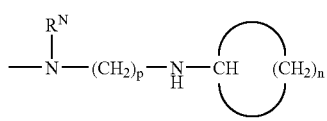

-continued

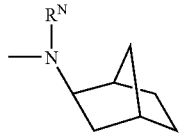

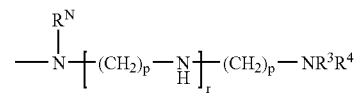

wherein p is as defined above, r is an integer from 1 to 4, and the group —NR³R⁴ is as defined above for —NR¹R². In one embodiment, r is an integer from 1 to 3. In one embodiment, r is 1 or 2. In one embodiment, r is 1.

In one embodiment, Q is an amino substituted polyaminoalkylene group, and K is a group of the formula:

EXAMPLES OF SPECIFIC EMBODIMENTS

Some individual embodiments of the present invention include the following compounds:

| Class | # Free Base HCl Salt | Structure |
|---|---|---|
| 2,6,9-ine | 1 BSU-SB-36/188 SB-ACI-18 | |
| 2,6,9-ine | 2 BSU-SB-36/190 SB-ACI-19 | |
| 2,6,9-ine | 3 BSU-SB-36/194 SB-ACI-17 | |

-continued
| Class | # Free Base HCl Salt | Structure |
|---|---|---|
| 2,6,9-ine | 4 BSU-SB- 36/196 SB-ACI-22 | 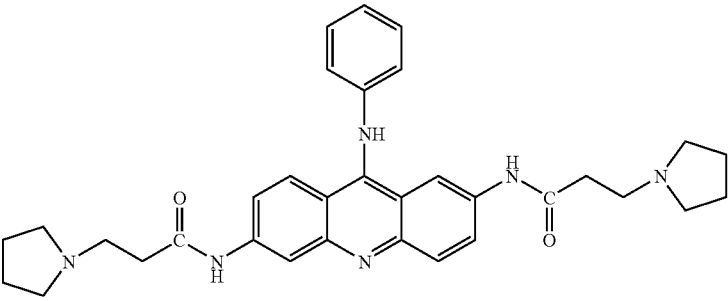 |
| 2,6,9-ine | 5 BSU-SB- 36/198 SB-ACI-20 | 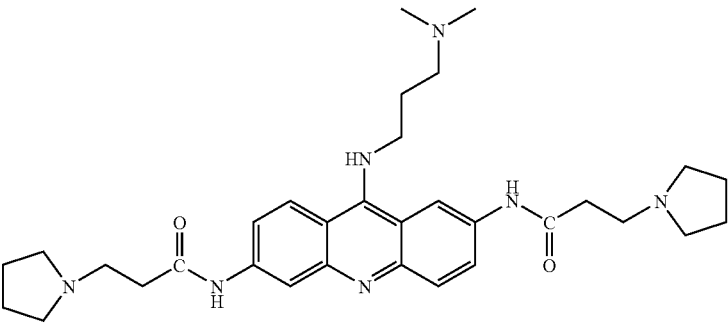 |
| 2,6,9-ine | 6 BSU-SB- 36/200 SB-ACI-21 | 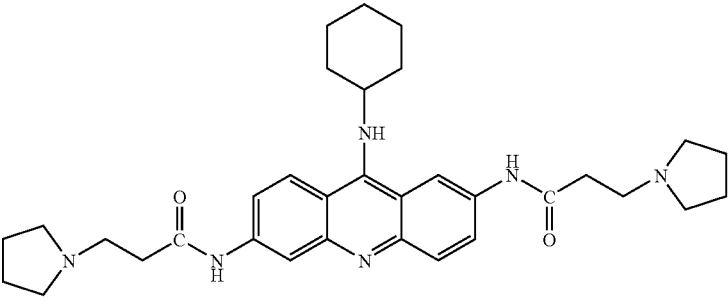 |
| 2,6,9-ine | 7 BSU-SB- 36/202 SB-ACI-16 | 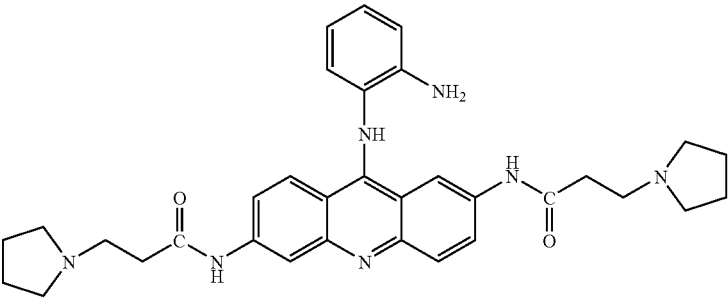 |

-continued
| Class | # Free Base HCl Salt | Structure |
|---|---|---|
| 2,6,9-ine | 8 JH-ACI-104 JH-ACI-105 | 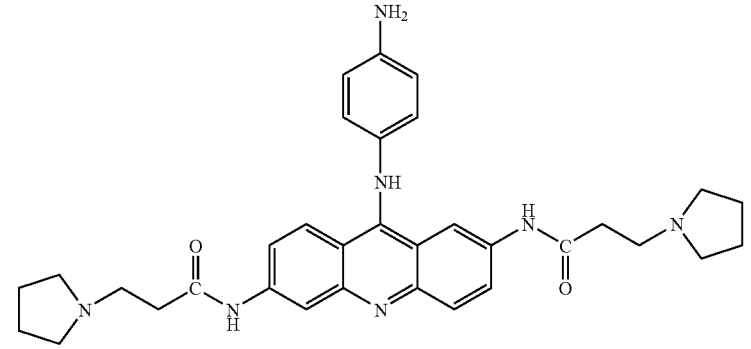 |
| 2,6-one | 9 AR-ACO-10 AR-ACO-11 | 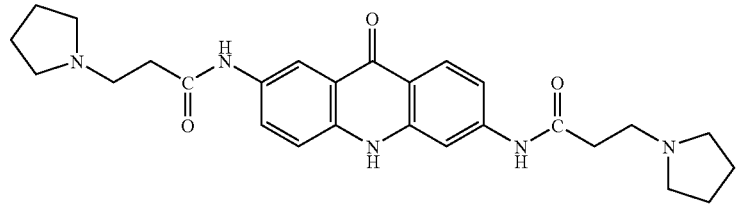 |
| 2,7,9-ine | 10 JM-ACI-10 JM-ACI-11 | 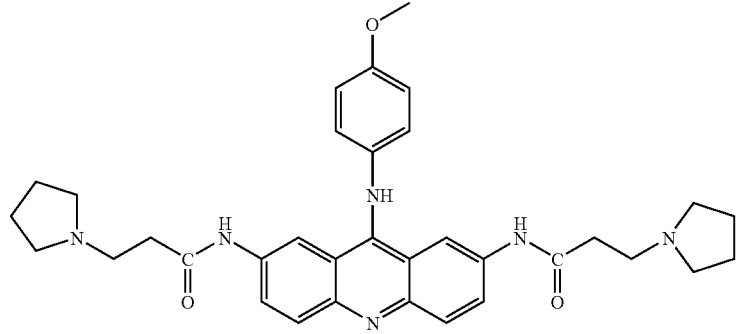 |
| 2,7,9-ine | 11 JM-ACI-29 JM-ACI-30 | 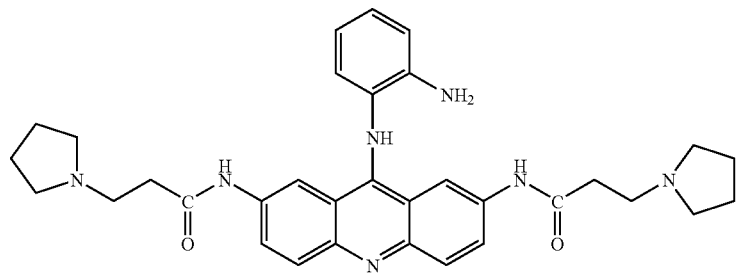 |
| 2,7,9-ine | 12 JM-ACI-31 JM-ACI-32 | 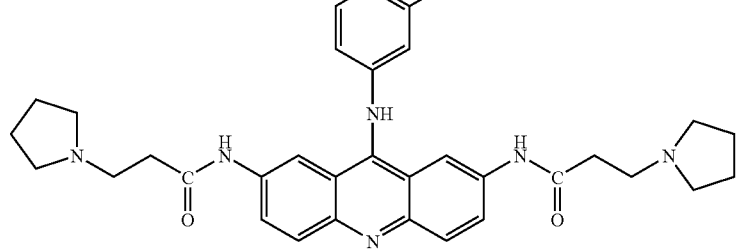 |

-continued
| Class | # Free Base HCl Salt | Structure |
|---|---|---|
| 2,7,9-ine | 13 JM-ACI-33 JM-ACI-34 | 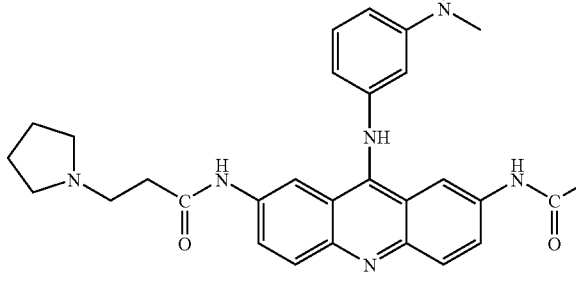 |
| 2,7,9-ine | 14 JM-ACI-35 JM-ACI-36 | 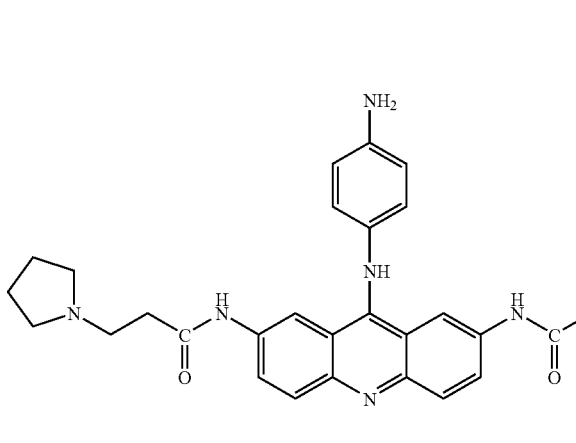 |
| 2,7,9-ine | 15 JM-ACI-37 JM-ACI-38 | 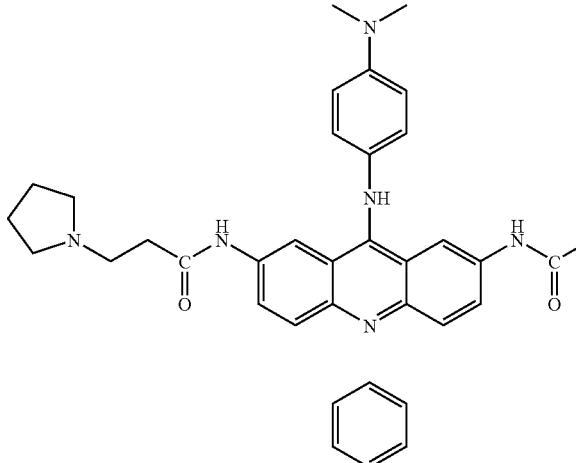 |
| 2,7,9-ine | 16 JM-ACI-39 JM-ACI-40 | 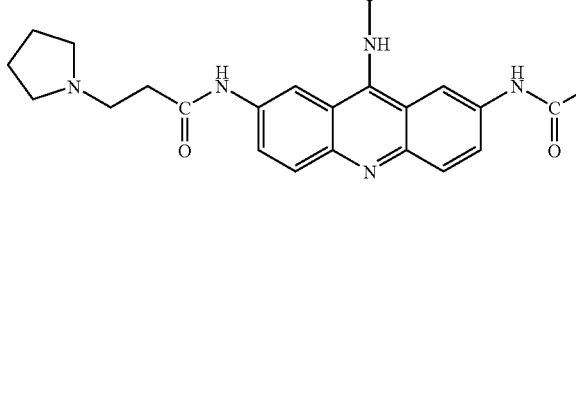 |

-continued

| Class | # Free Base HCl Salt | Structure |
|---|---|---|
| 2,7,9-ine | 17 JM-ACI-41 JM-ACI-42 | |
| 2,7,9-ine | 18 JM-ACI-45 JM-ACI-46 | |
| 2,7-one | 19 BR-ACO-16 BR-ACO-9 | |
| 2,7-one | 20 BR-ACO-17 BR-ACO-10 | |
| 2,7-one | 21 JH-ACO-23 JH-ACO-22 | |
| 2,7-one | 22 JH-ACO-27 JH-ACO-27 | |
| 2,7-one | 23 JM-ACO-06 JM-ACO-07 | |

-continued

| Class | # Free Base HCl Salt | Structure |
|---|---|---|
| 2,7-one | 24 JM-ACO-08 JM-ACO-09 | |
| 2,7-one | 25 JM-ACO-11 JM-ACO-12 | |
| 3,6,9-ine | 27 BR-ACO-21 BR-ACO-19 | |
| 3,6,9-ine | 27 BR-ACO-22 BR-ACO-20 | |
| 3,6,9-ine | 28 BSU-SB-36/152 SB-ACI-11 | |

| Class | # Free Base HCl Salt | Structure |
|---|---|---|
| 3,6,9-ine | 29 BSU-SB-36/158 SB-ACI-12 | |
| 3,6,9-ine | 30 BSU-SB-36/160 SB-ACI-13 | |
| 3,6,9-ine | 31 BSU-SB-36/164 SB-ACI-14 | |
| 3,6,9-ine | 32 JC-ACI-3A JC-ACI-3 | |

-continued

| Class | # Free Base HCl Salt | Structure |
|---|---|---|
| 3,6,9-ine | 33 JC-ACI-4A JC-ACI-4 | |
| 3,6,9-ine | 34 JC-ACI-5A JC-ACI-5 | |
| 3,6,9-ine | 35 JC-ACI-9A JC-ACI-9 | |
| 3,6,9-ine | 36 JH-ACI-100 JH-ACI-101 | |

-continued

| Class | # Free Base HCl Salt | Structure |
|---|---|---|
| 3,6,9-ine | 37<br>JH-ACI-102<br>JH-ACI-103 | |
| 3,6,9-ine | 38<br>JH-ACI-64<br>JH-ACI-65 | |
| 3,6,9-ine | 39<br>JH-ACI-68<br>JH-ACI-69 | |
| 3,6,9-ine | 40<br>JH-ACI-73<br>JH-ACI-74 | |

-continued

| Class | # Free Base HCl Salt | Structure |
|---|---|---|
| 3,6,9-ine | 41 JH-ACI-75 JH-ACI-76 | |
| 3,6,9-ine | 42 JH-ACI-77 JH-ACI-78 | |
| 3,6,9-ine | 43 JH-ACI-81 JH-ACI-82 | |
| 3,6,9-ine | 44 JH-ACI-85 JH-ACI-86 | |

-continued
| Class | # Free Base HCl Salt | Structure |
|---|---|---|
| 3,6,9-ine | 45 JH-ACI-87 JH-ACI-88 | 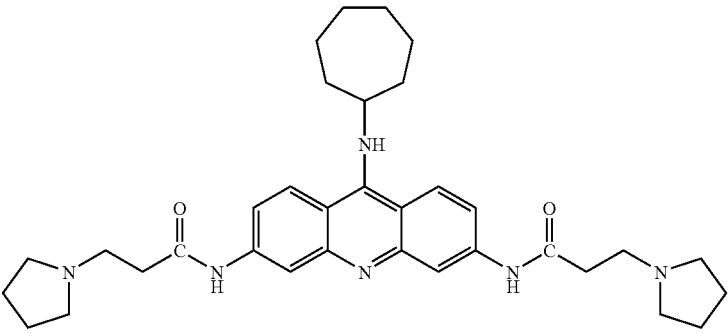 |
| 3,6,9-ine | 46 JH-ACI-89 JH-ACI-90 | 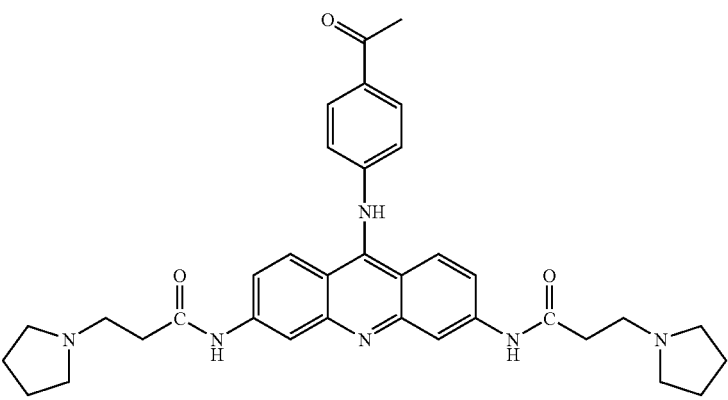 |
| 3,6,9-ine | 47 JM-ACI-13 JM-ACI-14 | 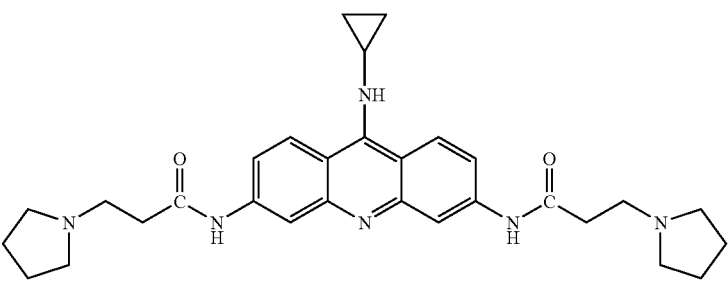 |
| 3,6-one | 48 BR-ACO-11 BR-ACO-6 | 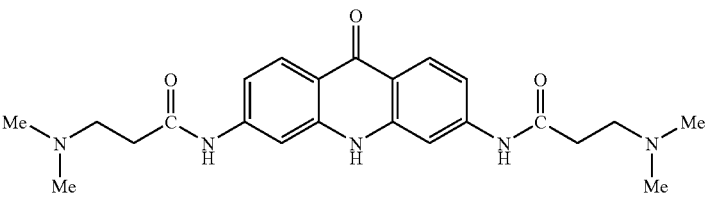 |
| 3,6-one | 49 BR-ACO-12 BR-ACO-7 | 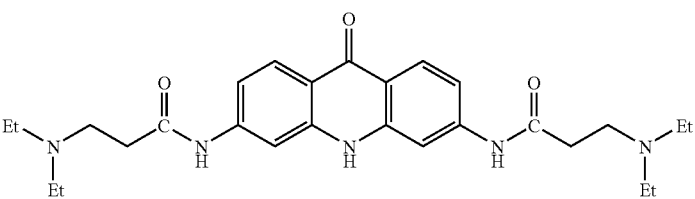 |

-continued
| Class | # Free Base HCl Salt | Structure |
|---|---|---|
| 3,6-one | 50<br>BR-ACO-13<br>BR-ACO-8 | 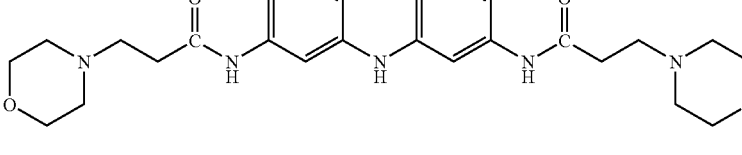 |
| 3,6-one | 51<br>BR-ACO-14<br>BR-ACO-4 | 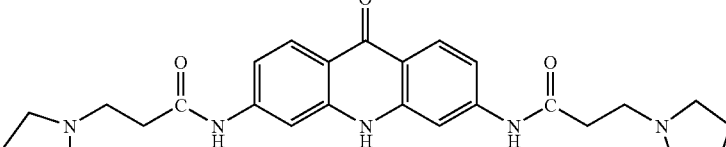 |
| 3,6-one | 52<br>BR-ACO-15<br>BR-ACO-5 | 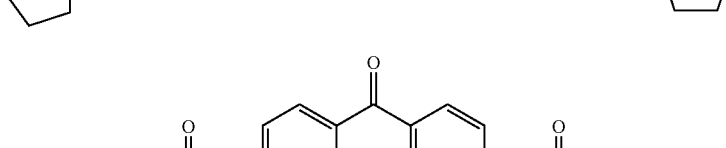 |
| 3,6-one | 53<br>BR-ACO-23<br>BR-ACO-33 | 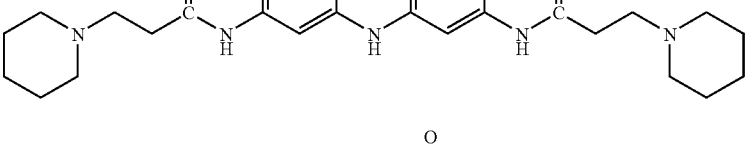 |
| 3,6-one | 54<br>BR-ACO-24<br>BR-ACO-34 | 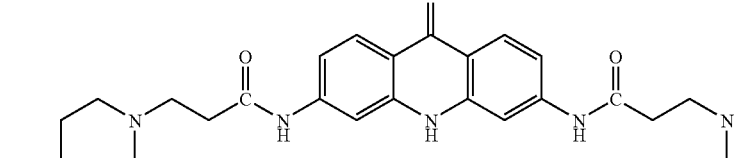 |
| 3,6-one | 55<br>BR-ACO-26<br>BR-ACO-36 | 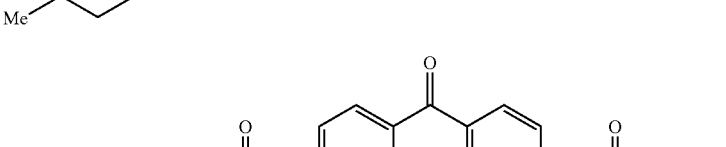 |
| 3,6-one | 56<br>BR-ACO-27<br>BR-ACO-37 | 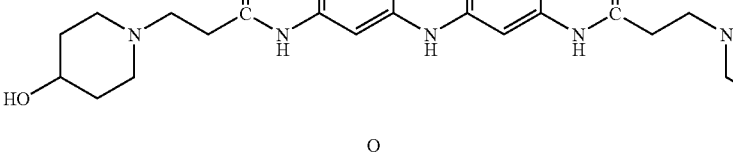 |

| Class | # Free Base HCl Salt | Structure |
|---|---|---|
| 3,6-one | 57 BR-ACO-29 BR-ACO-39 | |
| 3,6-one | 58 JH-ACO-31 JH-ACO-32 | |

Chemical Terms

The term "carbo," "carbyl," "hydrocarbon" and "hydrocarbyl," as used herein, pertain to compounds and/or groups which have only carbon and hydrogen atoms.

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, and sulfur, and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "ring," as used herein, pertains to a closed ring of from 3 to 10 covalently linked atoms, more preferably 3 to 8 covalently linked atoms.

The term "aromatic ring," as used herein, pertains to a closed ring of from 3 to 10 covalently linked atoms, more preferably 5 to 8 covalently linked atoms, which ring is aromatic.

The term "heterocyclic ring," as used herein, pertains to a closed ring of from 3 to 10 covalently linked atoms, more preferably 3 to 8 covalently linked atoms, wherein at least one of the ring atoms is a multivalent ring heteroatom, for example, nitrogen, phosphorus, silicon, oxygen, and sulfur, though more commonly nitrogen, oxygen, and sulfur.

The term "alicyclic," as used herein, pertains to compounds and/or groups which have one ring, or two or more rings (e.g., spiro, fused, bridged), wherein said ring(s) are not aromatic. The term "aromatic," as used herein, pertains to compounds and/or groups which have one ring, or two or more rings (e.g., fused), wherein said ring(s) are aromatic.

The term "heterocyclic," as used herein, pertains to cyclic compounds and/or groups which have one heterocyclic ring, or two or more heterocyclic rings (e.g., spiro, fused, bridged), wherein said ring(s) may be alicyclic or aromatic.

The term "heteroaromatic," as used herein, pertains to cyclic compounds and/or groups which have one heterocyclic ring, or two or more heterocyclic rings (e.g., fused), wherein said ring(s) is aromatic.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

In one preferred embodiment, the substituent(s), often referred to herein as R, are independently selected from: halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

In one preferred embodiment, the substituent(s), often referred to herein as R, are independently selected from:
—F, —Cl, —Br, and —I;
—OH;
—OMe, —OEt, —O(tBu), and —OCH$_2$Ph;
—SH;
—SMe, —SEt, —S(tBu), and —SCH$_2$Ph;
—C(=O)H;
—C(=O)Me, —C(=O)Et, —C(=O)(tBu), and —C(=O)Ph;
—C(=O)OH;
—C(=O)OMe, —C(=O)OEt, and —C(=O)O(tBu);
—C(=O)NH$_2$, —C(=O)NHMe, —C(=O)NMe$_2$, and —C(=O)NHEt;
—NHC(=O)Me, —NHC(=O)Et, —NHC(=O)Ph, succinimidyl, and maleimidyl;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
—CN;
—NO$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$;
—CH$_2$OH, —CH$_2$CH$_2$OH, and —CH(OH)CH$_2$OH;
—CH$_2$NH$_2$, —CH$_2$CH$_2$NH$_2$, and —CH$_2$CH$_2$NMe$_2$; and, optionally substituted phenyl.

In one preferred embodiment, the substituent(s), often referred to herein as R, are independently selected from:
—F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and —Ph.

In one preferred embodiment, the substituent(s), often referred to herein as R, are independently selected from: hydroxy; ether (e.g., C$_{1-7}$alkoxy); ester; amido; amino; and, C$_{1-7}$alkyl (including, e.g., C$_{1-7}$haloalkyl, C$_{1-7}$hydroxyalkyl, C$_{1-7}$carboxyalkyl, C$_{1-7}$aminoalkyl, C$_{5-20}$aryl-C$_{1-7}$alkyl).

In one preferred embodiment, the substituent(s), often referred to herein as R, are independently selected from:
—OH;
—OMe, —OEt, —O(tBu), and —OCH$_2$Ph;
—C(=O)OMe, —C(=O)OEt, and —C(=O)O(tBu);
—C(=O)NH$_2$, —C(=O)NHMe, —C(=O)NMe$_2$, and —C(=O)NHEt;
—NH$_2$, —NHMe, —NHEt, —NH(iPr), —NH(nPr), —NMe$_2$, —NEt$_2$, —N(iPr)$_2$, —N(nPr)$_2$, —N(nBu)$_2$, and —N(tBu)$_2$;
-Me, -Et, -nPr, -iPr, -nBu, -tBu;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$CH$_2$OH, and —CH(OH)CH$_2$OH; and,
—CH$_2$NH$_2$, —CH$_2$CH$_2$NH$_2$, and —CH$_2$CH$_2$NMe$_2$.

The substituents are described in more detail below.

C$_{1-7}$alkyl: The term "C$_{1-7}$alkyl," as used herein, pertains to a monovalent moiety obtained by removing a hydrogen atom from a C$_{1-7}$hydrocarbon compound having from 1 to 7 carbon atoms, which may be aliphatic or alicyclic, or a combination thereof, and which may be saturated, partially unsaturated, or fully unsaturated.

Examples of (unsubstituted) saturated linear C$_{1-7}$alkyl groups include, but are not limited to, methyl, ethyl, n-propyl, n-butyl, and n-pentyl (amyl).

Examples of (unsubstituted) saturated branched C$_{1-7}$alkyl groups include, but are not limited to, iso-propyl, iso-butyl, sec-butyl, tert-butyl, and neo-pentyl.

Examples of saturated alicyclic (carbocyclic) C$_{1-7}$alkyl groups (also referred to as "C$_{3-7}$cycloalkyl" groups) include, but are not limited to, unsubstituted groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl and cyclohexylmethyl.

Examples of (unsubstituted) unsaturated C$_{1-7}$alkyl groups which have one or more carbon-carbon double bonds (also referred to as "C$_{2-7}$alkenyl" groups) include, but are not limited to, ethenyl (vinyl, —CH=CH$_2$), 2-propenyl (allyl, —CH—CH=CH$_2$), isopropenyl (—C(CH$_3$)=CH$_2$), butenyl, pentenyl, and hexenyl.

Examples of (unsubstituted) unsaturated C$_{1-7}$alkyl groups which have one or more carbon-carbon triple bonds (also referred to as "C$_{2-7}$alkynyl" groups) include, but are not limited to, ethynyl (ethinyl) and 2-propynyl (propargyl).

Examples of unsaturated alicyclic (carbocyclic) C$_{1-7}$alkyl groups which have one or more carbon-carbon double bonds (also referred to as "C$_{3-7}$cycloalkenyl" groups) include, but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

C$_{3-20}$heterocyclyl: The term "C$_{3-20}$heterocyclyl," as used herein, pertains to a monovalent moiety obtained by removing a hydrogen atom from a ring atom of a C$_{3-20}$heterocyclic compound, said compound having one ring, or two or more rings (e.g., spiro, fused, bridged), and having from 3 to 20 ring atoms, atoms, of which from 1 to 10 are ring heteroatoms, and wherein at least one of said ring(s) is a heterocyclic ring. Preferably, each ring has from 3 to 7 ring atoms, of which from 1 to 4 are ring heteroatoms. "C$_{3-20}$" denotes ring atoms, whether carbon atoms or heteroatoms.

Examples of (non-aromatic) monocyclic heterocyclyl groups include, but are not limited to, those derived from:

N$_1$: aziridine (C$_3$), azetidine (C$_4$), pyrrolidine (tetrahydropyrrole) (C$_5$), pyrroline (e.g., 3-pyrroline, 2,5-dihydropyrrole) (C$_5$), 2H-pyrrole or 3H-pyrrole (isopyrrole, isoazole) (C$_5$), piperidine (C$_6$), dihydropyridine (C$_6$), tetrahydropyridine (C$_6$), azepine (C$_7$);

O$_1$: oxirane (C$_3$), oxetane (C$_4$), oxolane (tetrahydrofuran) (C$_5$), oxole (dihydrofuran) (C$_5$), oxane (tetrahydropyran) (C$_6$), dihydropyran (C$_6$), pyran (C$_6$), oxepin (C$_7$);

S$_1$: thiirane (C$_3$), thietane (C$_4$), thiolane (tetrahydrothiophene) (C$_5$), thiane (tetrahydrothiopyran) (C$_6$), thiepane (C$_7$);

O$_2$: dioxolane (C$_5$), dioxane (C$_6$), and dioxepane (C$_7$);

O$_3$: trioxane (C$_6$);

N$_2$: imidazolidine (C$_5$), pyrazolidine (diazolidine) (C$_5$), imidazoline (C$_5$), pyrazoline (dihydropyrazole) (C$_5$), piperazine (C$_6$);

N$_1$O$_1$: tetrahydrooxazole (C$_5$), dihydrooxazole (C$_5$), tetrahydroisoxazole (C$_5$), dihydroisoxazole (C$_5$), morpholine (C$_6$), tetrahydrooxazine (C$_6$), dihydrooxazine (C$_6$), oxazine (C$_6$);

N$_1$S$_1$: thiazoline (C$_5$), thiazolidine (C$_5$), thiomorpholine (C$_6$);

N$_2$O$_1$: oxadiazine (C$_6$);

O$_1$S$_1$: oxathiole (C$_5$) and oxathiane (thioxane) (C$_6$); and,

N$_1$O$_1$S$_1$: oxathiazine (C$_6$).

Examples of substituted (non-aromatic) monocyclic heterocyclyl groups include saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

$C_{5-20}$aryl: The term "$C_{5-20}$aryl," as used herein, pertains to a monovalent moiety obtained by removing a hydrogen atom from an aromatic ring atom of a $C_{5-20}$aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-7}$aryl, $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, including but not limited to oxygen, nitrogen, and sulfur, as in "heteroaryl groups." In this case, the group may conveniently be referred to as a "$C_{5-20}$heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of monocyclic heteroaryl groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_8$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), purine ($N_4$) (e.g., adenine, guanine), benzimidazole ($N_2$), benzoxazole ($N^1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from benzodioxan ($O_2$), quinoline ($N_1$), isoquinoline ($N_1$), benzoxazine ($N_1O_1$), benzodiazine ($N_2$), pyridopyridine ($N_2$), quinoxaline ($N_2$), quinazoline ($N_2$);

$C_{13}$heterocyclic groups (with 3 fused rings) derived from carbazole ($N_1$), dibenzofuran ($O_1$), dibenzothiophene ($S_1$); and, $C_{14}$heterocyclic groups (with 3 fused rings) derived from acridine ($N_1$), xanthene ($O_1$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:

$C_9$: indenedione;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$);
$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$);

cyclic ureas (—NR—C(=O)—NR— in a ring), such as 2-imidazolidone ($C_5$) and pyrimidine-2,4-dione (e.g., thymine, uracil) ($C_6$).

The above $C_{1-7}$alkyl, $C_{3-20}$heterocyclyl, and $C_{5-20}$aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$hetercyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OCH$_3$ (methoxy), —OCH$_2$CH$_3$ (ethoxy) and —OC(CH$_3$)$_3$ (tert-butoxy).

Oxo (keto, -one): =O. Examples of cyclic compounds and/or groups having, as a substituent, an oxo group (=O) include, but are not limited to, carbocyclics such as cyclopentanone and cyclohexanone; heterocyclics, such as pyrone, pyrrolidone, pyrazolone, pyrazolinone, piperidone, piperidinedione, piperazinedione, and imidazolidone; cyclic anhydrides, including but not limited to maleic anhydride and succinic anhydride; cyclic carbonates, such as propylene carbonate; imides, including but not limited to, succinimide and maleimide; lactones (cyclic esters, —O—C(=O)— in a ring), including, but not limited to, β-propiolactone, γ-butyrolactone, δ-valerolactone, and ε-caprolactone; and lactams (cyclic amides, —NH—C(=O)— in a ring), including, but not limited to, β-propiolactam, γ-butyrolactam, δ-valerolactam, and ε-caprolactam.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (butyryl), and —C(=O)Ph (benzoyl, phenone).

Acylhalide (haloformyl, halocarbonyl): —C(=O)X, wherein X is —F, —Cl, —Br, or —I, preferably —Cl, —Br, or —I.

Carboxy (carboxylic acid): —COOH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)NH(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein R$^1$ is an amide substituent, for example, a $C_{1-7}$alkyl group, a $C_{3-20}$heterocyclyl group, or a $C_{5-20}$aryl group, preferably a $C_{1-7}$alkyl group, and R$^2$ is an acyl substituent, for example, a $C_{1-7}$alkyl group, a $C_{3-20}$heterocyclyl group, or a $C_{5-20}$aryl group, preferably a $C_{1-7}$alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

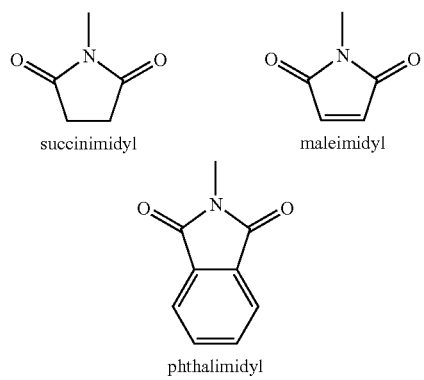

succinimidyl      maleimidyl phthalimidyl

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)NH(CH$_3$)$_2$, and —C(=S)NHCH$_2$CH$_3$.

Tetrazolyl: a five membered aromatic ring having four nitrogen atoms and one carbon atom,

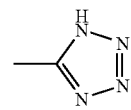

Amino: —NR$^1$R$^2$, wherein R$^1$ and R$^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —NH$_2$, —NHCH$_3$, —NHCH(CH$_3$)$_2$, —N(CH$_3$)$_2$, —N(CH$_2$CH$_3$)$_2$, and —NHPh. Examples of cyclic amino groups include, but are not limited to, aziridino, azetidino, piperidino, piperazino, morpholino, and thiomorpholino.

Nitro: —NO$_2$.
Nitroso: —NO.
Azido: —N$_3$.
Cyano (nitrile, carbonitrile): —CN.
Isocyano: —NC.
Cyanato: —OCN.
Isocyanato: —NCO.
Thiocyano (thiocyanato): —SCN.
Isothiocyano (isothiocyanato): —NCS.
Sulfhydryl (thiol, mercapto): —SH.
Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH$_3$ and —SCH$_2$CH$_3$.
Sulfonic acid (sulfo): —S(=O)$_2$OH.
Sulfonate (sulfonic acid ester): —S(=O)$_2$OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)$_2$OCH$_3$ and —S(=O)$_2$OCH$_2$CH$_3$.
Sulfone (sulfonyl): —S(=O)$_2$R, wherein R is a sulfone substituent, for example, a $C_{1-7}$alkyl group, a $C_{3-20}$heterocyclyl group, or a $C_{5-20}$aryl group, preferably a $C_{1-7}$alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).
Sulfonyloxy: —OS(=O)$_2$R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)$_2$CH$_3$ and —OS(=O)$_2$CH$_2$CH$_3$.
Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH$_3$ and —OS(=O)CH$_2$CH$_3$.
Sulfamino: —NR$^1$S(=O)$_2$OH, wherein $R^1$ is an amino substituent, as defined for amino groups. Examples of sulfamino groups include, but are not limited to, —NHS(=O)$_2$OH and —N(CH$_3$)S(=O)$_2$OH.
Sulfonamino: —NR$^1$S(=O)$_2$R, wherein $R^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$ and —N(CH$_3$)S(=O)$_2$C$_6$H$_5$.
Sulfinamino: —NR$^1$S(=O)R, wherein $R^1$ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH$_3$ and —N(CH$_3$)S(=O)C$_6$H$_5$.
Sulfamyl: —S(=O)NR$^1$R$^2$, wherein $R^1$ and $R^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.
Sulfonamido: —S(=O)$_2$NR$^1$R$^2$, wherein $R^1$ and $R^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

As mentioned above, a $C_{1-7}$alkyl group may be substituted with, for example, hydroxy (also referred to as a $C_{1-7}$hydroxyalkyl group), $C_{1-7}$alkoxy (also referred to as a $C_{1-7}$alkoxyalkyl group), amino (also referred to as a $C_{1-7}$aminoalkyl group), halo (also referred to as a $C_{1-7}$haloalkyl group), carboxy (also referred to as a $C_{1-7}$carboxyalkyl group), and $C_{5-20}$aryl (also referred to as a $C_{5-20}$aryl-$C_{1-7}$alkyl group).

Similarly, a $C_{5-20}$aryl group may be substituted with, for example, hydroxy (also referred to as a $C_{5-20}$hydroxyaryl group), halo (also referred to as a $C_{5-20}$haloaryl group), amino (also referred to as a $C_{5-20}$aminoaryl group, e.g., as in aniline), $C_{1-7}$alkyl (also referred to as a $C_{1-7}$alkyl-$C_{5-20}$aryl group, e.g., as in toluene), and $C_{1-7}$alkoxy (also referred to as a $C_{1-7}$alkoxy-$C_{5-20}$aryl group, e.g., as in anisole).

These and other specific examples of such substituted groups are also discussed below.

$C_{1-7}$haloalkyl group: The term "$C_{1-7}$haloalkyl group," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$perhaloalkyl group." Examples of $C_{1-7}$haloalkyl groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

$C_{1-7}$hydroxyalkyl: The term "$C_{1-7}$hydroxyalkyl group," as used herein, pertains to a $C_{1-7}$alkyl group in which at least one hydrogen atom has been replaced with a hydroxy group. Examples of $C_{1-7}$hydroxyalkyl groups include, but are not limited to, —CH$_2$OH, —CH$_2$CH$_2$OH, and —CH(OH)CH$_2$OH.

$C_{1-7}$carboxyalkyl: The term "$C_{1-7}$carboxyalkyl group," as used herein, pertains to a $C_{1-7}$alkyl group in which at least one hydrogen atom has been replaced with a carboxy group. Examples of $C_{1-7}$carboxyalkyl groups include, but are not limited to, —CH$_2$COOH and —CH$_2$CH$_2$COOH.

$C_{1-7}$aminoalkyl: The term "$C_{1-7}$aminoalkyl group," as used herein, pertains to a $C_{1-7}$alkyl group in which at least one hydrogen atom has been replaced with an amino group. Examples of $C_{1-7}$aminoalkyl groups include, but are not limited to, —CH$_2$NH$_2$, —CH$_2$CH$_2$NH$_2$, and —CH$_2$CH$_2$N(CH$_3$)$_2$.

$C_{1-7}$alkyl-$C_{5-20}$aryl: The term "$C_{1-7}$alkyl-$C_{5-20}$aryl," as used herein, describes certain $C_{5-20}$aryl groups which have been substituted with a $C_{1-7}$alkyl group. Examples of such groups include, but are not limited to, tolyl (as in toluene), xylyl (as in xylene), mesityl (as in mesitylene), styryl (as in styrene), and cumenyl (as in cumene).

C$_{5-20}$aryl-C$_{1-7}$alkyl: The term "C$_{5-20}$aryl-C$_{1-7}$alkyl," as used herein, describers certain C$_{1-7}$alkyl groups which have been substituted with a C$_{5-20}$aryl group. Examples of such groups include, but are not limited to, benzyl (phenylmethyl), tolylmethyl, phenylethyl, and triphenylmethyl (trityl).

C$_{5-20}$haloaryl: The term "C$_{5-20}$haloaryl," as used herein, describes certain C$_{5-20}$aryl groups which have been substituted with one or more halo groups. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (iPrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), 4-(dimethyamino)pyridine (DMAP), tetrahydrofuran (THF), and dimethylsulfoxide (DMSO).

Isomers, Salts, Solvates, Protected Forms, and Prodrugs

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r- forms; endo- and exo-forms; R-, S-, and meso-forms; D- and L-forms: d- and I-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl.

However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amidelimino alcohol, amidine/amidine, nitroso/oxime, thioketone/enethiol, N-nitroso/hyroxyazo, and nitro/aci-nitro.

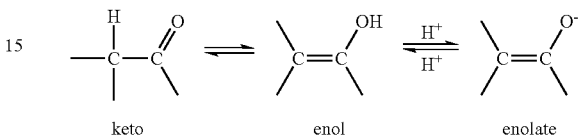

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt.

Examples of pharmaceutically acceptable salts are discussed in Berge et al., 1977, "Pharmaceutically Acceptable Salts," J. Pharm. Sci., Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na+ and K+, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicylic, sulfanilic, 2-acetyoxybenzoic, fumaric, toluenesulfonic, methanesulfonic, ethane disulfonic, oxalic, isethionic, and valeric. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts, Wiley, 1991).

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyidimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO—).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide; for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include those wherein R is C$_{1-7}$alkyl (e.g., -Me, -Et); C$_{1-7}$aminoalkyl (e.g., aminoethyl; 2-(N,N-diethylamino)ethyl; 2-(4-morpholino)ethyl); and acyloxy-C$_{1-7}$alkyl (e.g., acyloxymethyl; acyloxyethyl; e.g., pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Synthesis

The acridone and acridine compounds of the present invention may be prepared, for example, by the methods illustrated in FIGS. 1, 2, 3A, 3B, 4, 5, and 6, or by adapting these or other well known methods in well known ways.

FIG. 1 is a scheme illustrating a chemical synthesis method for certain 3,6-disubstituted acridones of the present invention. The reagents/conditions for the steps in FIG. 1 are: (i) KNO$_3$/H$_2$SO$_4$; (ii) CrO$_3$, AcOH, reflux; (iii) SnCl$_2$/HCl, 90-100° C.; (iv) 3-chloropropionyl chloride (3-CPC), reflux; (v) NHR$^1$R$^2$, EtOH, NaI, reflux; and, (vi) HCl. By using appropriate 1° or 2° amines, NHR$^1$R$^2$, preferably 2° amines, different acridones of the present invention are obtained.

Figure 2:
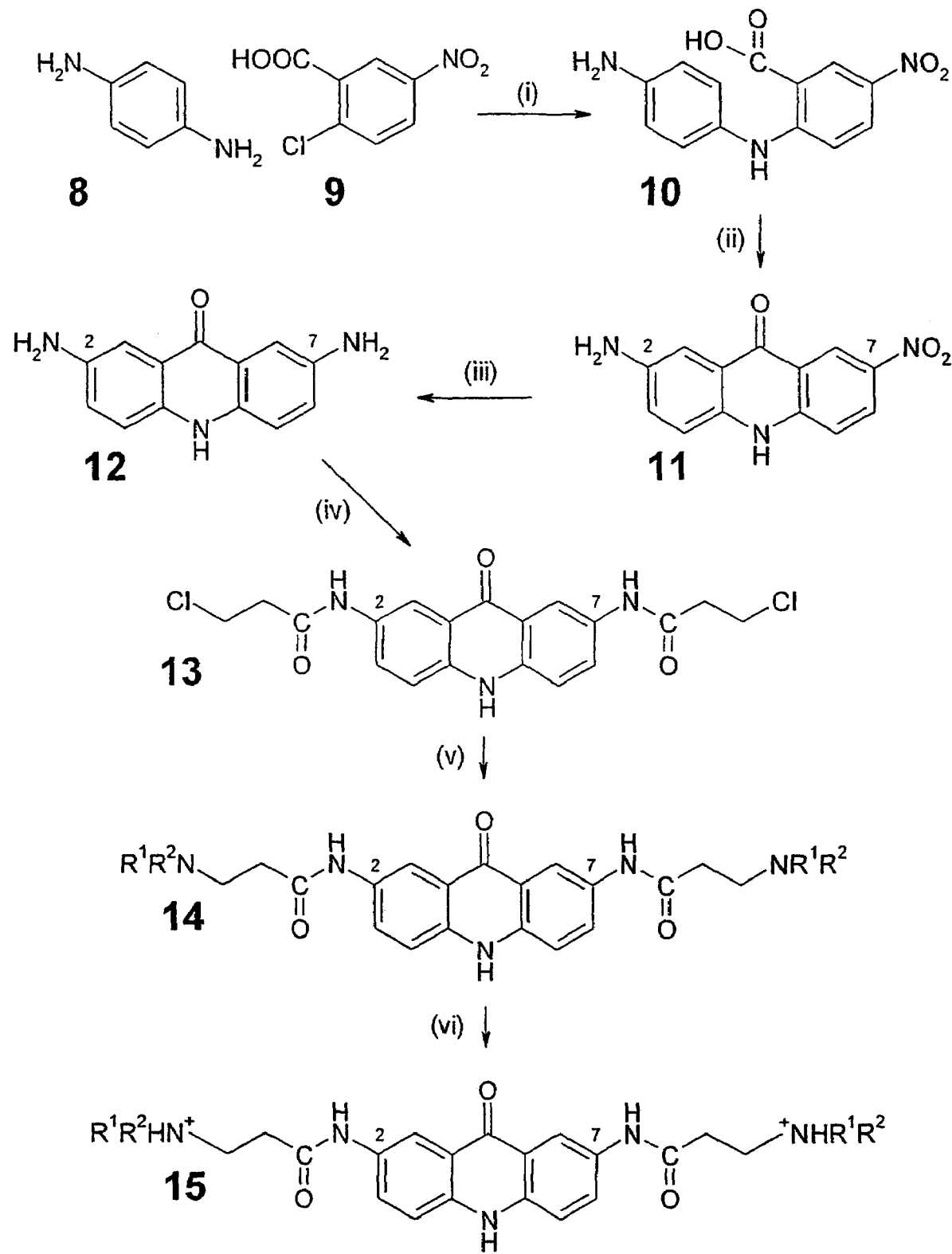
FIG. 2 is a scheme illustrating a chemical synthesis method for certain 2,7-disubstituted acridones of the present invention.

FIG. 2 is a scheme illustrating a chemical synthesis method for certain 2,7-disubstituted acridones of the present invention. The reagents/conditions for the steps in FIG. 2 are: (i) Cu/CuSO$_4$/K$_2$CO$_3$/H$_2$O, 5 hrs reflux; (ii) polyphosphoric acid (PPA), 100° C., 5 hr; (iii) Na$_2$S, NaOH, EtOH, H$_2$O, reflux; (iv) 3-chloropropionyl chloride (3-CPC), reflux; (v) NHR$^1$R$^2$, EtOH, NaI; and (vi) HCl. By using appropriate 1° or 2° amines, NHR$^1$R$^2$, preferably 2° amines, different acridones of the present invention are obtained.

Figure 3A:
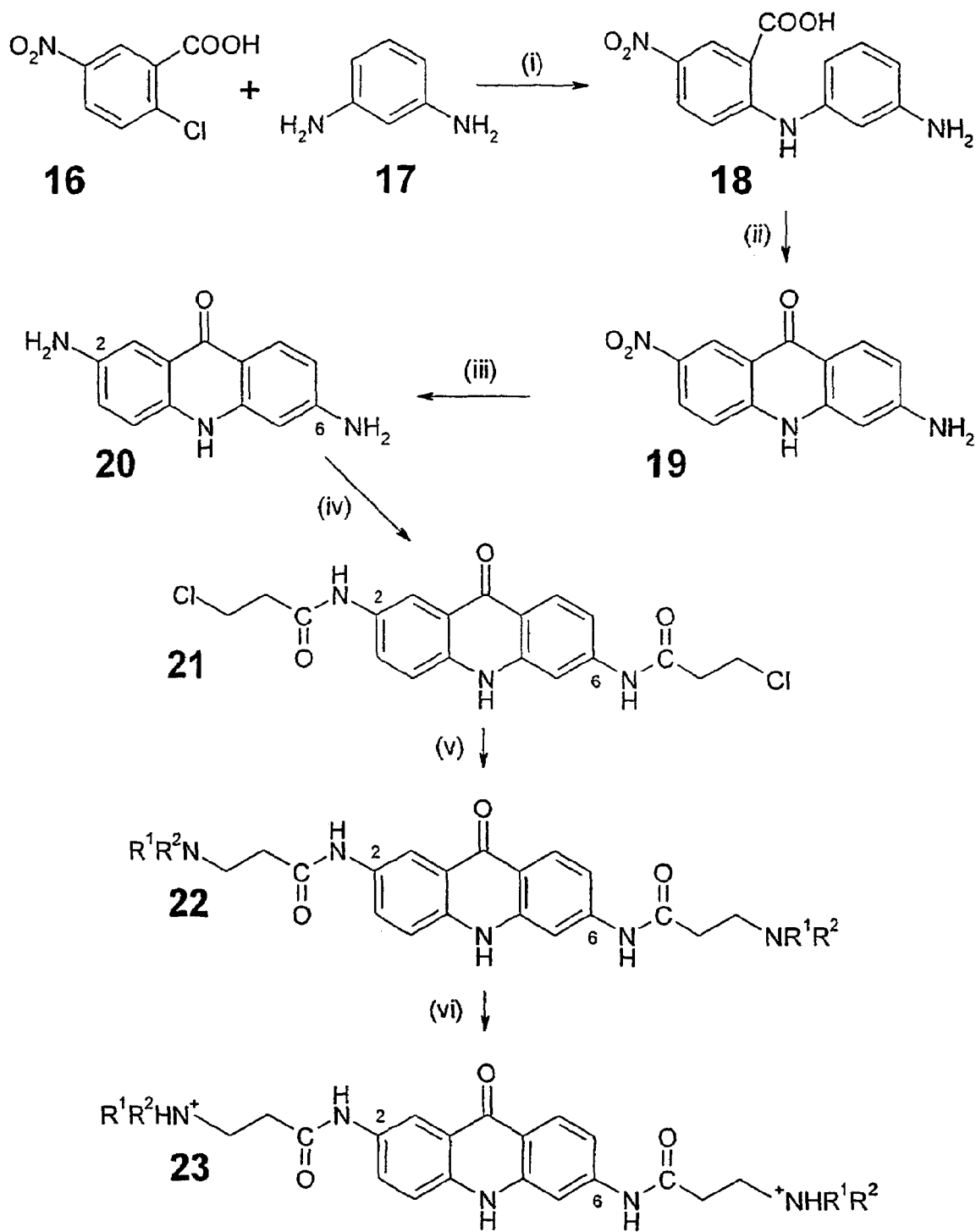
FIG. 3A is a scheme illustrating a chemical synthesis method for certain 2,6-disubstituted acridones of the present invention.

FIG. 3A is a scheme illustrating a chemical synthesis method for certain 2,6-disubstituted acridones of the present invention. The reagents/conditions for the steps in FIG. 3A are: (i) Cu, CuSO$_4$, K$_2$CO$_3$, H$_2$O; (ii) H$_2$SO$_4$, H$_2$O; (iii) Na$_2$S, NaOH; (iv) 3-chloroproponylchloride; (v) EtOH, KI, NHR$^1$R$^2$; and, (vi) HCl. By using appropriate 1° or 2° amines, NHR$^1$R$^2$, preferably 2° amines, different acridones of the present invention are obtained.

Figure 3B:
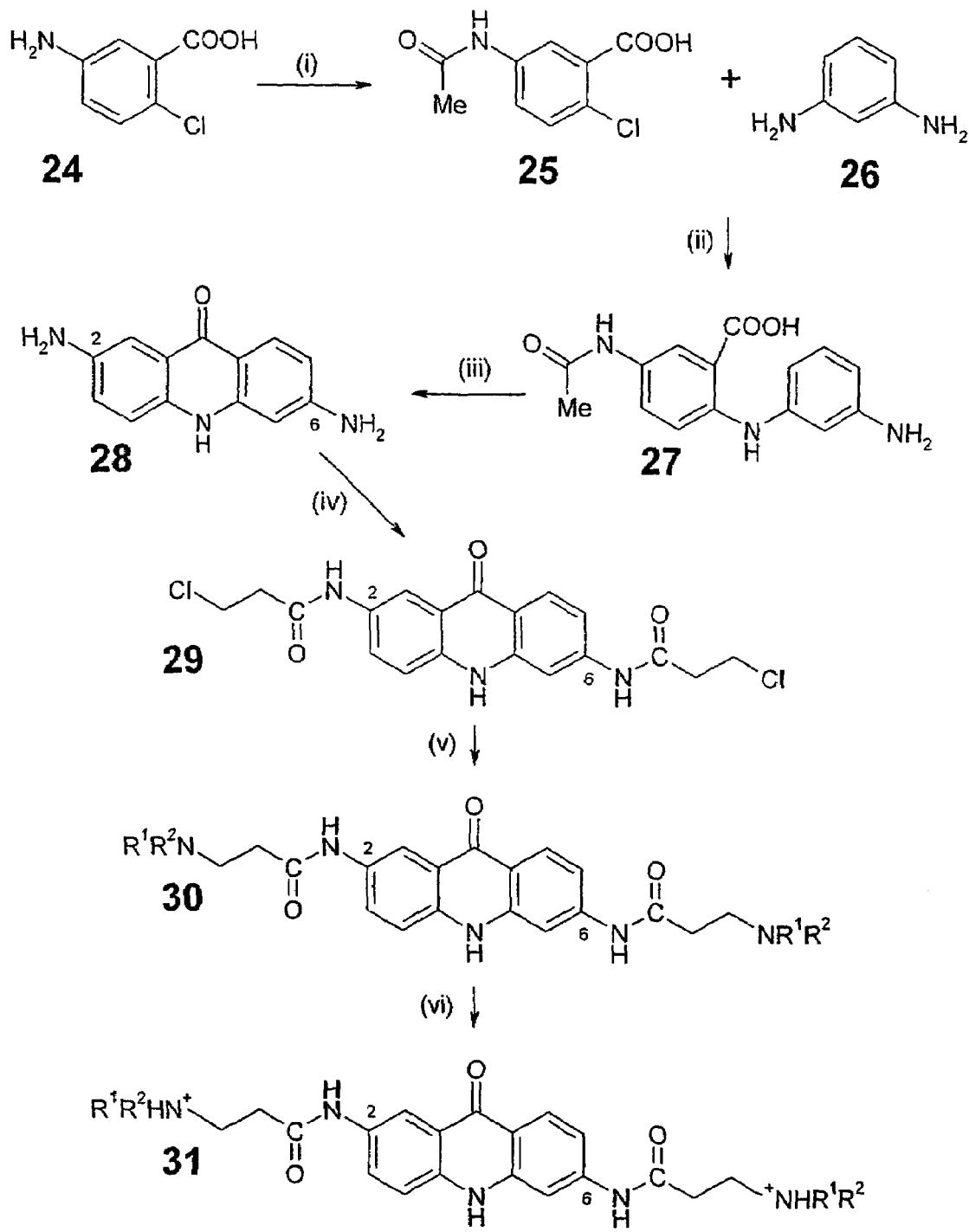
FIG. 3B is another scheme illustrating a chemical synthesis method for certain 2,6-disubstituted acridones of the present invention.

FIG. 3B is a scheme illustrating a chemical synthesis method for certain 2,6-dissubstituted acridones of the present invention. The reagents/conditions for the steps in FIG. 3B are: (i) acetic anhydride, $H_2O$, $Na_2CO_3$; (ii) pentan-1-ol, $KCO_3$, Cu; (iii) $H_2SO_4$, $H_2O$; (iv) 3-chloroproponyl-chloride; (v) EtOH, KI, $NHR^1R^2$; and, (vi) HCl. By using appropriate 1° or 2° amines, $NHR^1R^2$, preferably 2° amines, different acridones of the present invention are obtained.

Figure 4:
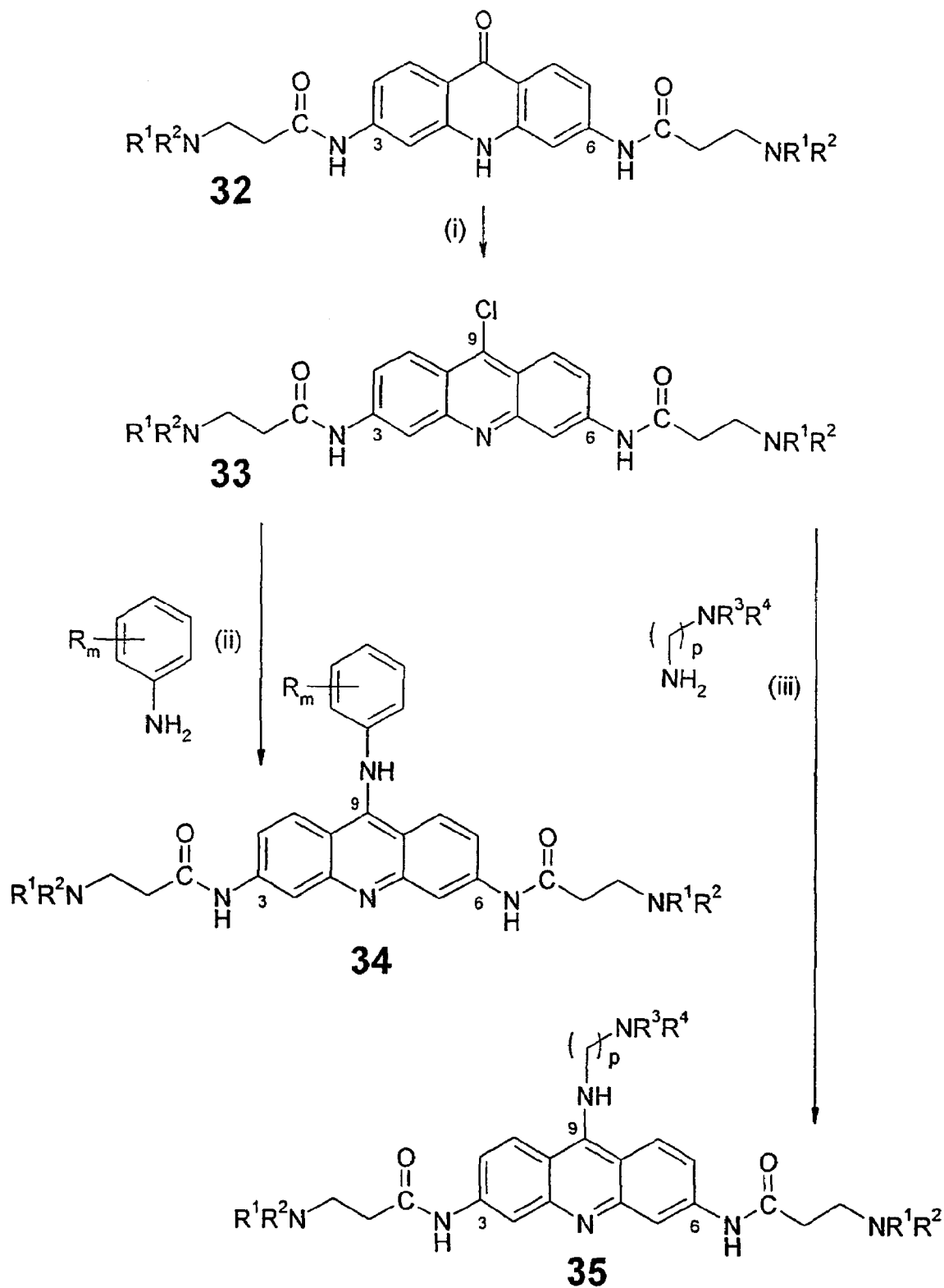
FIG. 4 is a scheme illustrating a chemical synthesis method for certain 3,6,9-trisubstituted acridines of the present invention.

FIG. 4 is a scheme illustrating a chemical synthesis method for certain 3,6,9-trisubstituted acridines of the present invention. The reagents/conditions for the steps in FIG. 4 are: (i) $POCl_3$, reflux; (ii) $H_2N(PhR_m)$, $CHCl_3$, RT; and, (iii) $NH_2(CH_2)_pNH_2$, MeOH. By using appropriate 1° or 2° amines, $NHR^1R^2$, preferably 2° amines, and appropriate amines, $Q-NHR^N$ (e.g., $NH_2(CH_2)_pNH_2$, substituted anilines, etc.), different acridines of the present invention are obtained.

Figure 5:
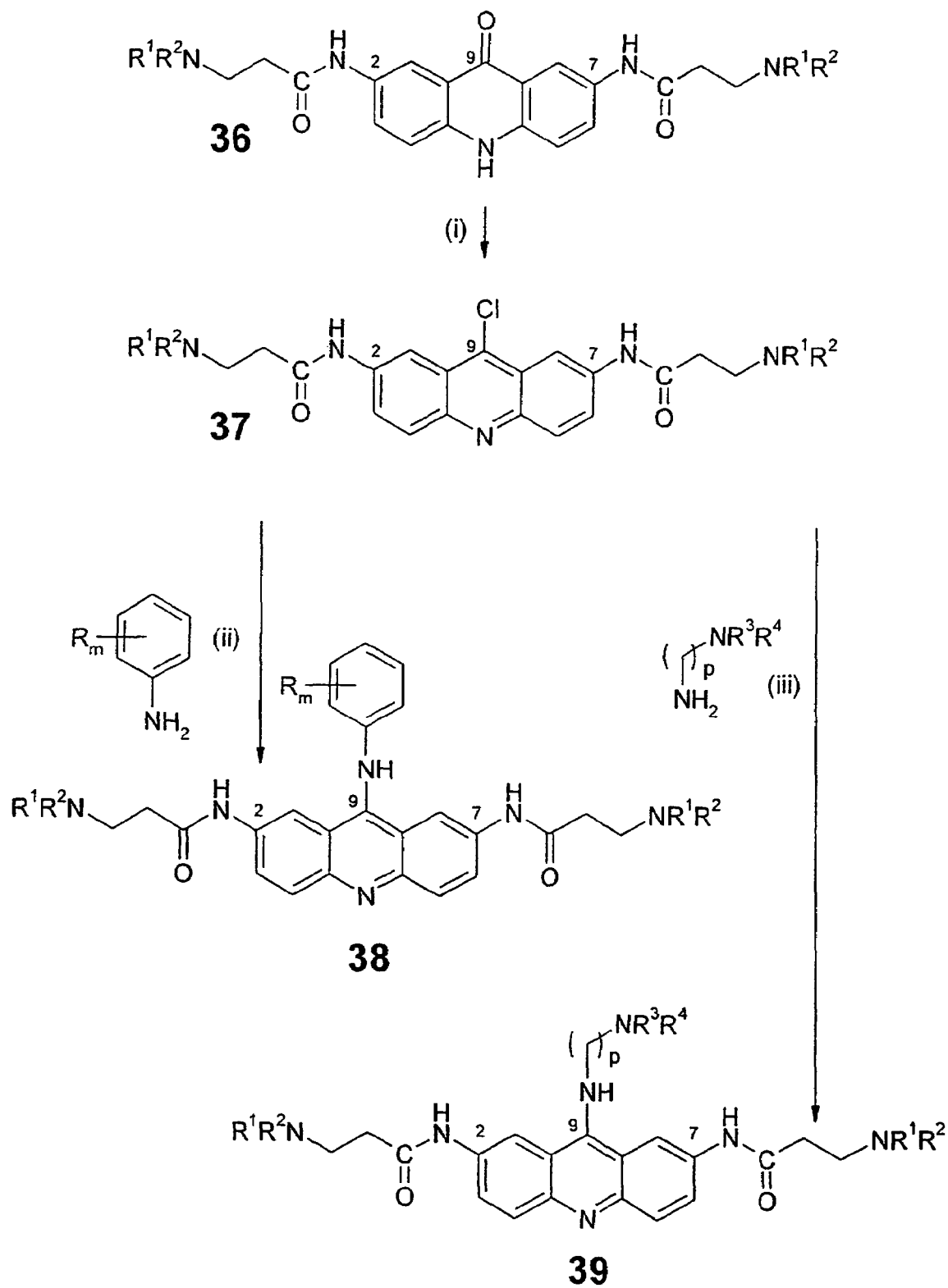
FIG. 5 is a scheme illustrating a chemical synthesis method for certain 2,7,9-trisubstituted acridines of the present invention.

FIG. 5 is a scheme illustrating a chemical synthesis method for certain 2,7,9-trisubstituted acridines of the present invention. The reagents/conditions for the steps in FIG. 5 are: (i) $POCl_3$, reflux; (ii) $H_2N(PhR_m)$, $CHCl_3$, RT; and, (iii) $NH_2(CH_2)_pNH_2$, MeOH. By using appropriate 1° or 2° amines, $NHR^1R^2$, preferably 2° amines, and appropriate amines, $Q-NHR^N$ (e.g., $NH_2(CH_2)_pNH_2$, substituted anilines, etc.), different acridines of the present invention are obtained.

Figure 6:
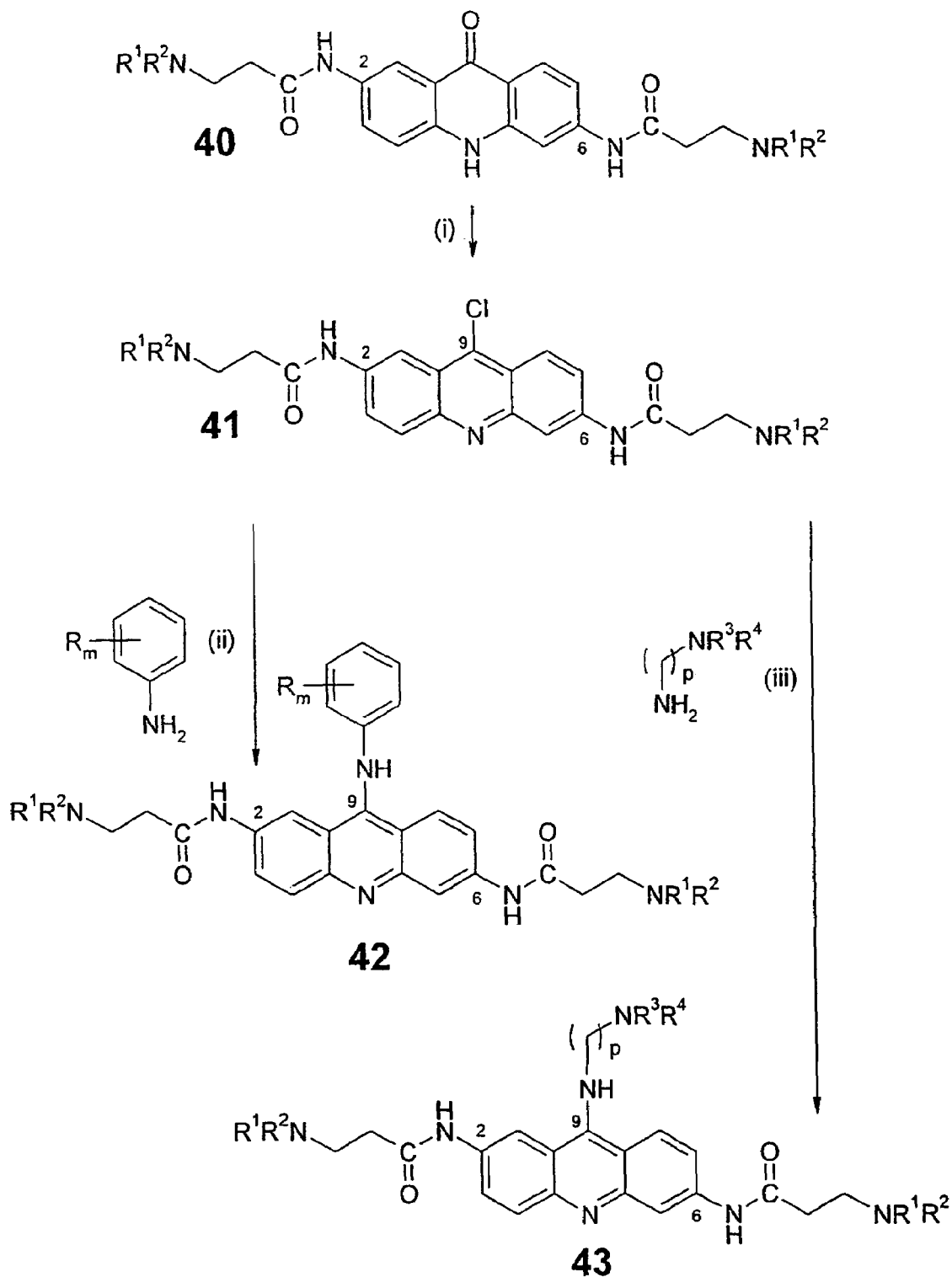
FIG. 6 is a scheme illustrating a chemical synthesis method for certain 2,6,9-trisubstituted acridines of the present invention.

FIG. 6 is a scheme illustrating a chemical synthesis method for certain 2,6,9-trisubstituted acridines of the present invention. The reagents/conditions for the steps in FIG. 6 are: (i) $POCl_3$, reflux; (ii) $H_2N(PhR_m)$, $CHCl_3$, RT; and, (iii) $NH_2(CH_2)_pNH_2$, MeOH. By using appropriate 1° or 2° amines, $NHR^1R^2$, preferably 2° amines, and appropriate amines, $Q-NHR^N$ (e.g., $NH_2(CH_2)_pNH_2$, substituted anilines, etc.), different acridines of the present invention are obtained.

Additional relevant synthesis methods are described in, for example, Matsumura, 1929 and Korolev et al., 1977, and the references cited therein.

Uses

The present invention provides active compounds, specifically, active acridines and acridones, as described herein. The term "active," as used herein, pertains to compounds which are capable of inhibiting telomerase and/or of regulating cell proliferation.

One of ordinary skill in the art is readily able to determine whether or not a candidate compound inhibits telomerase activity. For example, one assay which may conveniently be used in order to assess the telomerase inhibition offered by a particular compound is described in the examples below.

Thus, the present invention provides active compounds which inhibit telomerase, as well as methods of inhibiting telomerase, comprising contacting a cell with an effective amount of an active compound, preferably in the form of a pharmaceutically acceptable composition. Such a method may be practised in vitro or in vivo.

The present invention further provides active compounds which regulate cell proliferation, as well as methods of regulating cell proliferation, comprising contacting a cell with an effective amount of an active compound, preferably in the form of a pharmaceutically acceptable composition. Such a method may be practised in vitro or in vivo.

For example, a sample of cells (e.g., from a tumour) may be grown in vitro and an active compound brought into contact with said cells, and the effect of the compound on those cells observed. As examples of "effect," the morphological status of the cells may be determined, or the expression levels of genes associated with cell cycle regulation determined. Where the active compound is found to exert an influence on the cells, this may be used as a prognostic or diagnostic marker of the efficacy of the compound in methods of treating a patient carrying cells of the same cellular type.

One of ordinary skill in the art is readily able to determine whether or not a candidate compound regulates cell proliferation for any particular cell line. For example, one assay which may conveniently be used to assess the activity offered by a particular compound is described in the examples below.

The present invention further provides active compounds which are antiproliferative agents. The term "antiproliferative agent" as used herein, pertain to a compound which treats a proliferative condition (i.e., a compound which is useful in the treatment of a proliferative condition).

One of ordinary skill in the art is readily able to determine whether or not a candidate compound treats a proliferative condition for any particular cell line. For example, one assay which may conveniently be used to assess the activity offered by a particular compound is described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., ovarian carcinoma, breast carinoma, bowel cancer, colon cancer, renal cancer, lung cancer, small cell lung cancer, testicular cancer, prostate cancer, sarcoma, osteosarcoma, Kaposi's sarcoma, melanoma), leukemias, psoriasis, bone diseases, fibroproliferative disorders (e.g., of connective tissues), and atherosclerosis. Any type of cell may be treated, including but not limited to, colon, kidney (renal), breast (mammary), lung, ovarian, liver (hepatic), pancreas, skin, and brain.

Antiproliferative compounds of the present invention have application in the treatment of cancer, and so the present invention further provides anticancer agents. The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The invention further provides active compounds for use in a method of treatment of the human or animal body, for example, in the treatment of a proliferative condition, for example cancer. Such a method may comprise administering to such a subject a therapeutically-effective amount of an active compound, preferably in the form of a pharmaceutical composition.

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

The invention further provides the use of an active compound for the manufacture of a medicament, for example, for the treatment of a proliferative condition.

The invention further provides a method of treatment of the human or animal body, the method comprising administering to a subject in need of treatment a therapeutically-effective amount of an active compound, preferably in the form of a pharmaceutical composition.

Active compounds may also be used as cell culture additives to inhibit telomerase, for example, in order to regulate cell proliferation in vitro.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other telomerase inhibitors, other antiproliferative agents, etc.

Kits

One aspect of the invention pertains to a kit comprising (a) the active ingredient, preferably provided in a suitable container and/or with suitable packaging; and (b) instructions for use, for example, written instructions on how to administer the active compound.

The written instructions may also include a list of indications for which the active ingredient is a suitable treatment.

Administration

The active compound or pharmaceutical composition comprising the active compound may be administered to a subject by any convenient route of administration, whether systemically/peripherally or at the site of desired action, including but not limited to, oral (e.g, by ingestion); topical (including e.g., transdermal, intranasal, ocular, buccal, and sublingual); pulmonary (e.g., by inhalation or insufflation therapy using, e.g., an aerosol, e.g., through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), an ape (e.g., gorilla, chimpanzee, orangutang, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, excipients, buffers, adjuvants, stabilisers, or other materials well known to those skilled in the art and optionally other therapeutic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, tablets, losenges, granules, powders, capsules, cachets, pills, ampoules, suppositories, pessaries, ointments, gels, pastes, creams, sprays, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by compression or molding, optionally with one or more accessory ingredients. Compressed tablets may be prepared by compressing in a suitable machine the active compound in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose), surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low.

Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect.

Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 0.1 to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

General Procedures

Melting points (mp) were recorded on a Leica Galen III hot-stage melting point apparatus and are uncorrected. $^1$H-NMR spectra were recorded at 250 MHz on a Bruker AC250 spectrometer in either $d_6$-Me$_2$SO or CDCl$_3$ solution at 303±1 K using Me$_4$Si (TMS) as internal standard. EI (70 eV), FAB and high resolution accurate mass spectra were determined by The School of Pharmacy (University of London, UK). Elemental analyses were carried out by Medac Ltd. (Brunel Science Center, Egham, Surrey, UK); results for elements indicated by symbols were within 0.4% of theoretical values. TLC was carried out on silica gel (Merck 60F-254) using CHCl$_3$/MeOH (0-20% MeOH) as eluent, with visualization at 254 and 366 nm. Organic solutions were dried over sodium sulphate.

Example 1

2,2',4,4'-Tetranitrodiphenylmethane (2)

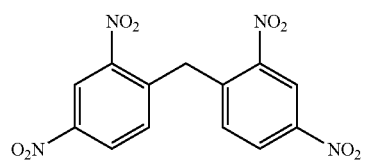

Potassium nitrate (54.00 g, 0.53 mol) was added in portions to stirred concentrated H$_2$SO$_4$ (200 mL) whilst maintaining the temperature below 20° C. Diphenylmethane 1 (20.00 g, 0.12 mol) was added dropwise over 1.5 hr at 15° C. to give a brown mixture. Upon complete addition the mixture was heated to 70° C. for 40 min and produced a deep red solution. On cooling, the liquor was poured into ice and the light brown solid produced collected. This solid was washed with H$_2$O (2×200 mL) and boiled with EtOH (300 mL) to afford the product 2 (33.83 g, 82%) as a cream solid.

Mp 170-173° C. (lit. 173° C.); $^1$H-NMR (CDCl$_3$) δ 4.87 (s, 2H, CH$_2$), 7.41 (D, $^3$J=8.5 Hz, 2H, H-6/6'), 8.44 (dd, $^3$J=8.5 Hz, $^4$J=2.4 Hz, 2H, H-5/5'), 8.97 (d, $^4$J=2.4 Hz, 2H, H-3/3'); MS [EI] (relative intensity %) m/z 346 ([M]$^{.+}$, 41), 331 (48), 303 (57), 302 ([M–NO$_2$]$^{.+}$, 38), 300 (41), 268 (60), 285 (37), 256 ([M–N$_2$O$_4$]$^{.+}$, 19), 255 (29), 254 (64), 253 (24), 240 (32), 239 (100), 210 ([M–N3O6].+, 62), 193 (42), 164 ([M–N$_4$O$_8$]$^{.+}$, 46), 163 (80), C$_{13}$H$_8$N$_4$O$_8$ (M=348.24) Found: C, 44.54; H, 2.38; N, 15.96%. requires C, 44.84; H, 231; N, 16.09%.

Example 2

2,2',4,4'-Tetranitrobenzophenone (3) (BR-ACO-1)

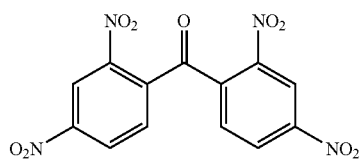

To a refluxing solution of 2 (68.00 g, 0.20 mol) in glacial AcOH (100 mL) was slowly added CrO$_3$ (100.00 g, 1.00 mol) during 45 min, and the mixture refluxed for 3 hr. On cooling, the product was poured into water (3000 mL) and the resultant precipitate collected, washed with H$_2$O (2000 nmL), EtOH (2×100 mL) and Et$_2$O (2×100 mL) to furnish the ketone 3 (66.40 g, 94%) as a cream solid.

Mp 236-238° C. (lit. 232° C.; Matsumura, 1929); $^1$H-NMR (d$_6$-DMSO) δ 8.03 (d, $^3$J=2.0 Hz, 2H, H-6/6'), 8.65 (dd, $^3$J=8.5 Hz, $^4$J=2.1 Hz, 2H, H-5/5'), 8.96 (d, $^4$J=2.1 Hz, 2H H-3/3'); MS [EI] (relative intensity %) m/z 363 ([M+H] $^{.+}$, 6%), 346 ([M–O]. $^{.+}$, 52), 316 ([M–NO$_2$]$^{.+}$, 100), 270 (28), 242 (16), 196 ([C$_7$H$_4$N$_2$O$_5$]$^{.+}$, 54), 195 ([C$_7$H$_3$N$_2$O$_5$]$^{.+}$, 100) 179 ([C$_7$H$_4$N$_2$O$_4$]$^{.+}$, 71), 149 ([C$_7$H$_3$NO$_3$]$^{.+}$, 85), 103 ([C$_7$H$_3$O]$^{.+}$, 82), 75 ([C$_6$H$_3$]$^{.+}$, 100). Found C, 43.13; H, 1.52; N, 15.38%, C$_{13}$H$_6$N$_4$O$_9$ (M=362.22) requires C, 43.13; H, 1.52; N, 15.47%.

Example 3

3,6-Diamino-9(10H)-acridone (4) (BR-ACO-2)

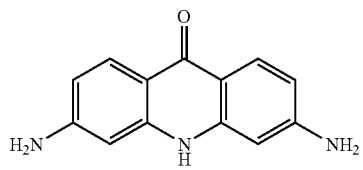

Concentrated HCl (1.18 specific gravity, 300 mL) was added to anhydrous SnCl$_2$ (94.80 g, 0.50 mol) and the mixture heated to reflux (care, HCl gas evolved) to produce a clear solution. The ketone 3 (15.00 g, 41.41 mmol) was added in portions over 30 min maintaining the temperature at 90-100° C. To the resultant suspension was added EtOH (25 mL) and concentrated HCl (30 mL) and reflux continued for a further 3 hr. On cooling a further aliquot of HCl (50 mL) was added and the mixture left to stand for 18 hr. The resultant brown solid (hydrochloride salt) was collected and dried under air, this product was digested in hot dilute aq. HCl (0.1 M, 230 mL), refluxed with decolourising charcoal and filtered while hot. On cooling the solution was neutralised with aq NaOH (20% w/v, 150 mL) to pH ~13 producing a light brown solid. This resultant mixture was heated to reflux for 20 min and filtered while hot. The residual solid was washed with 20% NaOH (50 mL) and hot H$_2$O until the

Example 4

3,6-Bis(3-chloropropionamido)-9(10H)-acridone (5) (BR-ACO-3)

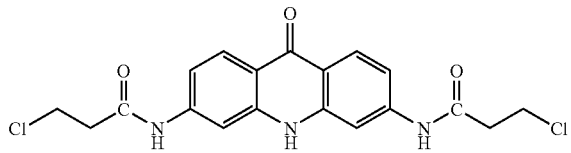

A suspension of 4 (40.0 g, 0.178 mol), in 3-chloropropionyl chloride (3-CPC) (200 mL) was heated under reflux for 2 hr. The resultant mixture was cooled to 0° C. then filtered, the collected product was washed with copious amounts of $H_2O$, EtOH (2×300 mL) and ether (2×200 mL), to provide the chloroamide 5 as a yellow solid (64.0 g, 88%), which was recrystallised from DMF-EtOH (5:1 v/v).

Mp>300° C., $^1$H-NMR (DMSO) δ 2.92 (4H, t, J 6.3 Hz, COCH$_2$CH$_2$Cl), 3.93 (4H, t, J 6.3 Hz, COCH$_2$CH$_2$Cl), 7.25 (2H, dd, J 1.8 Hz, J 8.8 Hz, H-2,7), 8.11 (2H, d, J 8.8 Hz, H-1,8), 8.14(2H, d, J 1.8 Hz, H-4,5), 10.54 (2H, s, NHCO), 11.76 (1H, s, H-10). m/z (EI) 406.0715 ($C_{19}H_{17}N_3Cl_2$ M+H requires 406.0725), found C, 54.78; H, 4.12; N, 9.92% (anhydrous $C_{19}H_{17}N_3Cl_2$ 1.0 mol $H_2O$). Calcd C, 54.95; H, 4.37; N, 10.12%.

Example 5

General Aminolysis Procedure (6)

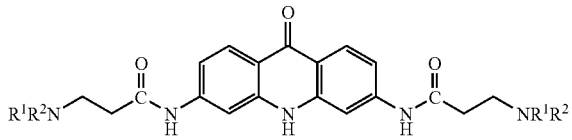

To a stirred refluxing suspension of 5 and NaI (0.3 g) in EtOH (70 mL) was added dropwise a suitable 2° amine, NHR$^1$R$^2$ (2.5 mL) in EtOH (15 mL). The mixture was stirred at reflux for a further 3 hr. After cooling the majority of EtOH was removed under vacuum and then filtered, the collected solid was dissolved in CHCl$_3$ (100 mL) and washed with dilute ammonia solution (2×75 mL), brine (100 mL), dried and stirred over charcoal. The solvent was evaporated to produce a solid product. Recrystalisation EtOH/DMF provided the desired amine, 6.

The acid addition salts of these amine derivatives, 7, were prepared to increase solubility for biological evaluation.

Example 6

3,6-Bis[3-(pyrrolidino)propionamido]-9(10H)-acridone (BR-ACO-14)

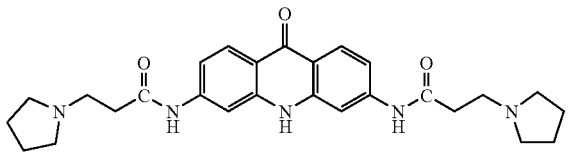

Chloroamide 5 (1.0 g, 2.5 mmol) was treated with pyrrolidine (3 mL) according to the general aminolysis procedure to give the desired product BR-ACO-14 (0.71 g, 61%) as a yellow solid.

Mp>320° C., NMR (DMSO) δ 1.69 (8H, m, N(CH$_2$CH$_2$)$_2$), 2.50 (8H, m, N(CH$_2$CH$_2$)$_2$), 2.55 (4H, t, J 7.1 Hz, COCH$_2$CH$_2$N), 2.75 (4H, t, J 7.1 Hz, COCH$_2$CH$_2$N), 7.15 (2H, dd, J 1.7 Hz, J 8.8 Hz, H-2,7), 8.07 (2H, d, J 8.7 Hz, H-1,8), 8.11 (2H, d, J 1.7 Hz, H-4,5), 10.47 (2H, s, NHCO), 11.62 (1H, s, H-10), m/z (EI) 476.2654 ($C_{27}H_{34}N_5O_3$ M+H requires 476.2662), found C, 65.80; H, 6.80; N, 14.19%. Calcd (anhydrous $C_{27}H_{34}N_5O_3$.1.0 mol $H_2O$) C, 65.70; H, 7.15; N, 14.19%.

Example 7

Dihydrochloride Salt (BR-ACO-4)

The dihydrochloride addition salt, BR-ACO-4, of the compound in the previous example, was also prepared by treatment with HCl.

Example 8

3,6-Bis[3-(piperidino)propionamido]-9(10H)-acridone (BR-ACO-15)

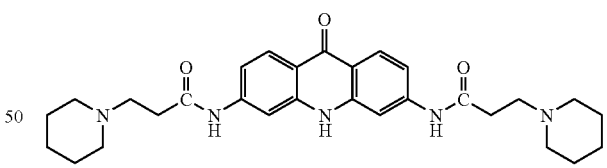

Chloroamide 5 (1.0 g, 2.5 mmol) was treated with piperidine (3 mL) according to the general aminolysis procedure to give the desired product BR-ACO-15 (0.81 g, 60%) as a yellow solid.

Mp>320° C. $^1$H-NMR (CDCl$_3$) δ 1.61 (4H, m, N(CH$_2$CH$_2$)CH$_2$), 1.77 (8H, m, N(CH$_2$CH$_2$)CH$_2$), 2.61 (8H, m, N(CH$_2$CH$_2$)$_2$), 2.65 (4H, t, J 5.5 Hz, COCH$_2$CH$_2$N), 2.74 (4H, t, J 5.5 Hz, COCH$_2$CH$_2$N), 6.84 (2H, dd, J 1.9 Hz, J 8.7 Hz, H-2,7), 8.29 (2H, d, J 1.9 Hz, H-4,5), 8.37 (2H, d, J 8.7 Hz, H-1,8), 9.02 (1H, s, H-10) 11.77 (2H, s, NHCO), m/z (EI) 504.2974 ($C_{29}H_{38}N_5O_3$ M+H requires 504.2975), found C, 64.47; H, 7.56; N, 12.83%. Calcd (anhydrous $C_{29}H_{37}N_5O_3$.2.0 mol $H_2O$) C, 64.54; H, 7.66; N, 12.98%.

Example 9

Dihydrochloride Salt (BR-ACO-5)

The dihydrochloride addition salt, BR-ACO-5, of the compound in the previous example, was also prepared by treatment with HCl.

Example 10

3,6-Bis[3-(dimethylamino)propionamido]-9(10H)-acridone (BR-ACO-11)

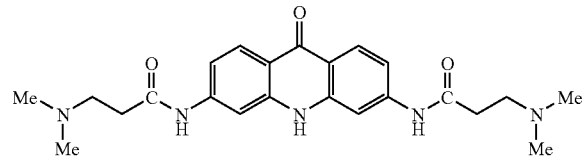

Chloroamide 5 (1.0 g, 2.5 mmol) was treated with dimethylamine (3 mL) according to the general aminolysis procedure to give the desired product BR-ACO-11 (0.71 g, 67%) as a yellow solid.

Mp>320° C. $^1$H-NMR (DMSO) δ 2.19 (12H, s, N(CH$_3$)$_2$), 2.50 (4H, t, J 5.5 Hz, COCH$_2$CH$_2$N), 2.62 (4H, t, J 5.5 Hz, COCH$_2$CH$_2$N), 7.17 (2H, dd, J 1.9 Hz, J 8.8 Hz, H-2,7), 8.11 (2H, d, J 1.9 Hz, H-4,5) 8.17 (2H, d, J 8.8 Hz, H-1,8), 10.39 (2H, s, NHCO), 11.58 (1H, s, H-10), m/z (EI) 424.2346 (C$_{23}$H$_{30}$N$_5$O$_3$ M+H requires 424.2349), found C, 62.41; H, 7.02; N, 15.75%. Calcd (anhydrous C$_{23}$H$_{29}$N$_5$O$_3$.1.0 mol H$_2$O) C, 62.57; H, 7.08; N, 15.86%.

Example 11

Dihydrochloride Salt (BR-ACO-6)

The dihydrochloride addition salt, BR-ACO-6, of the compound in the previous example, was also prepared by treatment with HCl.

Example 12

3,6-Bis[3-(diethylamino)propionamido]-9(10H)-acridone (BR-ACO-12)

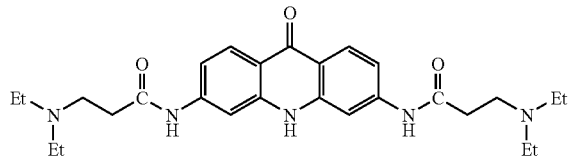

Chloroamide 5 (1.0 g, 2.5 mmol) was treated with diethylamine (3 mL) according to the general aminolysis procedure to give the desired product BR-ACO-12 (0.74 g, 62%) as a yellow solid.

Mp>320° C.; $^1$H-NMR (CDCl$_3$) δ 1.70 (12H, t, J 7.2 Hz, N(CH$_2$CH$_3$)$_2$), 2.63 (4H, t, J 6.2 Hz, COCH$_2$CH$_2$N), 2.73 (8H, q, J 7.2 Hz, N(CH$_2$CH$_3$)$_2$), 2.83 (4H, t, J 6.2 Hz, COCH$_2$CH$_2$N), 6.76 (2H, dd, J 1.9 Hz, J 8.7 Hz, H-2,7), 8.36 (2H, d, J 1.9 Hz, H-4,5) 8.38 (2H, d, J 8.8 Hz, H-1,8), 9.63(1H, s, H-10), 11.83 (2H, s, NHCO), m/z (EI) 480.2987 (C$_{27}$H$_{38}$N$_5$O$_3$ M+H requires 480.2375), found C, 63.96; H, 7.73; N, 13.75%. Calcd (anhydrous C$_{27}$H$_{37}$N$_5$O$_3$.1.5 mol H$_2$O) C, 64.01; H, 7.96; N, 13.82%.

Example 13

Dihydrochloride Salt (BR-ACO-7)

The dihydrochloride addition salt, BR-ACO-7, of the compound in the previous example, was also prepared by treatment with HCl.

Example 14

3,6-Bis[3-(morpholino)propionamido]-9(10H)-acridone (BR-ACO-13)

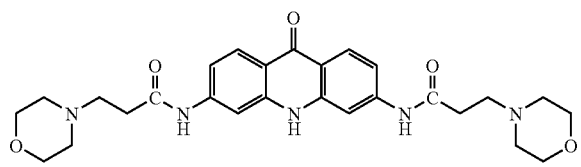

Chloroamide 5 (1.0 g, 2.5 mmol) was treated with morpholine (3 mL) according to the general aminolysis procedure to give the desired product BR-ACO-13 (1.10 g, 87%) as a pale yellow solid.

Mp>320° C. $^1$H-NMR (DMSO) δ 2.43 (8H, t, J 4.5 Hz, N(CH$_2$CH$_2$)O), 2.55 (4H, t, J 6.8 Hz, COCH$_2$CH$_2$N), 2.67, 2.75 (4H, t, J 6.8 Hz, COCH$_2$CH$_2$N), 3.59 (8H, t, J 4.5 Hz, N(CH$_2$CH$_2$)O), 7.18 (2H, dd, J 1.8 Hz, J 8.8 Hz, H-2,7), 8.09 (2H, d, J 8.7 Hz, H-1,8), 8.11 (2H, d, J 1.8 Hz, H-4,5), 10.41 (2H, s, NHCO), 11.59 (1H, s, H-10) m/z (EI) 508.22561 (C$_{27}$H$_{34}$N$_5$O$_5$ M+H requires 508.2560), found C, 61.90; H, 6.74; N, 13.42%. Calcd (anhydrous C$_{27}$H$_{33}$N$_5$O$_5$.1.0 mol H$_2$O) C, 61.70; H, 6.71; N, 13.32%.

Example 15

Dihydrochloride Salt (BR-ACO-8)

The dihydrochloride addition salt, BR-ACO-8, of the compound in the previous example, was also prepared by treatment with HCl.

Example 16

3,6-Bis[3-(4-methylpiperidino)propionamido]-9(10H)-acridone (BR-ACO-23)

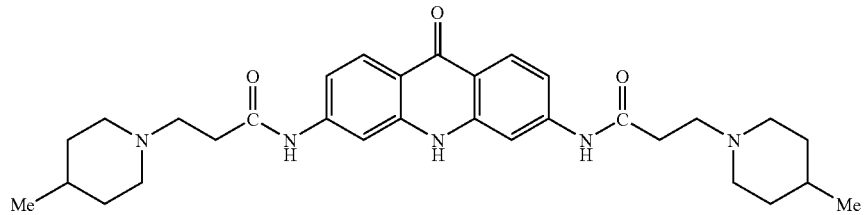

Chloroamide 5 (1.0 g, 2.5 mmol) was treated with 4-methylpiperidine (3 mL) according to the general aminolysis procedure to give the desired product BR-ACO-23 (0.75 g, 57%) as a pale yellow solid.

Mp>320° C., $^1$H-NMR (DMSO) δ 0.90 (6H, d, J 6.3 Hz, 2×CH$_3$), 1.19 (2H, m, N(CH$_2$CH$_2$)$_2$CH), 1.57 (4H, m, N(CH$_2$CH$_{2a}$)$_2$CH), 1.95 (4H, m, NCH$_2$CH$_{2b}$)$_2$CH), 2.51 (8H, m, N(CH$_2$CH$_2$)$_2$CH), 2.56 (4H, t, J 7.1 Hz, COCH$_2$CH$_2$N), 2.85 (4H, t, J 7.1 Hz, COCH$_2$CH$_2$N), 7.16 (2H, dd, J 1.7 Hz, J 8.9 Hz, H-2,7), 8.09 (2H, d, J 8.9 Hz, H-1,8), 8.11 (2H, d, J 1.7 Hz, H-4,5), 10.51 (2H, s, NHCO), 11.60 (1H, s, H-10), m/z (EI) 532.3285 (C$_{31}$H$_{42}$N$_5$O$_3$ M+H requires 532.3288), found C, 67.73; H, 7.51; N, 13.23%. Calcd (anhydrous C$_{31}$H$_{41}$N$_5$O$_3$·1.0 mol H$_2$O) C, 67.73; H, 7.88; N, 12.74%.

Example 17

Dihydrochloride Salt (BR-ACO-33)

The dihydrochloride addition salt, BR-ACO-33, of the compound in the previous example, was also prepared by treatment with HCl.

Example 18

3,6-Bis[3-(4-hydroxypiperidino)propionamido]-9(10H)-acridone (BR-ACO-24)

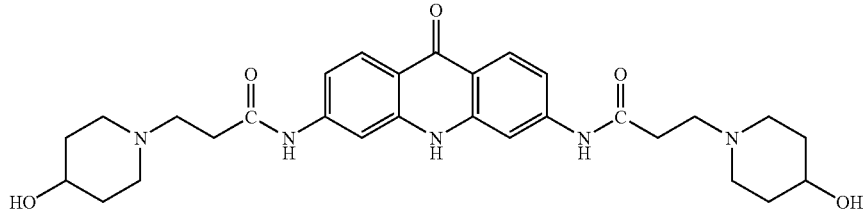

Chloroamide 5 (1.0 g, 2.5 mmol) was treated with 4-hydroxypiperidine (3 mL) according to the general aminolysis procedure to give the desired product BR-ACO-24 (0.67 g, 50%) as a pale yellow solid.

Mp>320°0 C., $^1$H-NMR (DMSO) δ 1.44 (4H, m, N(CH$_2$CH$_{2a}$)$_2$CH), 1.73 (4H, m, NCH$_2$CH$_{2b}$)$_2$CH), 2.11 (4H, m, N(CH$_{2a}$CH$_2$)$_2$CH), 2.55 (4H, t, J 6.7 Hz, COCH$_2$CH$_2$N), 2.62 4H, m, N(CH$_{2b}$CH$_2$)$_2$CH), 2.77 (4H, t, J 6.7 Hz, COCH$_2$CH$_2$N), 4.53 (2H, m, N(CH$_2$CH$_2$)$_2$CH), 7.16 (2H, dd, J 1.6 Hz, J 8.8 Hz, H-2,7), 8.07 (2H, d, J 8.8 Hz, H-1,8), 8.11 (2H, d, J 1.6 Hz, H-4,5), 10.52 (2H, s, NHCO), 11.61 (1H, s, H-10), m/z (EI) 536.2872 (C$_{29}$H$_{37}$N$_5$O$_5$ requires 536.2873), found C, 61.77; H, 7.00; N, 13.39%. Calcd (anhydrous C$_{29}$H$_{37}$N$_5$O$_5$·1.5 mol H$_2$O) C, 61.91; H, 7.17; N, 12.45%

Example 19

Dihydrochloride Salt (BR-ACO-34)

The dihydrochloride addition salt, BR-ACO-34, of the compound in the previous example, was also prepared by treatment with HCl.

Example 20

3,6-Bis[3-(2-methylpiperidino)propionamido]-9(10H)-acridone (BR-ACO-26)

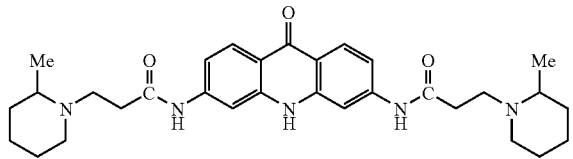

Chloroamide 5 (1.0 g, 2.5 mmol) was treated with 2-methylpiperidine (3 mL) according to the general aminolysis procedure to give the desired product BR-ACO-26 (0.76 g, 57%) as a pale yellow solid.

Mp>320° C., $^1$H-NMR (DMSO) δ 1.19 (6H, d, J 6.3 Hz, CH$_3$), 1.62 (12H, m, CH$_2$), 2.34 (4H, t, J 6.7 Hz, COCH$_2$CH$_2$N), 2.56 (4H, t, J 6.7 Hz, COCH$_2$CH$_2$N), 2.68 (6H, m, NCH$_2$, NCH), 7.13 (2H, dd, J 1.6 Hz, J 8.8 Hz, H-2,7), 8.11 (2H, d, J 8.8 Hz, H-1,8), 8.14 (2H, d, J 1.6 Hz, H-4,5), 10.51 (2H, s, NHCO), 11.63(1H, s, H-10), m/z (EI) 532.3286 (C$_{31}$H$_{41}$N$_5$O$_3$ M+H requires 532.3288), found C, 67.66; H, 7.38; N, 12.61%. Calcd (anhydrous C$_{31}$H$_{41}$N$_5$O$_3$·1.0 mol H$_2$O) C, 67.73; H, 7.88; N, 12.74%.

Example 21

Dihydrochloride Salt (BR-ACO-36)

The dihydrochloride addition salt, BR-ACO-36, of the compound in the previous example, was also prepared by treatment with HCl.

Example 22

3,6-Bis[3-(2-ethylpiperidino)propionamido]-9(10H)-acridone (BR-ACO-27)

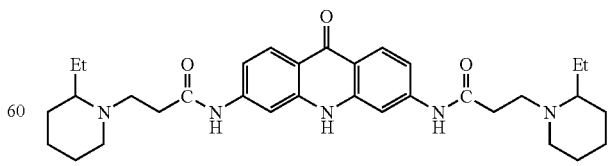

Chloroamide 5 (1.0 g, 2.5 mmol) was treated with 2-ethylpiperidine (3 mL) according to the general aminolysis procedure to give the desired product BR-ACO-27 (0.79 g, 57%) as a pale yellow solid.

Mp>320° C., $^1$H-NMR (DMSO) δ 0.83 (6H, t, 7.1 Hz, CH$_2$CH$_3$), 1.39 (4H, m, CH$_2$CH$_3$), 1.52 (12H, m, CH$_2$), 2.24 (4H, t, J 6.7 Hz, COCH$_2$CH$_2$N), 2.51 (4H, t, J 6.7 Hz, COCH$_2$CH$_2$N), 2.71 (6H, m, NCH$_2$, NCH), 7.17 (2H, dd, J 1.6 Hz, J 8.8 Hz, H-2,7), 8.07 (2H, d, J 8.8 Hz, H-1,8), 8.11 (2H, d, J 1.6 Hz, H-4,5), 10.49 (2H, s, NHCO), 11.60 (1H, s, H-10), m/z (EI) 559.9994 (C$_{33}$H$_{45}$N$_5$O$_3$ requires 560.3601), found C, 70.47; H, 8.12; N, 12.45%. Calcd (C$_{33}$H$_{45}$N$_5$O$_3$) C, 70.81; H, 8.1; N, 12.51%.

Example 23

Dihydrochloride Salt (BR-ACO-37)

The dihydrochloride addition salt, BR-ACO-37, of the compound in the previous example, was also prepared by treatment with HCl.

Example 24

3,6-Bis[3-(N-ethylpiperazino)propionamido)propionamido]-9(10H)-acridone (BR-ACO-29)

Example 25

Dihydrochloride Salt (BR-ACO-39)

The dihydrochloride addition salt, BR-ACO-39, of the compound in the previous example, was also prepared by treatment with HCl.

Example 26

3,6-Bis[(1,3,3-trimethyl-6-azabicyclo[3.2.1]-octanamino)propionamido]-9(10H)-acridone (JH-ACO-31)

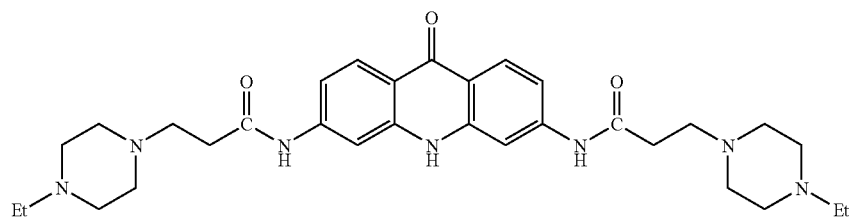

Chloroamide 5 (1.0 g, 2.5 mmol) was treated with N-ethylpiperizine (3 mL) according to the general aminolysis procedure to give the desired product BR-ACO-29 (0.76 g, 57%) as a pale yellow solid.

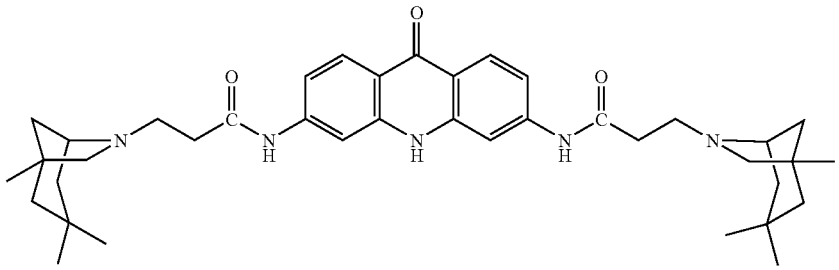

Mp>320° C., $^1$H-NMR (DMSO) δ 1.14 (6 H, t, CH$_2$CH$_3$), 1.62 (12H, m, CH$_2$), 2.34 (4H, t, J 6.7 Hz, COCH$_2$CH$_2$N), 2.56 (4H, t, J 6.7 Hz, COCH$_2$CH$_2$N), 2.65 (20H, m, NCH$_2$), 2.68 (6H, m, NCH$_2$, NCH), 7.13 (2H, dd, J 1.6 Hz, J 8.8 Hz, H-2,7), 8.11 (2H, d, J 8.8 Hz, H-1,8), 8.14 (2H, d; J 1.6 Hz, H-4,5), 10.51 (2H, s, NHCO), 11.63(1H, s, H-10), m/z (EI) 561.3427 (C$_{31}$H$_{42}$N$_7$O$_3$ M+H requires 561.3412), found C, 67.66; H, 7.38; N, 12.61%. Calcd (anhydrous C$_{31}$H$_{41}$N$_5$O$_3$.1.0 mol H$_2$O) C, 63.94; H, 7.72; N, 16.82%.

Chloroamide 5 (2.5 g, 5.9 mmol) was treated with 1,3,3-trimethyl-6-azabicyclo[3.2.1]-octane (7.0 mL) according to the general aminolysis procedure to give the desired product JH-ACO-31 (3.1 g, 82%) as a yellow solid.

Mp>320° C., $^1$H-NMR (DMSO) δ 0.84 (6H, s, CH$_3$), 1.02 (6H, s, CH$_3$), 1.25 (4H, m, CH$_2$) 1.07 (6H, s, CH$_3$), 1.21 (4H, m, CH$_2$), 1.34 (4H, m, CH$_2$), 2.34 (2H, m, CH), 2.63 (4H, t, COCH$_2$), 3.07 (4H, m, COCH$_2$CH$_2$N), 3.20-3.30 (4H, m, CH$_2$), 7.21 (2H, d, J 8.8 Hz, H-1,8), 8.09 (2 H, s, H-4,5), 8.14 (2 H, d, J 8.8 Hz, H-2,7), 10.48 (2 H, s, NHCO), m/z (EI) 640.4238 (C$_{39}$H$_{53}$N$_5$O$_3$ M+H requires 640.4226).

Example 27

Dihydrochloride Salt (JH-ACO-32)

The dihydrochloride addition salt, JH-ACO-32, of the compound in the previous example, was also prepared by treatment with HCl.

GROUP B: 2,7-ACRIDINES

Example 28

2-(4-Amino-phenylamino)-5-nitrobenzoic acid (10)

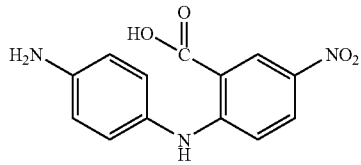

A mixture of 2-chloro-5-nitrobenzoic acid 9 (150 g, 0.744 mol), 1,4-phenylenediamine 8 (150.0 g, 1.387 mol), anhydrous potassium carbonate (309 g, 2.236 mol), copper powder (2.0 g, 31.5 mol), cupric sulfate (10 mg) and water (2.25 l) was heated to reflux with stirring for 5 hr. It was then filtered hot through a fluted paper and allowed to stand overnight at room temperature. The potassium salt of the product was collected on a glass sinter and washed with ice-cold water (2×250 mL) followed by ice-cold ethanol (250 mL). The product was dissolved in boiling water (1250 mL) and acetic acid was then added until there was no further precipitation. The mixture was cooled with an external ice water bath and the product collected. The product was washed with ice-cold water (3×500 mL) followed by ice-cold ethanol (2×500 mL), dry ether (250 mL) and finally hexane (2×500 mL). The product was dried over $P_2O_5$ under vacuum to yield a light brown solid 10 (130.52 g 64%).

Example 29

2-amino-7-nitro-9(10H)-acridone (11)

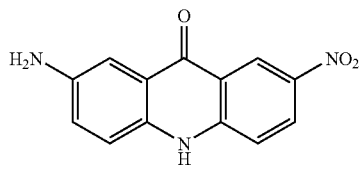

See Korolev et al., 1976. Polyphosphoric acid was freshly prepared by slowly adding, with stirring, 85% orthophosphoric acid (360 mL) to phosphorus pentoxide (600 g). The mixture was then heated on a steam bath with stirring until a clear viscous liquid was obtained. 2-(-4-amino-phenylamino)-5-nitrobenzoic acid 10 (107.76 g, 0.394 mol) was added with stirring over the course of 5 min. Heating on the steam bath was continued for 6 hr, the mixture being stirred occasionally. Whilst still hot, the mixture was poured into 4 L of ice-water, stirred for 30 min and allowed to stand overnight. The mixture was adjusted to pH 8.0 by the addition of 0.88 s.g. aqueous ammonia, chilled for 2 hr, and the crude product collected on a glass sinter. It was washed with dilute ammonia (1% 0.88 s.g. aqueous ammonia in water, 250 mL) followed by water (3×250 mL), ice-cold ethanol (2×250 mL), dry ether (2×250 mL) and finally hexane (250 mL). The product, 11, was dried over $P_2O_5$ under vacuum to yield a red-brown solid (97.04 g, 96%).

Mp>350° C. (lit. >350° C.; Korolev et al., 1976) $^1$H-NMR ($d_6$-DMSO) δ 5.45 (2 H, br s, $D_2O$ exchanges, —$NH_2$), 7.20 (1 H, d, J 8.8 Hz, H-3), 7.38 (1 H, s, H-1), 7.40 (1H, d, J 9.1 Hz, H-4), 7.58 (1 H, d, 9.2 Hz, H-5), 8.35 (1H, d, 9.3 Hz, H-6), 8.98 (1H, s, H-8), 12.11 (1H, br s, $D_2O$ exchanges, H-10).

Example 30

2,7-diamino-9(10H)-acridone (12)

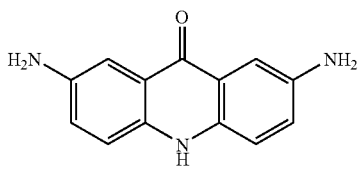

See Bogert et al., 1930. To a stirred suspension of 2-amino-7-nitro-9(10H)-acridone 11 (22.5 g, 88.2 mmol) in ethanol was added, in one lot, a solution of sodium sulphide nonahydrate (94.5 g, 0.394 mol) and sodium hydroxide (37.5 g, 0.938 mol) in water (1.625 L). The mixture was refluxed with stirring for 16 hr. On cooling, saturated sodium bicarbonate solution (250 mL) was added and the total volume of the mixture reduced to 700 mL on a rotary evaporator. The flask was chilled in ice for 3 hr after which the product was collected on a glass sinter. The product was washed with water (4×200 mL) followed by ice-cold ethanol (2×100 mL), dry ether (2×100 mL) and finally hexane (2×100 mL). The product, 12, was dried over $P_2O_5$ under vacuum to yield an olive-green solid (18.70 g, 94%).

Mp 280° C. dec. (lit. 325° C.; Bogert et al. 1930) $^1$H-NMR ($d_6$-DMSO) δ 4.98 (4H, br s, $D_2O$ exchanges, —$NH_2$), 7.05 (2H, dd, J 2.5 Hz, J 8.8 Hz, H-3,6), 7.25 (2H, d, J 8.8 Hz, H-4,5), 7.31 (2H, d, J 2.4 Hz, H-1,8), 11.06 (1H, s, $D_2O$ exchanges, H-10).

Example 31

2,7-Bis(3-chloropropionamido)-9(10H)-acridone (13)

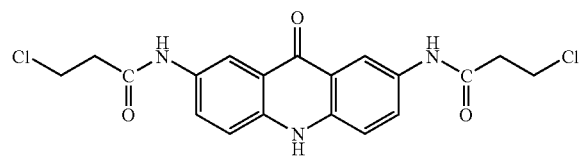

A suspension of 2,7-diamino-9(10H)-acridone 12 (13.44 g, 60 mmol), in 3-chloropropionyl chloride (3-CPC) (240 mL) was stirred at 90° C. for 4 hr and then heated under reflux for 2 hr. The resultant mixture was cooled to 0° C. after which the product was collected on a glass sinter. The product was washed with acetone (60 mL) followed by toluene (2×60 mL), more acetone (4×60 mL), dry ether (2×60 mL) and finally hexane (2×60 mL). The product was dried over $P_2O_5$ under vacuum to yield an olive-green solid (19.68 g, 81%).

Mp>350° C. $^1$H-NMR ($d_6$-DMSO) δ 2.86 (4H, t, J 6.5 Hz, COCH$_2$CH$_2$Cl), 4.01 (4H, t, J 6.5 Hz, COCH$_2$CH$_2$Cl), 7.63 (2H, d, J 8.7 Hz, H-4,5), 8.07 (2H, d, J 8.7 Hz, H-3,6), 8.61 (2H, s, H-1,8), 10.38 (2H, s, $D_2O$ exchanges, NHCO), 11.86 (1H, s, $D_2O$ exchanges, H-10).

Example 32

General Aminolysis Procedure (14)

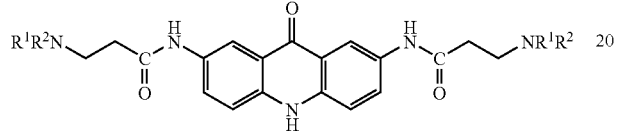

To a stirred refluxing suspension of 13 and NaI (0.3 g) in EtOH (70 mL) was added dropwise a suitable 2° amine, NHR$^1$R$^2$ (2.5 mL, 30 mmol) in EtOH (15 mL). The mixture was stirred at reflux for a further 3 hr. After cooling the majority of EtOH was removed under vacuum and then filtered, the collected solid was dissolved in CHCl$_3$ (100 mL) and washed with dilute ammonia solution (2×75 mL), brine (100 mL), dried and stirred over charcoal. The solvent was evaporated to produce a solid. Recrystalisation EtOH/DMF provided the desired amine 14.

The acid addition salts of these amine derivatives, 15, were prepared (by treatment with HCl) to increase solubility for biological evaluation.

Example 33

2,7-Bis[3-(pyrrolidino)propionamido]-9(10H)-acridone (BR-ACO-16)

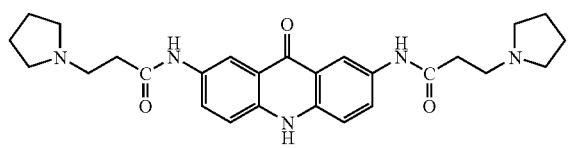

Chloroamide 13 (400 mg, 1.0 mmol) was treated with pyrrolidine (3 mL) according to the general aminolysis procedure to give the desired product BR-ACO-16 (348.mg, 74.4%) as a dark yellow solid.

Mp>320° C., $^1$H-NMR (DMSO) δ 1.69 (8 H, m, N(CH$_2$CH$_2$)$_2$), 2.50 (8H, m, N(CH$_2$CH$_2$)$_2$), 2.52 (4H, t, J 7.2 Hz, COCH$_2$CH$_2$N), 2.74 (4H, t, J 7.2 Hz, COCH$_2$CH$_2$N), 7.49 (2H, d, J 9.0 Hz, H-4,5), 7.91 (2H, dd, J 2.4 Hz, J 9.0 Hz, H-3,6), 8.46 (2H, d, J 2.4 Hz, H-1,8), 10.20 (2H, s, NHCO), 11.702 (1H, s, H-10). m/z (EI) 476.2652 (C$_{27}$H$_{34}$N$_5$O$_3$ M+H requires 476.2662), found C, 66.43; H, 6.78; N, 14.72%. Calcd (anhydrous C$_{27}$H$_{33}$N$_5$O$_3$.0.7 mol H$_2$O) C, 66.43; H, 7.10; N, 14.35%.

Example 34

Dihydrochloride Salt (BR-ACO-9)

The dihydrochloride addition salt, BR-ACO-9, of the compound in the previous example, was also prepared by treatment with HCl.

Example 35

2,7-Bis[3-(piperidino)propionamido]-9(10H)-acridone (BR-ACO-17)

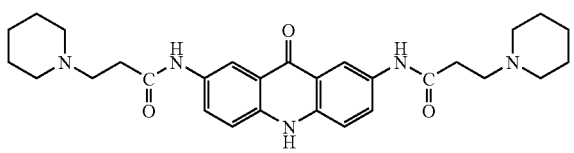

Chloroamide 13 (400 mg, 1.0 mmol) was treated with piperidine (3 mL) according to the general aminolysis procedure to give the desired product BR-ACO-17 (300 mg, 61%) as a dark yellow solid.

Mp>320° C., $^1$H-NMR (CDCl$_3$) δ 1.56 (4H, m, N(CH$_2$CH$_2$)CH$_2$), 1.67 (8H, m, N(CH$_2$CH$_2$)CH$_2$), 2.57 (8H, m, N(CH$_2$CH$_2$)$_2$), 2.65 (4H, t, J 6.7 Hz, COCH$_2$CH$_2$N), 2.79 (4H, t, J 6.7 Hz, COCH$_2$CH$_2$N), 7.65 (2H, d, J 8.8 Hz, H-4,5), 8.07 (2H, d, J 8.8 Hz, H-3,6) 8.61 (2H, s, H-1,8), 10.46 (1H, s, H-10) 11.85 (2H, s, NHCO) m/z (EI) 504.2973 (C$_{29}$H$_{38}$N$_5$O$_3$ M+H requires 504.2975), found C, 64.47; H, 7.56; N, 12.83%. Calcd (anhydrous C$_{29}$H$_{37}$N$_5$O$_3$.2.0 mol H$_2$O) C, 64.54; H, 7.66; N, 12.98%.

Example 36

Dihydrochloride Salt (BR-ACO-10)

The dihydrochloride addition salt, BR-ACO-10, of the compound in the previous example, was also prepared by treatment with HCl.

Example 37

2,7-Bis(3-dimethylaminopropionamido)-9(10H)-acridone (JH-ACO-23)

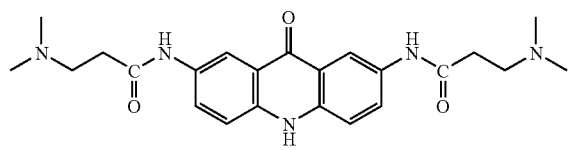

Chloroamide 13 (1.0 g, 2.5 mmol) was treated with dimethylamine (7.0 mL) according to the general aminolysis procedure to give the desired product JH-ACO-23 (630 mg, 61%) as a pale yellow solid.

Mp>320° C. $^1$H-NMR (DMSO) δ 2.25 (12H, s, N(CH$_3$)$_2$), 2.54 (4H, t, J 6.9 Hz, COCH$_2$CH$_2$N), 2.72 (4H, t, J 6.9 Hz, COCH$_2$CH$_2$N), 7.38 (2H, d, J 8.7 Hz, H-4,5), 7.89 (2H, dd, J 1.9 Hz, J 8.7 Hz, H-3,6), 8.51 (2H, d, J 1.9 Hz, H-1,8), 10.29 (2H, s, NHCO), 11.72 (1H, s, H-10), m/z (EI)

424.2346 ($C_{23}H_{30}N_5O_3$ M+H requires 424.2349), found C, 63.51; H, 7.04; N, 16.20%. Calcd (anhydrous $C_{23}H_{29}N_5O_3 \cdot 0.7$ mol $H_2O$) C, 63.34; H, 7.03; N, 16.06%.

Example 38

Dihydrochloride Salt (JH-ACO-22)

The dihydrochloride addition salt, JH-ACO-22, of the compound in the previous example, was also prepared by treatment with HCl.

Example 39

2,7-Bis[3-(4'-N-methyl)piperizinopropionamido]-9 (10H)-acridone (JH-ACO-27)

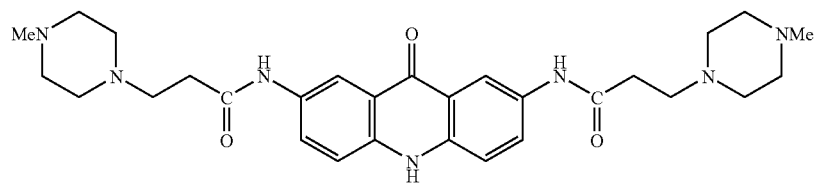

Chloroamide 13 (1.0 g, 2.5 mmol) was treated with N-methylpiperizine (5 mL) according to the general aminolysis procedure to give the desired product JH-ACO-27 (930 mg, 71%) as a pale yellow/green solid.

Mp>320° C. $^1$H-NMR (DMSO) δ 2.34 (4H, t, J 6.7 Hz, COCH$_2$CH$_2$N), 2.56 (4H, t, J 6.7 Hz, COCH$_2$CH$_2$N), 2.65 (16H, m, NCH$_2$), 2.68 (6H, m, NCH$_3$), 7.38 (2H, d, J 8.6 Hz, H-4,5), 7.89 (2H, dd, J 1.9 Hz, J 8.6 Hz, H-3,6), 8.51 (2H, d, J 1.9 Hz, H-1,8), 10.29 (2H, s, NHCO), 11.72 (1H, s, H-10), m/z (EI) 533.3125 ($C_{29}H_{39}N_7O_3$ M+H requires 533.3114), found C, 63.77; H, 7.38, N, 17.95%. Calcd (anhydrous $C_{29}H_{39}N_7O_3 \cdot 0.5$ mol $H_2O$) C, 64.18, H, 7.43, N, 18.07%.

Example 40

Dihydrochloride Salt (JH-ACO-28)

The dihydrochloride addition salt, JH-ACO-28, of the compound in the previous example, was also prepared by treatment with HCl.

Example 41

2,7-Bis[3-(2-methylpiperidino)propionamido]-9 (10H)-acridone (JM-ACO-06)

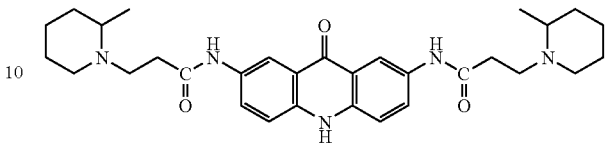

Chloroamide 13 (1.0 g, 2.5 mmol) was treated with 2-methylpiperidine (5 mL) according to the general aminolysis procedure to give the desired product JM-ACO-06 (916 mg, 69%) as a pale yellow/green solid.

$^1$H-NMR (DMSO) δ 1.21 (6 H, d, J 6.1 Hz, CH$_3$), 1.62 (12 H, m, CH$_2$), (8 H, m, N(CH$_2$CH$_2$)$_2$CH), 2.48 (4 H, t, 6.5 Hz, COCH$_2$CH$_2$N), 2.63 (6 H, m, NCH$_2$, NCH), 3.01 (4 H, m, COCH$_2$CH$_2$N), 7.58 (2H, d, J 8.9 Hz, H-4,5), 7.90 (2H, d, J 8.9 Hz, H-3,6), 8.53 (2H, s, H 1,8), 9.48 (2H, s, NHCO), 10.57 (1H, s, H-10), m/z (EI) 532.3265 ($C_{31}H_{42}N_5O_3$ M+H requires 532.3288).

Example 42

Dihydrochloride Salt (JM-ACO-07)

The dihydrochloride addition salt, JM-ACO-07, of the compound in the previous example, was also prepared by treatment with HCl.

Example 43

2,7-Bis[3-(4-hydroxypiperidino)propionamido]-9(10H)-acridone (JM-ACO-08)

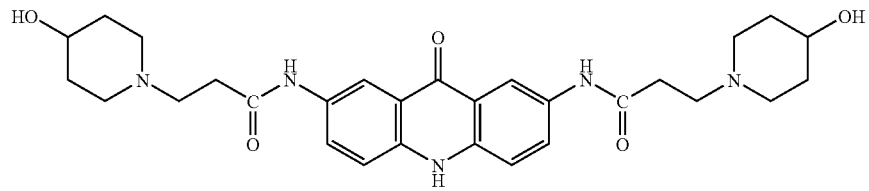

Chloroamide 13 (1.0 g, 2.5 mmol) was treated with 4-hydroxypiperidine (5 mL) according to the general aminolysis procedure to give the desired product JM-ACO-08 (776 mg, 58%) as a pale yellow/green solid.

$^1$H-NMR (DMSO) δ 1.71 (8 H, m, N(CH$_2$CH$_2$)$_2$CH), 1.93 (8 H, m, N(CH$_2$CH$_2$)$_2$CH), 2.9 (12 H, m, CH$_2$) 3.01 (4 H, m, COCH$_2$CH$_2$N), 3.98(2 H, d, CH) 7.56 (2H, d, J 8.9 Hz, H-4,5), 7.91 (2H, d, J 8.9 Hz, H-3,6), 8.53 (2H, s, H 1,8), 10.02 (2H, s, NHCO), 11.47 (1H, s, H-10), m/z (EI) 558.2710 (C$_{29}$H$_{37}$N$_5$O$_5$ M+Na requires 558.2692),), found C, 63.63; H, 6.89, N, 12.64%. Calcd (anhydrous C$_{29}$H$_{37}$N$_5$O$_5$.0.6 mol H$_2$O) C, 63.74, H, 7.05, N, 12.82%.

Example 44

Dihydrochloride Salt (JM-ACO-09)

The dihydrochloride addition salt, JM-ACO-09, of the compound in the previous example, was also prepared by treatment with HCl.

Example 45

2,7-Bis[3-(2-hydroxymethylpiperidino)propionamido]-9(10H)-acridone (JM-ACO-11)

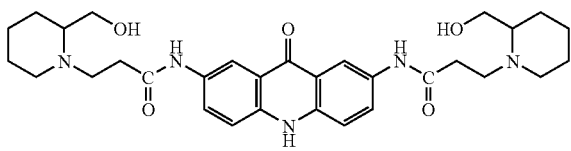

Chloroamide 13 (1.0 g, 2.5 mmol) was treated with 2-hydroxymethylpiperidine (5 mL) according to the general aminolysis procedure to give the desired product JM-ACO-11 (888 mg, 63%) as a pale yellow/green solid.

$^1$H-NMR (DMSO) δ 1.71 (4 H, m, CH$_2$), 1.77 (8 H, m, CH$_2$), 2.79 (2 H, m, CH), 2.9 (8 H, m, COCH$_2$CH$_2$N, NCH$_2$), 3.3 (4 H, m, COCH$_2$CH$_2$N), 3.6 (4 H, m, CH$_2$OH) 7.54 (2H, d, J 8.9 Hz, H-4,5), 7.91 (2H, d, J 8.9 Hz, H-3,6), 8.53 (2H, s, H 1,8), 9.48 (2H, s, NHCO), 10.57 (1H, s, H-10), m/z (EI) 564.3170 (C$_{31}$H$_{42}$N$_5$O$_3$ M+H requires 564.3186).

Example 46

Dihydrochloride Salt (JM-ACO-12)

The dihydrochloride addition salt, JM-ACO-12, of the compound in the previous example, was also prepared by treatment with HCl.

GROUP C: 2,6-ACRIDINES

Example 47

2-(3-Amino-phenylamino)-5-nitrobenzoic acid (AR-ACO-06)

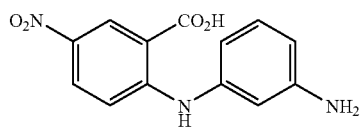

A mixture of 2-chloro-5-nitrobenzoic acid 16 (150.0 g, 744 mmol), 1,3-phenylenediamine 17 (150.0 g, 1.387 mol), anhydrous potassium carbonate (309.0 g, 2.236 mol ), copper powder (2.0 g, 31.5 mmol), cupric sulfate (10 mg) and water (2.0 L) was heated to reflux with stirring for 6.25 hr under argon. It was then allowed to stand overnight at room temperature. Glacial acetic acid was added to the reaction mixture with stirring until pH 5 and the flask cooled in ice water. The mustard yellow solid was collected, washed with ice-cold water (3×100 mL), and redissolved in hot dilute ammonia (300 mL 0.88 s.g. ammonia and 2.7 L water). Charcoal (2.0 g) was added, the mixture refluxed briefly, and then filtered through a fluted paper. On cooling to room temperature the mixture was acidified to pH 5 by adding glacial acetic acid and the flask cooled in ice-water. The product was collected and washed with ice-cold water (2×100 mL) followed by ice-cold ethanol (2×100 mL), dry ether (2×100 mL) and finally hexane (100 mL). The product was dried over P$_2$O$_5$ under vacuum to yield the product AR-ACO-06 (155.10 g, 76%) as brown solid.

Mp 270° C. dec. (lit. 250° C. dec.; Goldstein and de Simo, 1927).

Example 48

3-Amino-7-nitro-9(10H)-acridone (AR-ACO-07)

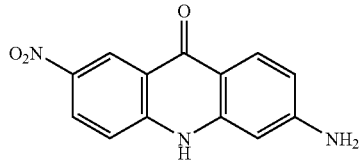

2-(3-Amino-phenylamino)-5-nitrobenzoic acid (AR-ACO-6, 74 g, 270 mmol) was heated with concentrated sulphuric acid (500 mL) on a steam bath at 100° C. for 105 min, chilled in ice-water, and then poured slowly onto crushed ice (2 kg). The mixture was allowed to stand at room temperature overnight before the product was collected by filtration on a glass sinter and washed with distilled water (6×500 mL), followed by very dilute ammonia (2×500 mL, made by diluting 2 mL of 0.88 s.g. ammonia to 1 L), water (2×400 mL) and finally ethanol (200 mL). The product was dried at 105° C. under vacuum for 4 hr to yield an olive-green solid 19 (60.50 g, 87.5%).

Mp 213° C. (lit. 216° C.; Goldberg and Kelly 1946), $^1$H-NMR (DMSO) δ 6.47 (1 H, d, J 1.9 Hz, H-4), 6.61 (1 H, dd, J 2.0 Hz & 8.8 Hz, H-2), 7.51 (1 H, d, J 9.2 Hz, H-5), 7.91 (1 H, d, J 8.8 Hz, H-1), 8.35 (1 H, dd, J 2.7 & 9.2 Hz, H-6), 8.88 (1 H, d, J 2.7 Hz, H-8), 11.78 (1 H, s, H-10).

Example 49

2,6-Diamino-9(10H)-acridone (AR-ACO-08)

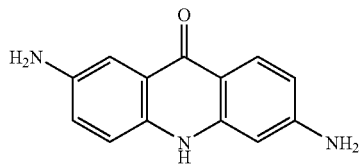

Finely ground 3-amino-7-nitro-9(10H)-acridone (AR-ACO-7, 22.50 g, 88.1 mmol) was suspended in ethanol (950 mL) and stirred at reflux. A solution of sodium sulfide nonahydrate (94.75 g, 394 mmol) and sodium hydroxide (37.5 g, 938 mmol) in water (1.7 L) was added in one lot and refluxing continued for 20 hr. The mixture was allowed to cool to room temperature and ammonium bicarbonate (50 g) was added in one lot and dissolved. The solution was reduced to about 500 mL on a rotary evaporator and allowed to stand overnight. The flask was chilled with ice-water, the product collected, and washed with ice cold water until the filtrate was a pale yellow-green colour. The crude product was dried then dissolved in boiling 1 M hydrochloric acid (900 mL). Charcoal (1 g) was added and the solution filtered whilst hot through a fluted paper. The filtrate was basified to pH 8 by the addition of 0.88 s.g. ammonia and the precipitate collected and was washed with water (2×20 mL) and dried over $P_2O_5$ under vacuum to yield a yellow solid AR-ACO-08 (19.85 g, 61.2%).

Mp>350° C. (lit. 358-360° C.; Goldberg and Kelly 1946); $^1$H-NMR (DMSO) δ 4.96 (2 H, s, 2-NH$_2$), 5.90 (2 H, s, 6-NH$_2$), 6.34 (1 H, s, H-5), 6.43 (1 H, d, J 8.7 Hz, H-7), 6.98 (1 H, dd, J 2.1 Hz & 7.5 Hz, H-3), 7.16 (1 H, d, J 8.7 Hz, H-4), 7.29 (1H, s, H-1), 7.84 (1 H, d, J 8.7 Hz, H-8), 10.76 (1 H, s, H-10).

Example 50

2,6-Bis(3-chloropropionamido)-9(10H)-acridone (AR-ACO-9)

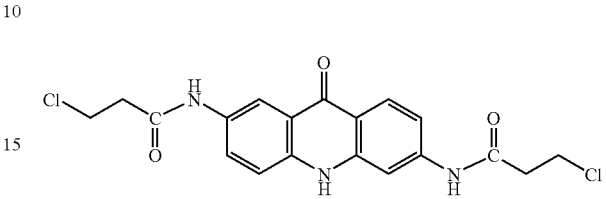

2,6-Diamino-9(10H)-acridone (AR-ACO-8, 8.40 g, 37.3 mmol was suspended in 3-chloropropionyl chloride (100 mL), stirred at room temperature for 1 hr, at 90° C. for 1 hr, and at reflux for 6 hr. Allowed to stand at room temperature overnight and then chilled with ice-water. The product was collected and washed with acetone (2×30 mL) followed by toluene (3×30 mL), acetone again (4×30 mL), ethanol (2×30 mL), dry ether (2×30 mL) and finally hexane (2×30 mL). The product was dried over $P_2O_5$ under vacuum to yield a yellow solid AR-ACO-09 (12.96 g, 86%).

Mp 335° C. dec., $^1$H-NMR (DMSO) δ 2.85 (2 H, t, J 6.2 Hz, 2-NHCOCH$_2$CH$_2$Cl), 2.92 (2 H, t, J 6.2 Hz, 6-NHCOCH$_2$CH$_2$Cl), 3.91 (2 H, t, J 6.1 Hz, 2-NHCOCH$_2$CH$_2$Cl), 3.92 (2 H, t, J 6.1 Hz, 6-NHCOCH$_2$CH$_2$Cl), 7.18 (1H, dd, J 1.8 Hz & 8.8 Hz, H-7), 7.48 (1 H, d, J 9.0 Hz, H-4), 7.93 (1 H, dd, J 2.4 Hz & 9.0 Hz, H-3), 8.14 (1 H, d, J 8.9 Hz, H-8), 8.20 (1 H, d, J 1.5 Hz, H-5), 8.45 (1 H, d, J 2.3 Hz, H-1), 10.23 (1 H, s, 2-NHCO), 10.47 (1 H, s, 6-NHCO), 11.71 (1 H, s, H-10).

Example 51

2,6-Bis[3-(pyrrolidino)propionamido]-9(10H)-acridone (AR-ACO-10)

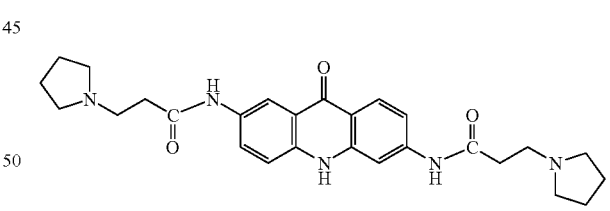

2,6-Bis(3-chloropropionamido)-9(10H)-acridone (AR-ACO-9, 3.00 g, 7.38 mmol) and KI (0.10 g, 0.60 mmol) were suspended in a mixture of dimethylformamide (45 mL) and ethanol (45 mL). Pyrrolidine (12 mL, 10.22 g, 144 mmol) was added in one lot and the whole stirred at reflux for 21 hr. The flask was cooled and all the solvents removed under reduced pressure. Dimethylformamide (100 mL) was added to the flask and this was in turn removed under reduced pressure. The process was repeated with toluene (2×100 mL) and propan-2-ol (2×100 mL). The solid in the flask was dissolved in water (60 mL) and 0.88 s.g. ammonia (10 mL) was added dropwise with stirring to yield an orange-brown precipitate. The flask was chilled with ice-water and the product collected, washed with dilute ammonia (2×10 mL, 1% dilution of 0.88 s.g. ammonia) and ice-cold water (2×10 mL). The product was dried in air and over $P_2O_5$ under vacuum to yield a yellow solid AR-ACO-10 (3.11 g, 87%).

Mp 299° C. dec., $^1$H-NMR (DMSO) δ 1.76 (8 H, m, $N(CH_2CH_2)_2$), 2.51 (8 H, m, $N(CH_2CH_2)_2$), 2.56 (4 H, t, J 6.8 Hz, $COCH_2CH_2N$), 2.74 (2 H, t, J 7.0 Hz, 2-$NHCOCH_2CH_2N$), 2.76 (2 H, t, J 7.0 Hz, 6-$NHCOCH_2CH_2N$), 7.13 (1 H, dd, J 1.7 Hz & 8.9 Hz, H-7), 7.46 (1 H, d, J 8.9 Hz, H-4), 7.92 (1 H, dd, J 2.2 Hz & 9.0 Hz, H-3), 8.12 (1 H, d, J 8.8 Hz, H-8), 8.21 (1 H, d, J 1.7 Hz, H-5), 8.43 (1 H, d, J 2.2 Hz, H-1), 10.19 (1 H, s, 2-NHCO), 10.50 (1 H, s, 6-NHCO), 11.67 (1 H, s, H-10).

Example 52

Dihydrochloride Salt (AR-ACO-11)

The dihydrochloride addition salt, AR-ACO-11, of the compound in the previous example, was also prepared by treatment with HCl.

GROUP D: 3,6,9-ACRIDINES

Example 53

2,7-Bis[3-(pyrrolidino)propionamido]-9-chloroacridine (BR-ACO-18)

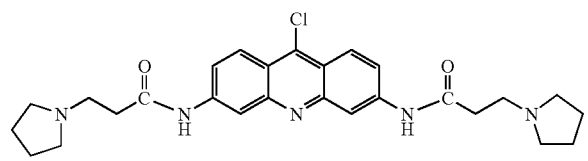

A suspension of BR-ACO-14 (5 g, 10 mmol) in $POCl_3$ (75 mL) was refluxed for 2 hr. After cooling to 0° C. the suspension was filtered and the collected solid washed with toluene (2×50 mL) and $Et_2O$ (2×100 mL). The product was collected and redissolved in $CHCl_3$ (100 mL) and washed with dilute ammonia solution (2×75 mL), brine (100 mL), dried and treated with charcoal. Evaporation under reduced pressure provided the product, BR-ACO-18, as a green brown solid.

$^1$H-NMR ($CDCl_3$) δ 1.97 (8H, m, $N(CH_2CH_2)_2$), 2.62 (4H, t, J 6.3 Hz, $COCH_2CH_2N$), 2.75 (8H, m, $N(CH_2CH_2)_2$), 2.92 (4H, t, J 6.3 Hz, $COCH_2CH_2N$), 7.97 (2H, dd, J 2.1 Hz J 9.4 Hz, H-2,7), 8.10 (2H, d, J 2.1 Hz, H-4,5), 8.33 (2H, d, J 9.4 Hz, H-1,8), 11.82 (2H, s, NHCO). m/z (EI) 494.2342 (required $C_{27}H_{33}N_5O_2Cl$ M+H 494.2323) Found: C, 64.76; H, 6.45; N, 13.93%. $C_{27}H_{32}N_5O_2Cl.0.4 H_2O$ requires C, 64.70; H, 6.601; N, 13.97%.

Example 54

9-Substitution General Procedure

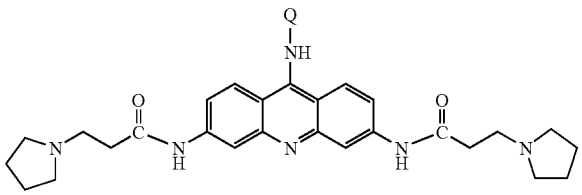

To a vigorously stirred solution of BR-ACO-18 in $CHCl_3$ was added dropwise a solution of the proposed amine, Q-$NH_2$ (e.g., $NH_2(CH_2)_pNH_2$, substituted anilines), for example, in $CHCl_3$. This solution was stirred for a further 2 hr, the solvent was then removed under reduced pressure and the resultant solid washed with EtOH and $Et_2O$ to give the desired trisubstituted derivative.

Example 55

N-{9-[4'-(N,N-Dimethylamino)phenylamino]}-3,6-bis(3-pyrrolidinopropionamido)acridine (BR-ACO-21)

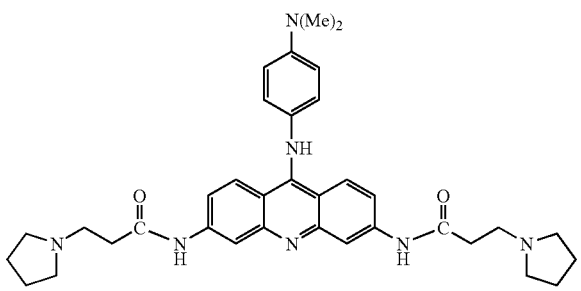

3,6-Bisamido-9-chloroacridone BR-ACO-18 (400 mg, 0.8 mmol) was treated with 4-N,N-dimethylaminoaniline (0.5 mL) according to the general procedure to give the desired product BR-ACO-21 (400 mg, 88%) as a brown solid.

Mp>320° C., $^1$H-NMR (DMSO) δ 1.81 (8 H, m, $N(CH_2CH_2)_2$), 2.81 (4 H, t, J 6.9 Hz, $COCH_2CH_2N$), 2.85 (8H, m, $N(CH_2CH_2)_2$), 3.16 (4H, t, J 6.9 Hz, $COCH_2CH_2N$), 6.67 (2H, d, J 8.7 Hz, H-2,7), 6.96 (2H, d, J 8.7 Hz, H-1,8), 7.26 (2H, d, J 8.6 Hz, H-3',5'), 8.03 (2H, d, J 8.6 Hz, H-2',6'), 8.34 (2H, s, H-4,5), 10.92 (2H, s, NHCO), m/z (EI) 594.3540 (requires $C_{35}H_{40}N_7O_2$ M+H 594.3556).

Example 56

Trihydrochloride Salt (BR-ACO-19)

The trihydrochloride addition salt, BR-ACO-19, of the compound in the previous example, was also prepared by treatment with HCl.

Example 57

N-[9-(4'-Aminophenylamino)]-3,6-bis(3-pyrrolidinopropionamido)acridine (BR-ACO-22)

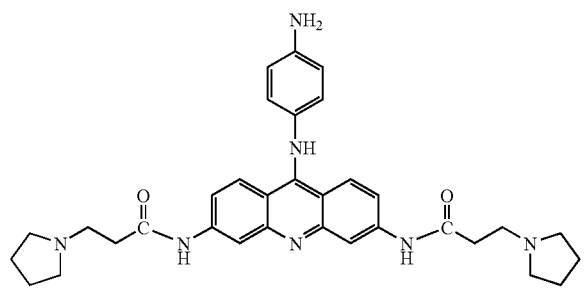

3,6-bisamido-9-chloroacridone BR-ACO-18 (400 mg, 0.8 mmol) was treated with 1,4-phenylenediamine (0.5 mL) according to the general procedure to give the desired product BR-ACO-22 (400 mg, 88%) as a brown solid.

Mp>320° C., $^1$H-NMR (DMSO) δ 1.81 (8 H, m, N(CH$_2$CH$_2$)$_2$), 2.74 (4H, t, J 6.7 Hz, COCH$_2$CH$_2$N), 2.85 (8H, m, N(CH$_2$CH$_2$)$_2$), 2.93 (6H, s, N(CH$_3$)$_2$), 3.07 (4H, t, J 6.7 Hz, COCH$_2$CH$_2$N), 6.78 (2H, d, J 8.9 Hz, H-2,7), 6.99 (2H, d, J 8.9 Hz, H-1,8), 7.20 (2H, d, J 9.1 Hz, H-3',5'), 7.97 (2H, d, J 9.1 Hz, H-2',6'), 8.24 (2H, s, H-4,5), 10.81 (2H, s, NHCO), m/z (EI) 566.3260 (requires C$_{33}$H$_{44}$N$_7$O$_2$ M+H 566.3243).

Example 58

Trihydrochloride Salt (BR-ACO-20)

The trihydrochloride addition salt, BR-ACO-20, of the compound in the previous example, was also prepared by treatment with HCl.

Example 59

N-{9-[3-(N,N-Dimethyl)aminopropylamino]}-3,6-bis(3-pyrrolidinopropionamido)acridine (JH-ACI-64)

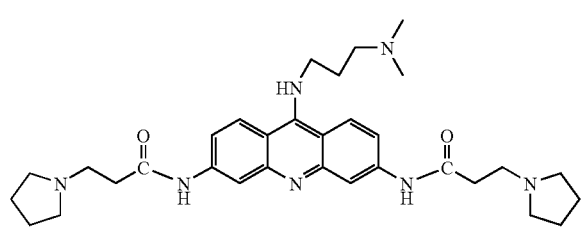

3,6-Bisamido-9-chloroacridine BR-ACO-18 (500 mg, 1.0 mmol) was treated with N,N-dimethylpropylenediamine (0.4 mL) according to the general procedure to give the desired product JH-ACI-64 (390 mg, 70%) as a pale brown solid.

$^1$H-NMR (CDCl$_3$) δ 1.86 (10 H, m, N(CH$_2$CH$_2$)$_2$, HNCH$_2$CH$_2$CH$_2$NMe$_2$), 2.29 (6 H, s, N(CH$_3$)$_2$), 2.49-2.55 (6 H, m, COCH$_2$CH$_2$N, HNCH$_2$CH$_2$CH$_2$NMe$_2$), 2.63 (8 H, m, N(CH$_2$CH$_2$)$_2$), 2.79-2.83 (4 H, m, COCH$_2$CH$_2$N), 3.74-3.78 (2 H, t, J 5.6 Hz, HNCH$_2$CH$_2$CH$_2$NMe$_2$), 7.61-7.62 (2 H, d, J 1.9 Hz, H-4,5), 7.84-7.88 (2 H, dd, J 9.3 and 1.9 Hz, H-2,7), 8.00-8.03 (2 H, d, J 9.3 Hz, H-1,8), 11.49 (2 H, s, NHCO), m/z (EI) 560.3730 (C$_{32}$H$_{46}$N$_7$O$_2$ M+H requires 560.3713).

Example 60

Tetrahydrochloride Salt (JH-ACI-65)

The tetrahydrochloride addition salt, JH-ACI-65, of the compound in the previous example, was also prepared by treatment with HCl.

Example 61

N-[9-(2-Piperidin-1-yl-ethylamino)]-3,6-bis(3-pyrrolidinopropionamido)acridine (JH-ACI-68)

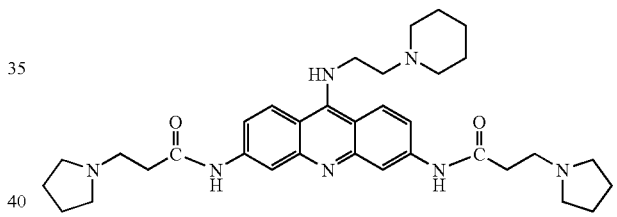

3,6-Bisamido-9-chloroacridine BR-ACO-18 (500 mg, 1.0 mmol) was treated with 1-(2-aminoethyl)piperidine (0.4 mL) according to the general procedure to give the desired product JH-ACI-68 (210 mg, 36%) as an orange solid.

$^1$H-NMR (CDCl$_3$) δ 1.54-1.56 (2 H, m, N(CH$_2$CH$_2$)$_2$CH$_2$), 1.68-1.72 (4 H, m, N(CH$_2$CH$_2$)$_2$CH$_2$), 1.94-1.96 (8 H, m, N(CH$_2$CH$_2$)$_2$), 2.43-2.44 (4 H, m, N(CH$_2$CH$_2$)$_2$CH$_2$), 2.59-2.68 (6 H, m, COCH$_2$CH$_2$N and HNCH$_2$CH$_2$N), 2.73 (8 H, m, N(CH$_2$CH$_2$)$_2$) 2.88-2.93 (4 H, m, COCH$_2$CH$_2$N), 3.85-3.89 (2 H, m, HNCH$_2$CH$_2$N), 6.76 (1 H, s, NH), 7.67 (2 H, d, J 2.0 Hz, H-4,5), 7.98-8.02 (2 H, dd, J 9.4 and 2.0 Hz, H-2,7), 8.12-8.16 (2 H, d, J 9.4 Hz, H-1,8), 11.58 (2 H, s, NHCO), m/z (EI) 586.3845 (C$_{34}$H$_{48}$N$_7$O$_2$ M+H requires 586.3869).

Example 62

Tetrahydrochloride Salt (JH-ACI-69)

The tetrahydrochloride addition salt, JH-ACI-69, of the compound in the previous example, was also prepared by treatment with HCl.

Example 63

N-{9-[3'-(Amino)phenylamino]}-3,6-bis(3-pyrrolidinopropionamido)acridine (JH-ACI-73)

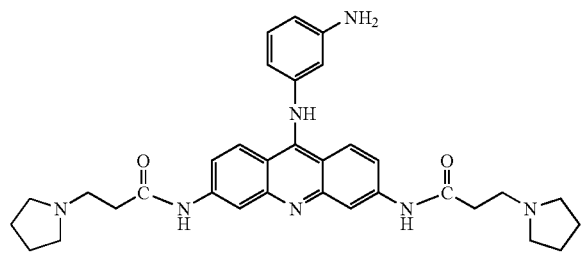

3,6-Bisamido-9-chloroacridine BR-ACO-18 (500 mg, 1.0 mmol) was treated with 1,3-phenylenediamine (0.5 mL) according to the general procedure to give the desired product JH-ACI-73 (446 mg, 78%) as an orange solid.

Mp>320° C., $^1$H-NMR (CDCl$_3$) δ 1.94 (8 H, m, N(CH$_2$CH$_2$)$_2$), 2.62 (4 H, t, J 6.5 Hz, COCH$_2$CH$_2$N), 2.72 (8 H, m, N(CH$_2$CH$_2$)$_2$), 2.89 (4 H, t, J 6.5 Hz, COCH$_2$CH$_2$N), 3.62 (2 H, sbr, NH$_2$), 6.12 (1 H, m, H-5'), 6.21 (1 H, s, H-2'), 6.34 (2 H, m, H-4',6'), 6.96 (2 H, m, H-4,5), 7.99 (4 H, m, H-1,2,7,8), m/z (EI) 566.3219 (C$_{33}$H$_{40}$N$_7$O$_2$ M+H requires 566.3243), found C, 67.07; H, 7.06, N, 16.59%. Calcd (anhydrous C$_{33}$H$_{39}$N$_7$O$_2$.1.2 mol H$_2$O) C, 67.48, H, 7.10, N, 16.69%.

Example 64

Trihydrochloride Salt (JH-ACI-74)

The trihydrochloride addition salt, JH-ACI-74, of the compound in the previous example, was also prepared by treatment with HCl.

Example 65

N-[9-(2'-(Amino)phenylamino)]-3,6-bis(3-pyrrolidinopropionamido)acridine (JH-ACI-75)

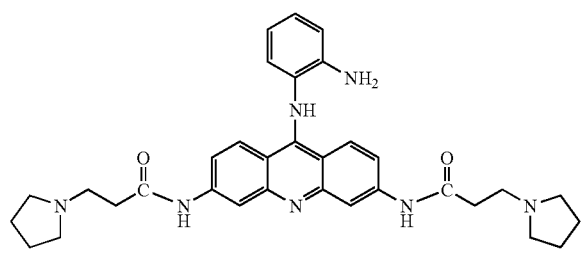

3,6-Bisamido-9-chloroacridine BR-ACO-18 (500 mg, 1.0 mmol) was treated with 1,2-phenylenediamine (0.5 mL) according to the general procedure to give the desired product JH-ACI-76 (400 mg, 88%) as an orange solid.

Mp>320° C., $^1$H-NMR (CDCl$_3$) δ 1.90 (8 H, m, N(CH$_2$CH$_2$)$_2$), 2.4 (8 H, m, N(CH$_2$CH$_2$)$_2$), 2.55 (4 H, m, COCH$_2$CH$_2$N), 2.68 (4 H, m, COCH$_2$CH$_2$N), 3.49 (2 H, sbr, NH$_2$), 6.80 (6 H, m, 4Ar—H, H-1,8), 7.95 (4 H, m, H-2,4, 5,7), m/z (EI) 566.3219 (C$_{33}$H$_{40}$N$_7$O$_2$ M+H requires 566.3243), found C, 66.67; H, 7.09, N, 16.49%. Calcd (anhydrous C$_{33}$H$_{39}$N$_7$O$_2$.1.4 mol H$_2$O) C, 67.07, H, 7.13, N, 16.59%.

Example 66

Trihydrochloride Salt (JH-ACI-76)

The trihydrochloride addition salt, JH-ACI-76, of the compound in the previous example, was also prepared by treatment with HCl.

Example 67

N-{9-[3'-(N,N-Dimethylamino)phenylamino]}-3,6-bis(3-pyrrolidinopropionamido)acridine (JH-ACI-77)

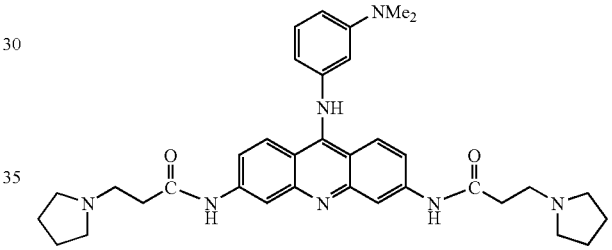

3,6-Bisamido-9-chloroacridine BR-ACO-18 (500 mg, 1.0 mmol) was treated with N,N-dimethyl-1,3-phenylenediamine (0.5 mL, freshly prepared from the hydrochloride salt) according to the general procedure to give the desired product JH-ACI-77 (400 mg, 88%) as a brown solid.

Mp>320° C., $^1$H-NMR (CDCl$_3$) δ 1.91 (8 H, m, N(CH$_2$CH$_2$)$_2$), 2.60 (4 H, m, COCH$_2$CH$_2$N), 2.67 (8 H, m, N(CH$_2$CH$_2$)$_2$), 2.88 (6 H, s, N(CH$_3$)$_2$), 2.90 (4 H, m, COCH$_2$CH$_2$N), 6.14 (1 H, d, J 7.9 Hz, H-4'), 6.30 (1 H, s, H-2'), 6.39 (1 H, d, J 8.1 Hz, H-6'), 7.11 (1 H, dd, J 7.9 Hz 8.1 Hz, H-5'), 7.9 (6 H, m, H-1,2,4,5,7,8), 11.58 (2 H, s, NHCO), m/z (EI) 594.3572 (C$_{35}$H$_{43}$N$_7$O$_2$ M+H requires 594.3556), found C, 66.62; H, 6.9, N, 15.54%. Calcd (anhydrous C$_{35}$H$_{42}$N$_7$O$_2$.2.0 mol H$_2$O) C, 66.86, H, 7.37, N, 15.59%.

Example 68

Trihydrochloride Salt (JH-ACI-78)

The trihydrochloride addition salt, JH-ACI-78, of the compound in the previous example, was also prepared by treatment with HCl

Example 69

N-[9-(Cyclohexylamino)]-3,6-bis(3-pyrrolidinopropionamido)acridine (JH-ACI-81)

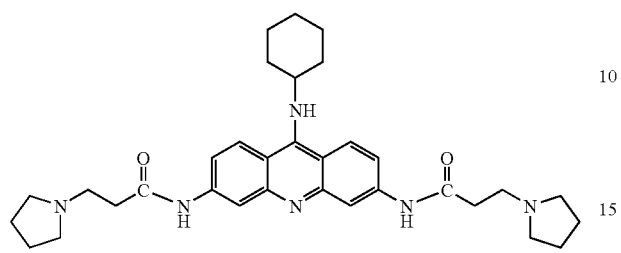

3,6-Bisamido-9-chloroacridine BR-ACO-18 (500 mg, 1.0 mmol) was treated with cyclohexylamine (0.5 mL) according to the general procedure to give the desired product JH-ACI-81 (484 mg, 86%) as yellow solid.

Mp>300° C., $^1$H-NMR (CDCl$_3$) δ 1.23 (14 H, m, CH$_2$), 1.68 (2 H, m, CH$_2$), 1.76 (4 H, m, CH$_2$), 1.92 (2 H, m, CH$_2$), 2.12 (4 H, m, CH$_2$), 2.5 (4 H, m, CH$_2$), 2.88 (4 H, m, CH$_2$), 3.06 (1 H, m, CH), 3.83 (1 H, sbr, NH), 7.78 (2 H, d, J 8.8 Hz, H-2,7), 7.96 (2 H, s, H-4,5), 7.97 (2 H, d, J 8.8 Hz, H-1,8), 11.38 (2 H, sbr, NHCO), m/z (EI) 556.3534 (C$_{33}$H$_{45}$N$_6$O$_2$ M+H requires 556.3526), found C, 68.60; H, 7.97, N, 14.54%. Calcd (anhydrous C$_{33}$H$_{44}$N$_6$O$_2$·1.2 mol H$_2$O) C, 67.48, H, 8.09, N, 14.53%.

Example 70

Trihydrochloride Salt (JH-ACI-82)

The trihydrochloride addition salt, JH-ACI-82, of the compound in the previous example, was also prepared by treatment with HCl.

Example 71

N-[9-(2-Methoxy-ethylamino)]-3,6-bis(3-pyrrolidinopropionamido)acridine (JH-ACI-85)

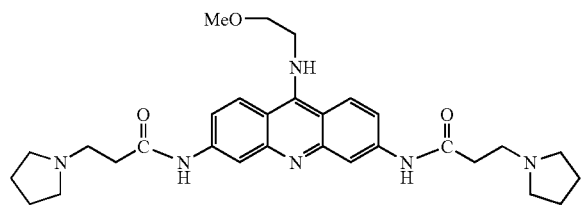

3,6-Bisamido-9-chloroacridine BR-ACO-18 (500 mg, 1.0 mmol) was treated with 2-methoxyethylamine (0.5 mL) according to the general procedure to give the desired product JH-ACI-85 (290 mg, 54%) as a brown solid.

Mp<100° C., $^1$H-NMR (DMSO) δ 1.88 (8 H, m, N(CH$_2$CH$_2$)$_2$), 2.65 (6 H, m, COCH$_2$CH$_2$N and HNCH$_2$CH$_2$OMe), 2.68 (8 H, m, N(CH$_2$CH$_2$)$_2$), 2.87-2.92 (4 H, m, COCH$_2$CH$_2$N), 47.2 (5 H, m, HNCH$_2$CH$_2$OCH$_3$), 7.59 (2 H, d, J 1.9 Hz, H-4,5), 7.94-7.99 (2 H, dd, J 9.4 and 1.9 Hz, H-2,7), 8.05-8.08 (2 H, d, J9.4 Hz, H-1,8), 11.54 (2 H, s, NHCO), m/z (EI) 533.3231 (C$_{30}$H$_{41}$N$_6$O$_3$ M+H requires 533.3240).

Example 72

Trihydrochloride Salt (JH-ACI-86)

The trihydrochloride addition salt, JH-ACI-86, of the compound in the previous example, was also prepared by treatment with HCl.

Example 73

N-[9-(Cycloheptylamino)]-3,6-bis(3-pyrrolidinopropionamido)acridine (JH-ACI-87)

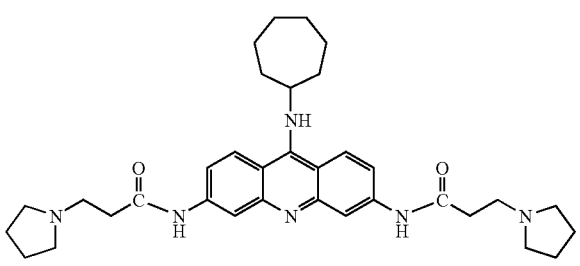

3,6-Bisamido-9-chloroacridine BR-ACO-18 (500 mg, 1.0 mmol) was treated with cycloheptylamine (0.5 mL) according to the general procedure to give the desired product JH-ACI-87 (485 mg, 84%) as a yellow solid.

Mp>320° C., $^1$H-NMR (CDCl$_3$) δ 1.62 (16 H, m, CH$_2$), 2.1 (4 H, m, CH$_2$), 2.43 (4 H, m, CH$_2$), 2.55 (4 H, m, J 5.0 Hz, CH$_2$), 2.70 (4 H, m, J 5.0 Hz, CH$_2$), 2.92 (1 H, t, J 5.1 Hz, CH), 4.08 (1 H, sbr, NH), 7.92 (2 H, m, H-2,7), 8.33 (4 H, m, H-1,4,5,8), m/z (EI) 571.3735 (C$_{34}$H$_{47}$N$_6$O$_2$ M+H requires 571.3761).

Example 74

Trihydrochloride Salt (JIH-ACI-88)

The trihydrochloride addition salt, JH-ACI-88, of the compound in the previous example, was also prepared by treatment with HCl.

Example 75

N-[9-(4'-Acetylphenylamino)]-3,6-bis(3-pyrrolidinopropionamido)acridine (JH-ACI-89)

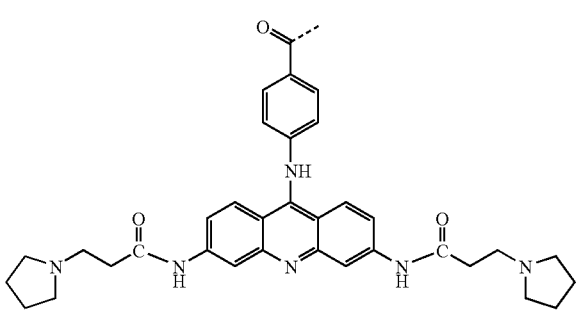

3,6-Bisamido-9-chloroacridine BR-ACO-18 (500 mg, 1.0 mmol) was treated with 4-aminoacetophenone (0.5 mL)

according to the general procedure to give the desired product JH-ACI-89 (400 mg, 88%) as an orange solid; Mp>320° C., $^1$H-NMR (CDCl$_3$) δ 1.69 (8 H, m, N(CH$_2$CH$_2$)$_2$), 2.18 (7 H, m, COCH$_2$CH$_2$N, COCH$_3$), 2.51 (8 H, m, N(CH$_2$CH$_2$)$_2$), 2.76 (4 H, m, COCH$_2$CH$_2$N), 6.81 (2 H, d, J 7.9 Hz, 2-ArH), 6.90 (2 H, d, J 7.9 Hz, 2-ArH), 7.88 (2 H, d, H-2,7), 8.10 (4 H, m, H-1,4,5,8), 10.36 (2 H, sbr, NHCO), m/z (EI) 566.3219 (C$_{33}$H$_{40}$N$_7$O$_2$ M+H requires 566.3243), found C, 67.07; H, 7.06, N, 16.59%. Calcd (anhydrous C$_{33}$H$_{39}$N$_7$O$_2$.1.2 mol H$_2$O) C, 67.48, H, 7.10, N, 16.69%.

Example 76

Trihydrochloride Salt (JH-ACI-90)

The trihydrochloride addition salt, JH-ACI-90, of the compound in the previous example, was also prepared by treatment with HCl.

Example 77

N-[9-(N,N-Dimethylethylenediamino)]-3,6-bis(3-pyrrolidinopropionamido)acridine (BSU-SB-36/152)

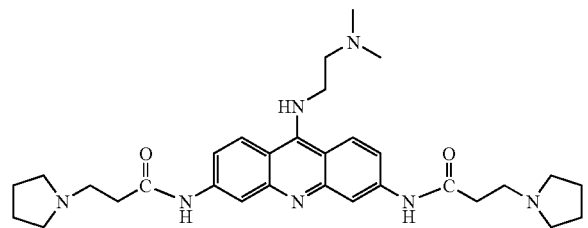

3,6-Bisamido-9-chloroacridine BR-ACO-18 (500 mg, 1.0 mmol) was treated with N,N-dimethylethylenediamine (0.03 mL) according to the general procedure to give the desired product BSU-SB-36/152 (370 mg, 67%) as a yellow solid.

$^1$H-NMR (CDCl$_3$) δ 1.88-1.95 (8 H, m, N(CH$_2$CH$_2$)$_2$), 2.42 (6 H, s, N(CH$_3$)$_2$), 2.58-2.68 (6 H, m, COCH$_2$CH$_2$N and HNCH$_2$CH$_2$NMe$_2$), 2.72 (8 H, m, N(CH$_2$CH$_2$)$_2$), 2.87-2.92 (4 H, m, COCH$_2$CH$_2$N), 4.06-4.10 (2 H, t, J 5.6 Hz, HNCH$_2$CH$_2$NMe$_2$), 7.59 (2 H, d, J 1.9 Hz, H-4,5), 7.94-7.99 (2 H, dd, J 9.4 and 1.9 Hz, H-2,7), 8.05-8.08 (2 H, d, J9.4 Hz, H-1,8), 11.54 (2 H, s, NHCO), m/z (EI) 546.3570 (C$_{31}$H$_{44}$N$_7$O$_2$ M+H requires 546.3556).

Example 78

Tetrahydrochloride Salt (SB-ACI-11)

The tetrahydrochloride addition salt, SB-ACI-11, of the compound in the previous example, was also prepared by treatment with HCl.

Example 79

N-{9-[2-(2'-Aminoethyl)-1-methylpyrrolidino]}-3,6-bis(3-pyrrolidinopropionamido)acridine (BSU-SB-36/158)

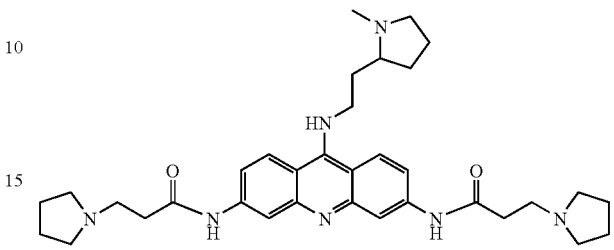

3,6-Bisamido-9-chloroacridine BR-ACO-18 (0.5 mg, 1.0 mmol) was treated with 2-(2-aminoethyl)-1-methylpyrrolidine (0.43 mL) according to the general procedure to give the desired product BSU-SB-36/158 (380 mg, 64%) as a yellow solid.

$^1$H-NMR (CDCl$_3$) δ 1.76-1.89 (4 H, m, MeN (CH$_2$CH$_2$CH$_2$CH—), 1.96 (10 H, m, N(CH$_2$CH$_2$)$_2$ and HNCH$_2$CH$_2$—), 2.08-2.28 (2 H, m, MeN (CH$_2$CH$_2$CH$_2$CH—), 2.51 (3 H, s, NCH$_3$), 2.58-2.63 (4 H, t, J 5.3 Hz, COCH$_2$CH$_2$N), 2.72, (8 H, m, COCH$_2$CH$_2$N), 2.88-2.92 (4 H, m, t, J 5.3 Hz, COCH$_2$CH$_2$N), 3.23-3.29 (1 H, m, MeN(CH$_2$CH$_2$CH$_2$CH—), 4.09-4.20 (2 H, m, HNCH$_2$CH$_2$—), 7.58-7.59 (2 H, d, J 2.0 Hz, H-4,5), 7.96-8.02 (2 H, m, H-2,7), 8.05-8.09 (2 H, m, J 9.4 Hz, H-1,8), 8.39 (1 H, s, NH), 11.55 (2 H, s, NHCO), m/z (EI) 586.3840, (C$_{34}$H$_{48}$N$_7$O$_2$ M+H requires 586.3869).

Example 80

Tetrahydrochloride Salt (SB-ACI-12)

The tetrahydrochloride addition salt, SB-ACI-12, of the compound in the previous example, was also prepared by treatment with HCl.

Example 81

N-[9-(Pyridin-3'-yl-methylamino)]-3,6-bis(3-pyrrolidinopropionamido)acridine (BSU-SB-36/160)

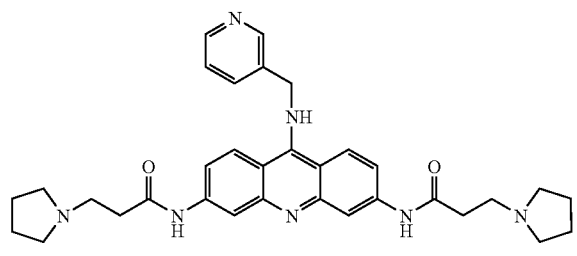

3,6-Bisamido-9-chloroacridine BR-ACO-18 (500 mg, 1.0 mmol) was treated with pyridin-3-yl-methylamine (0.31 mL) according to the general procedure to give the desired product BSU-SB-36/160 (220 mg, 39%) as a yellow solid.

$^1$H-NMR (CDCl$_3$) δ 1.85 (8 H, m, N(CH$_2$CH$_2$)$_2$), 2.48-2.53 (4 H, dd, J 5.3 and 6.0 Hz, COCH$_2$CH$_2$N), 2.63 (8 H, m, N(CH$_2$CH$_2$)$_2$), 2.78-2.83 (4 H, dd, J 5.3 and 6.0 Hz, COCH$_2$CH$_2$N), 4.91 (2 H, s, HNCH$_2$Aryl), 7.18-7.23 (1 H, m, H-5'), 7.62-7.65 (3 H, m, H-2,7), 7.76 (2 H, m, H-4,5), 7.91-7.95 (2 H, d, J 9.2 Hz, H-1,8), 8.49-8.50 (2 H, m, H-4',6'), 8.62 (1 H, s, H-2'), 11.57 (2 H, s, NHCO), m/z (EI) 566.3226, (requires C$_{33}$H$_{40}$N$_7$O$_2$ M+H 566.3243).

Example 82

Tetrahydrochloride Salt (SB-ACI-13)

The tetrahydrochloride addition salt, SB-ACI-13, of the compound in the previous example, was also prepared by treatment with HCl.

Example 83

N-{9-[(3'-Acetamido)aminophenyl]}-3,6-bis(3-pyrrolidinopropionamido)acridine (BSU-SB-36/164)

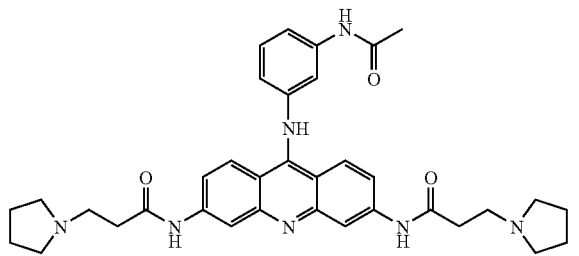

3,6-Bisamido-9-chloroacridine BR-ACO-18 (500 mg, 1.0 mmol) was treated with N-(3-amino-phenyl)-acetamide (0.5 g) according to the general procedure to give the desired product BSU-SB-36/164 (430 mg, 70%) as a yellow solid.

$^1$H-NMR (DMSO) δ 1.89-2.07 (11 H, m, N(CH$_2$CH$_2$)$_2$ and CH$_3$), 3.05-3.10 (8 H, m, N(CH$_2$CH$_2$)$_2$), 3.39-3.53 (8 H, m, COCH$_2$CH$_2$N), 6.97-7.00 (1 H, d, J 7.8 Hz, H-6'), 7.34-7.39 (1 H, t, J 7.8 Hz, H-5'), 7.43-7.47 (2 H, d, J 9.4 Hz, H-2,7), 7.51-7.54 (1 H, d, J 7.8 Hz, H-4'), 7.79 (1 H, s, H-2'), 8.11-8.15 (2 H, d, J 9.4 Hz, H-1, 8), 8.50 (2 H, s, H-4, 5), 10.35 (1 H, s, NH), 11.07 (2 H, s, NH), 11.17 (1 H, s, NH), 11.38 (2 H, s, NH), 14.08 (1 H, s, NH).

Example 84

Tetrahydrochloride Salt (SB-ACI-14)

The tetrahydrochloride addition salt, SB-ACI-14, of the compound in the previous example, was also prepared by treatment with HCl.

Example 85

N-[9-(Cyclopropylamino)]-3,6-bis(3-pyrrolidinopropionamido)acridine (JM-ACI-13)

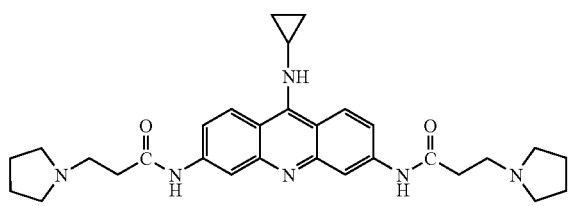

3,6-Bisamido-9-chloroacridine BR-ACO-18 (300 mg, 0.6 mmol) was treated with cycloprypylamine (0.43 g, 1.8 mmol) according to the general procedure to give the desired product JM-ACI-13 (290 mg, 70%) as a yellow solid.

Mp>320° C., $^1$H-NMR (DMSO) δ 0.36 (2 H, m, CH$_2$), 0.39 (2 H, m, CH$_2$), 1.70 (8 H, m, N(CH$_2$CH$_2$)$_2$), 2.55 (4 H, m, COCH$_2$CH$_2$N), 2.58 (8 H, m, N(CH$_2$CH$_2$)$_2$), 2.84 (4 H, m, COCH$_2$CH$_2$N), 2.90 (1 H, m, CH), 7.02 (2 H, m, H-1,8), 7.9 (2 H, m, H-4,5), 8.2 (2 H, m, H-2,7) 10.00 (1 H, s, NHCO), 10.28(2 H, s, NHCO), m/z (EI) 515.3160 (C$_{30}$H$_{39}$N$_6$O$_2$ M+H requires 515.3134).

Example 86

Trihydrochloride Salt (JM-ACI-14)

The trihydrochloride addition salt, JM-ACI-14, of the compound in the previous example, was also prepared by treatment with HCl.

Example 87

N-{9-[4'-(3-Pyrrolidin-1-yl-propionylamino)-phenylamino]}-3,6-bis(3-pyrrolidinopropionamido)acridine (JC-ACI-9a)

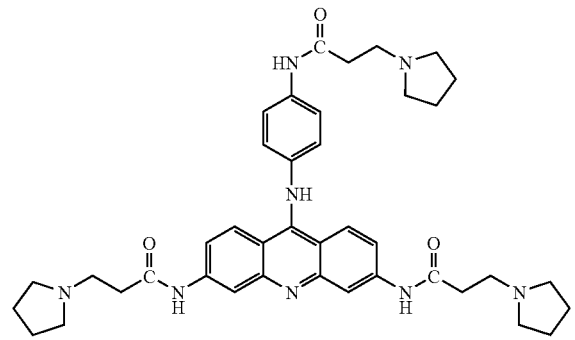

3,6-Bisamido-9-chloroacridine BR-ACO-18 (300 mg, 0.6 mmol) was treated with N-(4-aminophenyl)-3-pyrrolidin-1-yl-propionamide (0.43 g, 1.8 mmol) according to the general procedure to give the desired product JC-ACI-9a (290 mg, 70%) as an orange solid.

Mp 147-149° C., $^1$H-NMR (DMSO) δ 1.74 (12 H, m, N(CH$_2$CH$_2$)$_2$), 2.59 (18H, m, COCH$_2$CH$_2$N and N(CH$_2$CH$_2$)$_2$), 2.77 (6H, t, J 6.7 Hz, COCH$_2$CH$_2$N), 6.72 (2 H, d, J 8.6 Hz, H-3',5'), 6.97 (2 H, m, H-1,8), 7.54 (2 H, d, J 8.6 Hz, H-2',6'); 7.98 (4 H, m, H-2,7 and H-4,5), 10.01 (1 H, s, NH), 10.36 (3 H, s, NHCO). Elemental analysis found for C$_{46}$H$_{50}$N$_8$O$_3$—H$_2$O: C, 67.56; H, 7.32; N, 15.48; requires: C, 67.77; H, 7.39; N, 15.81; m/z (EI) 691.4070 (C$_{40}$H$_{51}$N$_7$O$_2$ M+H requires 691.4084).

Example 88

Trihydrochloride Salt (JC-ACI-9)

The trihydrochloride addition salt, JC-ACI-9, of the compound in the previous example was also prepared by treatment with HCl.

Example 89

N-{9-[4'-Fluorophenylamino]}-3,6-bis(3-pyrrolidinopropionamido)acridine (JC-ACI-3a)

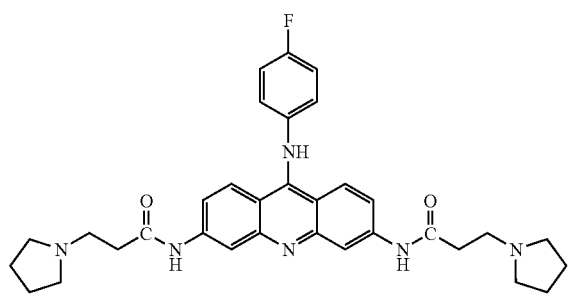

3,6-Bisamido-9-chloroacridine BR-ACO-18 (500 mg, 1.0 mmol) was treated with 4-fluoroaniline (0.3 mL) according to the general procedure to give the desired product JC-ACI-3a (650 mg, 71%) as a red solid.

$^1$H-NMR (CDCl$_3$) δ 1.89 (8 H, bs, N(CH$_2$CH$_2$)$_2$), 2.59 (4 H, t, J 5.5 Hz, COCH$_2$CH$_2$N), 2.68 (8 H, bs, N(CH$_2$CH$_2$)$_2$), 2.86 (4 H, t, J 5.5 Hz, COCH$_2$CH$_2$N), 6.80 (4 H, m, H-2,7 and H-3',5'), 6.98 (4 H, m, H-1,8 and H-2',6'), 8.02 (2H, s, H-4,5), 11.57 (2H, s, NHCO), m/z (EI) 569.3056 (C$_{33}$H$_{39}$FN$_6$O$_2$M+H requires 569.3040).

Example 90

Trihydrochloride Salt (JC-ACI-3)

The trihydrochloride addition salt, JC-ACI-3, of the compound in the previous example was also prepared by treatment with HCl.

Example 91

N-{9-[2'-(Methylsulfanyl)phenylamino]}-3,6-bis(3-pyrrolidinopropionamido)acridine (JC-ACI-4a)

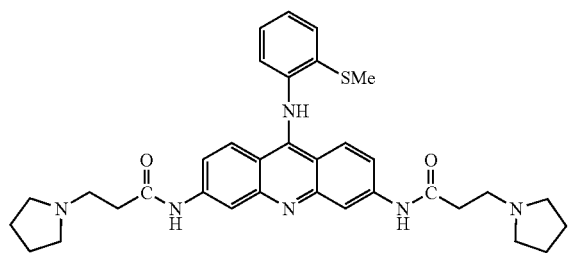

3,6-Bisamido-9-chloroacridine BR-ACO-18 (500 mg, 1.0 mmol) was treated with 2-(methylthio)aniline (0.2 mL) according to the general procedure to give the desired product JC-ACI-4a (650 mg, 71%) as an red solid.

Mp>320° C., $^1$H-NMR (DMSO) δ 1.9 (8 H, m, N(CH$_2$CH$_2$)$_2$), 2.39 (3 H, s, SMe), 2.42 (8 H, m, N(CH$_2$CH$_2$)$_2$), 2.56 (4 H, m, COCH$_2$CH$_2$N), 2.84 (4 H, m, COCH$_2$CH$_2$N), 6.14 (1 H, d, J 7.9 Hz, H-4'), 6.30 (1 H, s, H-2'), 6.39 (1 H, d, J 8.1 Hz, H-6'), 7.11 (1 H, dd, J 7.9 Hz 8.1 Hz, H-5'), 7.9 (6 H, m, H-1,2,4,5,7,8), 11.58 (2 H, s, NHCO), m/z (EI) 597.3035, (C$_{34}$H$_{41}$N$_6$O$_2$ M+H requires 597.3012).

Example 92

Trihydrochloride Salt (JC-ACI-4)

The trihydrochloride addition salt, JC-ACI-4, of the compound in the previous example was also prepared by treatment with HCl.

Example 93

N-{9-[3'-Methylsulfanyl-phenylamino]}-3,6-bis(3-Pyrrolidinopropionamido)acridine (JC-ACI-5a)

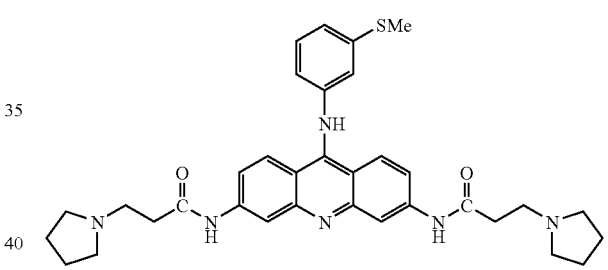

3,6-Bisamido-9-chloroacridine BR-ACO-18 (800 mg, 1.6 mmol) was treated with 3-(methylthio)aniline (0.4 ml) according to the general procedure to give the desired product JC-ACI-5a (650 mg, 71%) as an red solid.

Mp>320° C., $^1$H-NMR (DMSO) δ 1.9 (8 H, m, N(CH$_2$CH$_2$)$_2$), 2.39 (3 H, s, SMe), 2.42 (8 H, m, N(CH$_2$CH$_2$)$_2$), 2.56 (4 H, m, COCH$_2$CH$_2$N), 2.84 (4 H, m, COCH$_2$CH$_2$N), 6.61 (1 H, m, H-4'), 6.79 (1 H, s, H-2'), 6.85 (1 H, m, H-6'), 7.10 (3 H, m, H-1,8, H-5'), 7.95 (4 H, m, H-2,4,5,7), 11.37 (2 H, S. NHCO), m/z (EI) 597.3035 (C$_{34}$H$_{41}$N$_6$O$_2$ M+H requires 597.3012).

Example 94

Trihydrochloride Salt (JC-ACI-5)

The trihydrochloride addition salt, JC-ACI-5, of the compound in the previous example was also prepared by treatment with HCl.

Example 95

9-Chloro-3,6-bis[(1,3,3-trimethyl-6-azabicyclo[3.2.1]-octanamino)propionamido]-acridine (JH-ACI-33)

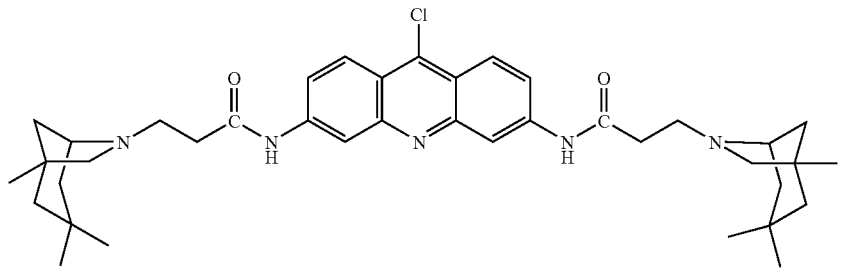

A suspension of the 3,6-bisamido-9(10H)-acridone JH-ACO-31 (4.0 g, 6.25 mmol) in POCl$_3$ (75 mL) was refluxed for 2 hr, after cooling to 0° C. the suspension was filtered and the collected solid washed with toluene (2×50 mL), and Et$_2$O (2×100 mL). The product was collected and dissolved in CHCl$_3$ (100 mL) and washed with dilute ammonia solution (2×75 mL), brine (100 mL), dried and treated with charcoal. Evaporation under reduced pressure provided JH-ACI-31 (3.1 g, 77%) as a yellow/green solid.

$^1$H-NMR (CDCl$_3$) δ 0.88 (6H, s, CH$_3$), 1.08 (6H, s, CH$_3$), 1.35 (4H, m, CH$_2$) 1.47 (6H, s, CH$_3$), 1.52 (4H, m, CH$_2$), 1.65-1.75 (4H, m, CH$_2$), 2.22 (2H, m, CH), 2.48 (4H, m, COCH$_2$), 2.80-2.89 (4H, m, COCH$_2$CH$_2$N), 2.92 (6 H, s, N(CH$_3$)$_2$), 3.20-3.30 (4H, m, CH$_2$), 7.97 (2H, d, J 9.4 Hz, H-2,7), 8.10 (2H, s, H-4,5), 8.33 (2H, d, J 9.4 Hz, H-1,8), 11.82 (2H, s, NHCO).

Example 96

N-{9-[4'-(Amino)phenylamino]}-3,6-bis[(1,3,3-trimethyl-6-azabicyclo[3.2.1]-octanamino)propionamido]-acridine (JH-ACI-100)

3,6-Bisamido-9-chloroacridine JH-ACI-33 (1.0 g, 1.5 mmol) was treated 1,4-phenylenediamine (700 mg) according to the general procedure to give the desired product JH-ACI-100 (500 mg, 45%) as a brown solid.

NMR (DMSO) δ 0.84 (6H, s, CH$_3$), 1.02 (6H, s, CH$_3$), 1.25 (4H, m, CH$_2$) 1.07 (6H, s, CH$_3$), 1.21 (4H, m, CH$_2$), 1.34 (4H, m, CH$_2$), 2.34 (2H, m, CH), 2.63 (4H, t, COCH$_2$), 3.07 (4H, m, COCH$_2$CH$_2$N), 3.20-3.30 (4H, m, CH$_2$), 5.48 (2 H, sbr, NH$_2$), 6.66 (2 H, d, J 8.0 Hz, ArH-3'5'), 7.05 (2 H, d, J 8.0 Hz, ArH-2'6'), 7.31 (2 H, d, J 7.7 Hz, H-1,8), 8.06 (2 H, d, J 7.7 Hz, H-2,7), 8.4 (2 H, s, H-4,5), 10.88 (2 H, s, NHCO), 10.76 (2 H, s, NHCO), m/z [EI] (relative intensity %) 731 ([M+H], 100), 577 (M–C$_{10}$H$_{18}$N, 10), 522 (M–C$_{13}$H$_{23}$NO, 15), 316 (M–C$_{26}$H$_{46}$N$_2$O$_2$, 11).

Example 97

Trihydrochloride Salt (JH-ACI-101)

The trihydrochloride addition salt, JH-ACI-101, of the compound in the previous example, was also prepared by treatment with HCl.

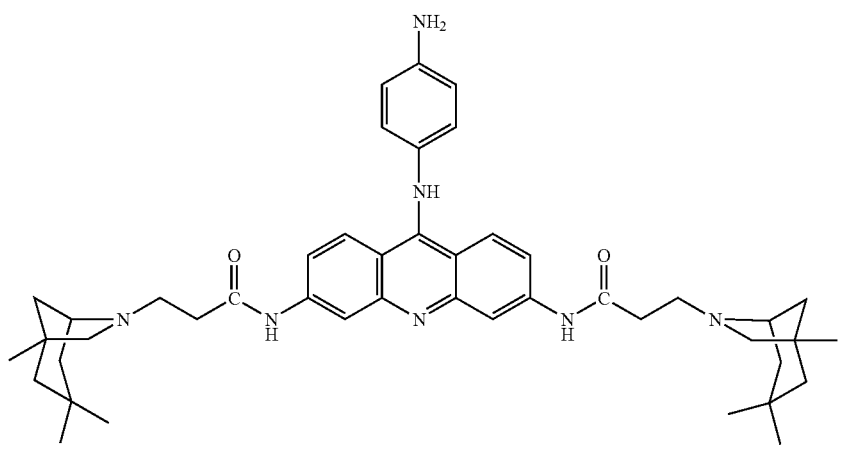

Example 98

N-{9-[4'-(N,N-Dimethylamino)phenylamino]}-3,6-bis[(1,3,3-trimethyl-6-azabicyclo[3.2.1]-octanamino) propionamido]-acridine (JH-ACI-102)

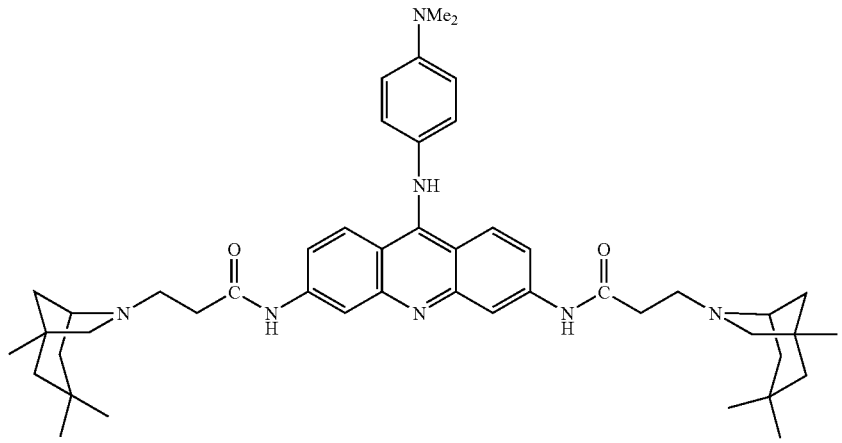

3,6-Bisamido-9-chloroacridine JH-ACI-33 (1.0 g, 1.5 mmol) was treated N,N-dimethyl-1,4-phenylenediamine (700 mg) according to the general procedure to give the desired product JH-ACI-102 (715 mg, 62%) as a brown solid.

Mp>300° C. $^1$H-NMR (CDCl$_3$) δ 0.88 (6H, s, CH$_3$), 1.08 (6H, s, CH$_3$), 1.35 (4H, m, CH$_2$) 1.47 (6H, s, CH$_3$), 1.52 (4H, m, CH$_2$), 1.65-1.75 (4H, m, CH$_2$), 2.22 (2H, m, CH), 2.48 (4H, m, COCH$_2$), 2.80-2.89 (4H, m, COCH$_2$CH$_2$N), 2.92 (6 H, s, N(CH$_3$)$_2$), 3.20-3.30 (4H, m, CH$_2$), 6.73 (2 H, d, J 8.8 Hz, H-3',5'), 6.86 (2 H, d, J 8.8 Hz, H-2',6'), 7.97 (6 H, m, H-1,2,4,5,7,8), 10.76 (2 H, s, NHCO), m/z [EI] (relative intensity %) 759 ([M+H], 100), 605 (M−C$_{10}$H$_{19}$N, 25), 577 (22), 551 (M−C$_{13}$H$_{22}$NO, 23), 453 (M−C$_{20}$H$_{36}$N$_2$, 10), 370 (M−C$_{25}$H$_{41}$N$_2$O).

Example 99

Trihydrochloride Salt (JH-ACI-103)

The trihydrochloride addition salt, JH-ACI-103, of the compound in the previous example, was also prepared by treatment with HCl.

GROUP E: 2,7,9-ACRIDINES

Example 100

9-Chloro-2,7-bis(3-pyrrolidinopropionamido)acridine (JM-ACI-43)

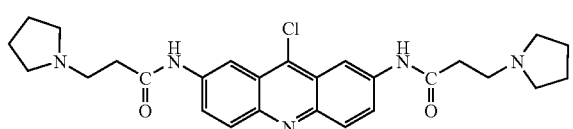

2,7-Bisamidoacridone BR-ACO-16 (1 g, 2.1 mmol) was treated with refluxing POCl$_3$ for 3 hr. The reaction was cooled, and anhydrous diethyl ether was added to precipitate product. Solids were filtered from solution to give the desired product JM-ACI-43 (750 mg, 72%) as a yellow solid.

Mp>320° C., $^1$H-NMR (CDCl$_3$) δ 1.91 (8 H, m, N(CH$_2$CH$_2$)$_2$), 2.56 (4 H, t, J 5.8 Hz, COCH$_2$CH$_2$N), 2.69 (8 H, m, N(CH$_2$CH$_2$)$_2$), 2.86 (4 H, t, J 5.8 Hz, COCH$_2$CH$_2$N), 7.64 (2 H, dd, J 9.3 Hz, J 2.0 Hz, H-3,6), 8.05 (2 H, d, J 9.3 Hz, H-4,5), 8.64 (2 H, d, J 2.0 Hz, H-1,8), 11.78 (2 H, s, NHCO), m/z (EI) 494.2342 (C$_{27}$H$_{33}$ClN$_5$O$_2$ M+H requires 494.2323).

Example 101

N-[9-(4'-Methoxyphenylamino)]-2,7-bis(3-pyrrolidinopropionamido)acridine (JM-ACI-10)

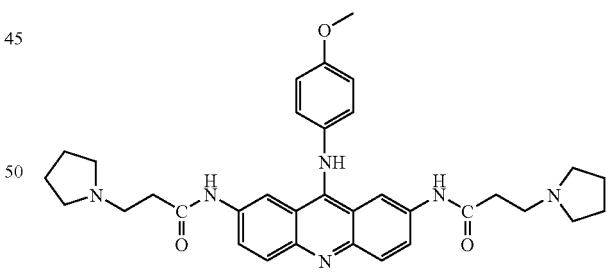

2,7-Bisamido-9-chloroacridine BR-ACO-16 (150 mg, 0.3 mmol) was treated with p-anisidine (0.5 mL) according to the general procedure to give the desired product JM-ACI-10 (100 mg, 52%) as a bright orange solid.

Mp>320° C., $^1$H-NMR (DMSO) δ 1.66 (8 H, m, N(CH$_2$CH$_2$)$_2$), 2.50 (12 H, m, COCH$_2$CH$_2$N, N(CH$_2$CH$_2$)$_2$), 2.71 (4 H, t, J 6.8 Hz, COCH$_2$CH$_2$N ), 3.65 (3 H, s, OCH$_3$), 6.62 (2 H, d, J 8.6 Hz, H-3',5'), 6.74 (2 H, d, J 8.6 Hz, H-2',6'), 7.92 (2 H, m, J 9.3 Hz, H-3,6), 8.01 (2 H, d, J 9.3 Hz, H-4,5), 8.33 (2 H, m, H-1,8), 10.36 (2 H, s, NHCO), m/z (EI) 581.3260 (C$_{34}$H$_{41}$N$_6$O$_3$ M+H requires 581.3240).

Example 102

Trihydrochloride Salt (JM-ACI-11)

The trihydrochloride addition salt, JM-ACI-10, of the compound in the previous example, was also prepared by treatment with HCl.

Example 103

N-[9-(2'-Aminophenylamino)]-2,7-bis(3-pyrrolidino-propionamido)acridine (JM-ACI-29)

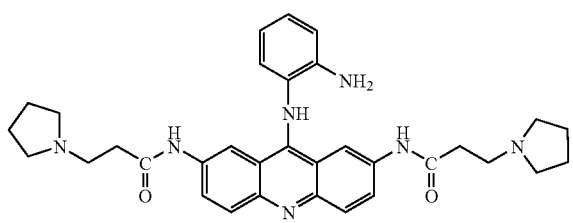

2,7-Bisamido-9-chloroacridine BR-ACO-16 (150 mg, 0.3 mmol) was treated with 1,2-phenylenediamine (70 mg) according to the general procedure to give the desired product JM-ACI-29 (90 mg, 53%) as a dark red solid.

Mp>320° C., $^1$H-NMR (CDCl$_3$) δ 1.79 (8 H, m, N(CH$_2$CH$_2$)$_2$), 2.46 (4 H, t, J 5.8 Hz, COCH$_2$CH$_2$N), 2.58 (8 H, m, N(CH$_2$CH$_2$)$_2$), 2.77 (4 H, t, J 5.8 Hz, COCH$_2$CH$_2$N), 6.39 (1 H, m, H-1'), 6.48 (1 H, m, H-4'), 6.82 (2 H, m, H-1',2'), 7.55 (2 H, dd, J 9.3 Hz, J 2.3 Hz, H-3,6), 7.98 (2 H, d, J 9.3 Hz, H-4,5), 8.18 (2 H, d, J 2.3 Hz, H-1,8), 11.26 (2 H, s, NHCO), m/z (EI) 566.3219 (C$_{33}$H$_{40}$N$_7$O$_2$ M+H requires 566.3243).

Example 104

Trihydrochloride Salt (JM-ACI-30)

The trihydrochloride addition salt, JM-ACI-29, of the compound in the previous example, was also prepared by treatment with HCl.

Example 105

N-[9-(3'-Aminophenylamino)]-2,7-bis(3-pyrrolidino-propionamido)acridine (JM-ACI-31)

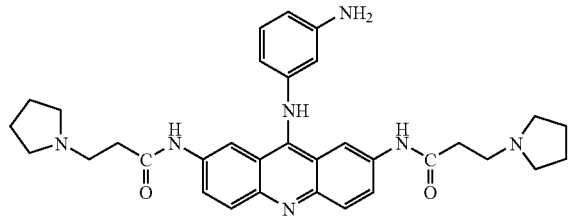

2,7-Bisamido-9-chloroacridine BR-ACO-16 (150 mg, 0.3 mmol) was treated with 1,3-phenylenediamine (70 mg) according to the general procedure to give JM-ACI-31 (100 mg, 59%) as brown solid.

Mp>320° C., $^1$H-NMR (CDCl$_3$) δ 1.75 (8 H, m, N(CH$_2$CH$_2$)$_2$), 2.45 (4 H, t, J 5.8 Hz, COCH$_2$CH$_2$N), 2.56 (8 H, m, N(CH$_2$CH$_2$)$_2$), 2.76 (4 H, t, J 5.8 Hz, COCH$_2$CH$_2$N), 5.96 (1 H, s, H-2'), 6.04 (1 H, d, J 7.4 Hz, H-4'), 6.12 (1 H, d, J 8.6 Hz, H-6'), 6.85 (2 H, dd, J 8.6 Hz, J 5.75 Hz, H-5'), 7.69 (2 H, dd, J 9.3 Hz, J 2.25 Hz, H-3,6), 8.00 (2 H, d, J 9.3 Hz, H-4,5), 8.12 (2 H, d, J 2.3 Hz, H-1,8), 11.52 (2 H, s, NHCO), m/z (EI) 566.3249 (C$_{33}$H$_{40}$N$_7$O$_2$ M+H requires 566.3243).

Example 106

Trihydrochloride Salt (JM-ACI-32)

The trihydrochloride addition salt, JM-ACI-31, of the compound in the previous example, was also prepared by treatment with HCl.

Example 107

N-{9-[3'-(N,N-Dimethylamino)phenylamino]}-2,7-bis(3-pyrrolidinopropionamido)acridine (JM-ACI-33)

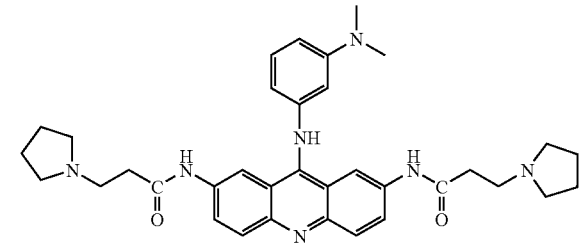

2,7-Bisamido-9-chloroacridine BR-ACO-16 (150 mg, 0.3 mmol) was treated with N,N-dimethyl-1,3-phenylenediamine (85 mg) according to the general procedure to give the desired product JM-ACI-33 (70 mg, 39%) as a dark brown solid.

Mp>320° C., $^1$H-NMR (CDCl$_3$) δ 1.75 (8 H, m, N(CH$_2$CH$_2$)$_2$), 2.53 (4 H, t, J 6.0 Hz, COCH$_2$CH$_2$N), 2.64 (8 H, m, N(CH$_2$CH$_2$)$_2$), 2.75 (6 H, s, N(CH$_2$)$_2$), 2.85 (4 H, t, J 6.0 Hz, COCH$_2$CH$_2$N), 6.04 (1 H, m, J 7.8 Hz, H-4'), 6.23 (2 H, m, H-2',6'), 6.92 (1 H, dd, J 7.3 Hz, J 7.3 Hz, H-5'), 7.81 (2 H, dd, J 9.3 Hz, J 2.3 Hz, H-3,6), 8.02 (2 H, d, J 9.3 Hz, H-4,5), 8.10 (2 H, d, J 2.3 Hz, H-1,8), 11.28 (2 H, s, NHCO), m/z (EI) 594.3572 (C$_{35}$H$_{44}$N$_7$O$_2$ M+H requires 594.3556).

Example 108

Trihydrochloride Salt (JM-ACI-34)

The trihydrochloride addition salt, JM-ACI-33, of the compound in the previous example, was also prepared by treatment with HCl.

Example 109

N-[9-(4'-Aminoyphenylamino)]-2,7-bis(3-pyrrolidinopropionamido)acridine (JM-ACI-35)

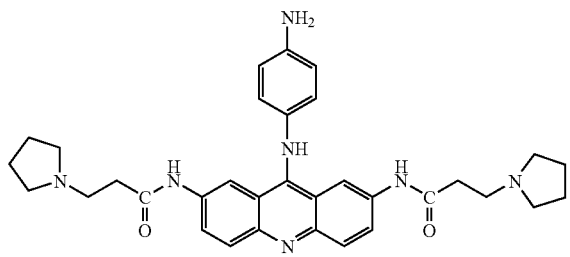

2,7-Bisamido-9-chloroacridine BR-ACO-16 (150 mg, 0.3 mmol) was treated with 1,4-phenylenediamine (70 mg) according to the general procedure to give the desired product JM-ACI-35 (55 mg, 32%) as a dark red solid.

Mp>320° C., $^1$H-NMR (CDCl$_3$) δ 1.79 (8 H, m, N(CH$_2$CH$_2$)$_2$), 2.45 (4 H, t, J 6.0 Hz, COCH$_2$CH$_2$N), 2.57 (8 H, m, N(CH$_2$CH$_2$)$_2$), 2.76 (4 H, t, J 6.0 Hz, COCH$_2$CH$_2$N), 6.48 (2H, d, J 8.8 Hz, H-3',5'), 6.66 (2H, d, J 8.8 Hz, H-2',6'), 7.60 (2 H, dd, J 9.0 Hz, J 2.3 Hz, H-3,6), 7.98 (2 H, d, J 9.0 Hz, H-4,5), 8.19 (2 H, d, J 2.3 Hz, H-1,8), 11.43 (2 H, s, NHCO), m/z (EI) 566.3225 (C$_{33}$H$_{40}$N$_7$O$_2$ M+H requires 566.3243).

Example 110

Trihydrochloride Salt (JM-ACI-36)

The trihydrochloride addition salt, JM-ACI-35, of the compound in the previous example, was also prepared by treatment with HCl.

Example 111

N-{9-[4'-(N,N-dimethylamino)phenylamino]}-2,7-bis(3-pyrrolidinopropionamido)acridine (JM-ACI-37)

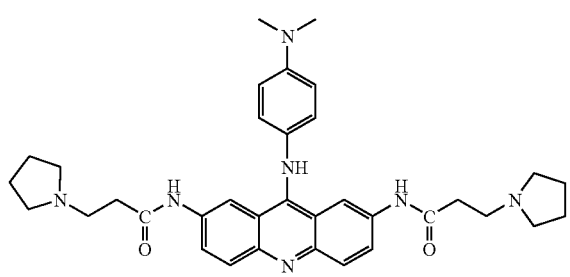

2,7-Bisamido-9-chloroacridine BR-ACO-16 (150 mg, 0.3 mmol) was treated with N,N-dimethyl-1,4-phenylenediamine (90 mg) according to the general procedure to give the desired product JM-ACI-37 (50 mg, 28%) as a dark brown solid.

Mp>320° C., $^1$H-NMR (CDCl$_3$) δ 1.77 (8 H, m, N(CH$_2$CH$_2$)$_2$), 2.47 (4 H, t, J 5.7 Hz, COCH$_2$CH$_2$N), 2.54 (8 H, m, N(CH$_2$CH$_2$)$_2$), 2.78 (4 H, t, J 5.75 Hz, COCH$_2$CH$_2$N), 2.82 (6 H, s, N(CH$_2$)$_2$), 6.57 (2 H, d, J 9.0 Hz, H-3',5'), 6.77 (2 H, d, J 9.0 Hz H-2',6'), 7.70 (2 H, dd, J 9.2 Hz, J 2.2 Hz, H-3,6), 8.01 (2 H, d, J 9.2 Hz, H-4,5), 8.12 (2 H, d, J 2.2 Hz, H-1,8), 11.41 (2 H, s, NHCO), m/z (EI) 594.3572 (C$_{35}$H$_{44}$N$_7$O$_2$ M+H requires 594.3556).

Example 112

Trihydrochloride Salt (JM-ACI-38)

The trihydrochloride addition salt, JM-ACI-37, of the compound in the previous example, was also prepared by treatment with HCl.

Example 113

N-(9-Phenylamino)-2,7-bis(3-pyrrolidinopropionamido)acridine (JM-ACI-39)

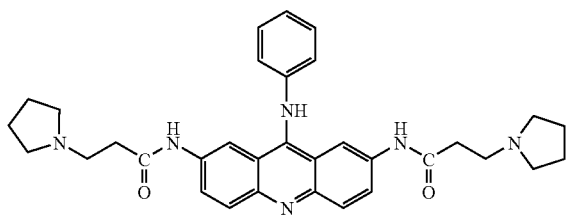

2,7-Bisamido-9-chloroacridine BR-ACO-16 (150 mg, 0.3 mmol) was treated with aniline (0.5 ml) according to the general procedure to give the desired product JM-ACI-39 (120 mg, 72%) as a bright red solid.

Mp>320° C., $^1$H-NMR (CDCl$_3$) δ 1.74 (8 H, m, N(CH$_2$CH$_2$)$_2$), 2.46 (4 H, t, J 5.7 Hz, COCH$_2$CH$_2$N), 2.55 (8 H, m, N(CH$_2$CH$_2$)$_2$), 2.76 (4 H, t, J 5.7 Hz, COCH$_2$CH$_2$N), 6.4 (1 H, m, H-1'), 6.7 (1 H, d, J 7.5 Hz, H-4'), 6.83 (2 H, m, H-3',5'), 7.10 (2 H, m, H-2',6'), 7.69 (2 H, dd, J 9.3 Hz, J 2.3 Hz, H-3,6), 8.04 (2 H, d, J 9.3 Hz, H-4,5), 8.14 (2 H, d, J 2.3 Hz, H-1,8), 11.56 (2 H, s, NHCO), m/z (EI) 551.3153 (requires C$_{33}$H$_{39}$N$_6$O$_2$ M+H 551.3134).

Example 114

Trihydrochloride Salt (JM-ACI-40)

The trihydrochloride addition salt, JM-ACI-39, of the compound in the previous example, was also prepared by treatment with HCl.

Example 115

N-[9-(3'-Methoxyphenylamino)]-2,7-bis(3-pyrrolidinopropionamido)acridine (JM-ACI-41)

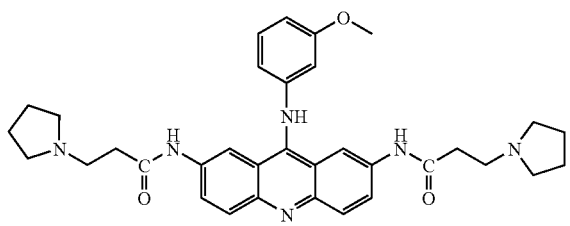

2,7-Bisamido-9-chloroacridine BR-ACO-16 (200 mg, 0.4 mmol) was treated with m-anisidine (0.5 mL) according to the general procedure to give the desired product JM-ACI-41 (100 mg, 43%) as an orange solid.

Mp>320° C., $^1$H-NMR (CDCl$_3$) δ 1.79 (8 H, m, N(CH$_2$CH$_2$)$_2$), 2.53 (4 H, t, J 5.3 Hz, COCH$_2$CH$_2$N), 2.62 (8 H, m, N(CH$_2$CH$_2$)$_2$), 2.83 (4 H, t, J 5.3 Hz, COCH$_2$CH$_2$N), 3.64 (3 H, s, OCH$_3$), 6.36 (3 H, m, H-2',4',6'), 7.3 (1 H, m, H-5'), 7.80 (2 H, m, J 9.3 Hz, H-3,6), 8.04 (2 H, d, J 9.3 Hz, H-4,5), 8.16 (2 H, m, H-1,8), 11.60 (2 H, s, NHCO), m/z (EI) 581.3247 (C$_{34}$H$_{41}$N$_6$O$_3$ M+H requires 581.3240).

Example 116

Trihydrochloride Salt (JM-ACI-42)

The trihydrochloride addition salt, JM-ACI-41, of the compound in the previous example, was also prepared by treatment with HCl.

Example 117

N-[9-(2'-Hydroxyphenylamino)]-2,7-bis(3-pyrrolidinopropionamido)acridine (JM-ACI-45)

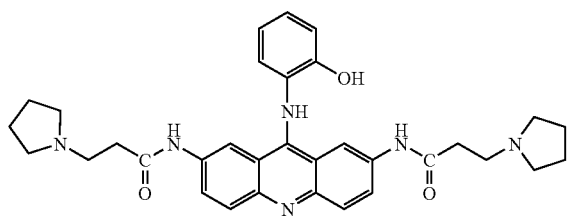

2,7-Bisamido-9-chloroacridine BR-ACO-16 (150 mg, 0.3 mmol) was treated with 1,2-aminophenol (50 mg) according to the general procedure to give the desired product JM-ACI-45 (100 mg, 59%) as a dark red solid.

Mp>320° C., $^1$H-NMR (CDCl$_3$) δ 1.80 (8 H, m, N(CH$_2$CH$_2$)$_2$), 2.57 (4 H, t, J 6 Hz, COCH$_2$CH$_2$N), 2.63 (8 H, m, N(CH$_2$CH$_2$)$_2$), 2.86 (4 H, t, J 6.0 Hz, COCH$_2$CH$_2$N), 6.45 (1 H, m, H-2'), 6.59 (1 H, m, H-3'), 6.75 (1 H, m, H-4'), 6.94 (1 H, m, H-5'), 7.73 (2 H, m, J 9.3 Hz, J 2.25 Hz, H-3,6), 8.00 (2 H, d, J 9.3 Hz, H-4,5), 8.16 (2 H, d, J 2.25 Hz, H-1,8), 11.30 (2 H, s, NHCO), m/z (EI) 567.3067 (C$_{33}$H$_{40}$N$_7$O$_2$ M+H requires 567.3084).

Example 118

Trihydrochloride Salt (JM-ACI-46)

The trihydrochloride addition salt, JM-ACI-45, of the compound in the previous example, was also prepared by treatment with HCl.

GROUP F: 2,6,9-ACRIDINES

Example 119

9-chloro-2,6-bis(3-pyrrolidinopropionamido)acridine (JH-ACI-98)

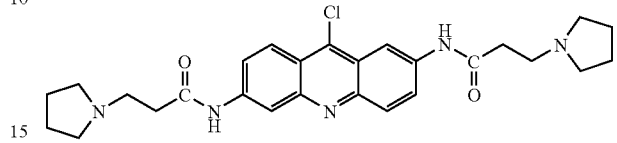

A suspension of 2,6-bis(3-pyrrolidinopropionamido)acridone AR-ACO-10 (2.0 g, 4.2 mmol) in CHCl$_3$ (40 mL) was treated with phosphorus pentachloride (0.9 g, 4.2 mmol), followed by cautious addition of phosphorus oxychloride (50 mL). This suspension was stirred at room temp. for 30 min and brought to a gentle reflux over 1 hr. Gentle reflux was maintained for 26 hr. The reaction mixture was cooled to rt then slowly dropped onto ice (~600 mL) over 10 min. The aqueous mixture was made basic to pH 7/8 with ammonia whilst maintaining a temp. <25° C. The aqueous layer was extracted with CHCl$_3$ (5×200 mL). The organic extracts were combined, washed with brine (200 mL), dried (Na$_2$SO$_4$) and concentrated. The resulting solid was tritrated with diethyl ether (30 mL) to give the desired product (1.3 g, 62%) as a light brown solid.

$^1$H-NMR (CDCl$_3$) δ 1.97-1.98 (8 H, m, N(CH$_2$CH$_2$)$_2$), 2.61-2.66 (4 H, m, COCH$_2$CH$_2$N), 2.75-2.76 (8 H, m, N(CH$_2$CH$_2$)$_2$), 2.90-2.96 (4 H, m, COCH$_2$CH$_2$N), 7.66-7.70 (1 H, d, J 9.3 Hz and 2.2 Hz, H-3/7), 7.92-7.96 (1 H, d, J 9.3 and 2.2 Hz, H-3/7), 8.08-8.11 (1 H, d, J 9.3 Hz, H-4/8), 8.17-8.18 (1 H, m, H-1/5), 8.31-8.35 (1 H, d, J 9.3 Hz, H-4/8), 8.75-8.76 (1 H, m, H-1/5), 11.72 (2 H, s, NHCO).

Example 120

9-Substitution, 2,6,9-Derivatives, General Procedure

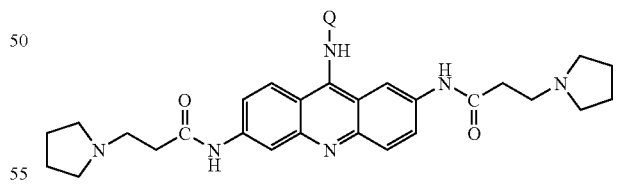

To a vigorously stirred solution of JH-ACI-98 in CHCl$_3$ was added dropwise a solution of the proposed amine, Q-NH$_2$ (e.g., NH$_2$(CH$_2$)$_p$NH$_2$, substituted anilines), for example, in CHCl$_3$. This solution was stirred for a further 2-5 hr, the solvent was removed under reduced pressure, the resultant compound was purified by flash column chromatography. The eluent used for 9-aryl substituents was 100% CHCl$_3$ (NEt$_3$) to 30% MeOH/CHCl3 (NEt$_3$). The eluent used for 9-alkyl substituents was 100% CHCl$_3$ (NEt$_3$) to 5% NEt$_3$ in MeOH.

Example 121

N-{9-[4'-(Amino)phenylamino]}-2,6-bis(3-pyrrolidinopropionamido)acridine (JH-ACI-104)

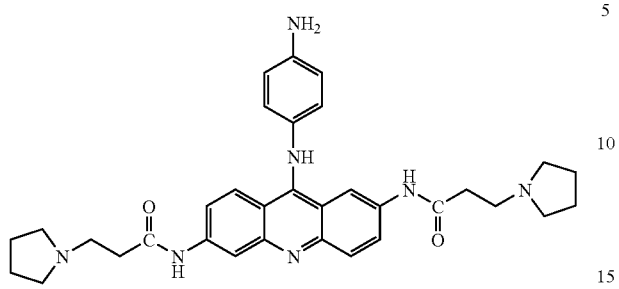

2,6-Bisamido-9-chloroacridine JH-ACI-98 (500 mg, 1.0 mmol) was treated with 1,4-phenylenediamine (0.5 mL) according to the general procedure to give the desired product JH-ACI-104 (400 mg, 88%) as a brown solid.

Mp>320° C., $^1$H-NMR (CDCl$_3$) δ 1.83 (8 H, m, N(CH$_2$CH$_2$)$_2$), 2.55 (4 H, m, COCH$_2$CH$_2$N), 2.58 (8 H, m, N(CH$_2$CH$_2$)$_2$), 2.84 (4 H, m, COCH$_2$CH$_2$N, (6.61 (2 H, d, J 8.7 Hz, ArH-3',5'), 6.66 (2 H, d, J 8.7 Hz, ArH-2',6'), 7.5-8.0 (6 H, m, H-1,3,4,5,7,8) 10. (1 H, s, NHCO), 10.89 (1 H, s, NHCO), m/z (EI) 566.3219 (C$_{33}$H$_{44}$N$_7$O$_2$ M+H requires 566.3243).

Example 122

Trihydrochloride Salt (JH-ACI-105)

The trihydrochloride addition salt, JH-ACI-105, of the compound in the previous example, was also prepared by treatment with HCl.

Example 123

N-{9-[4'-(N,N-Dimethyl)phenylamino]}-2,6-bis(3-pyrrolidinopropionamido)acridine (BSU-SB-36/188)

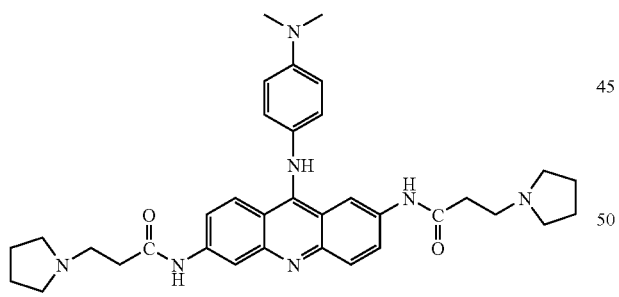

2,6-Bisamido-9-chloroacridine JH-ACI-98 (500 mg, 1.0 mmol) was treated with 4-N,N-dimethylaminoaniline (0.4 g) according to the general procedure to give the desired product BSU-SB-36/188 (210 mg, 36%) as a dark brown solid.

$^1$H-NMR (DMSO) δ 1.87-1.92 (8 H, m, N(CH$_2$CH$_2$)$_2$), 2.38-2.59 (4 H, m, COCH$_2$CH$_2$N), 2.61-2.80 (8 H, m, N(CH$_2$CH$_2$)$_2$), 2.87-2.92 (10 H, m, COCH$_2$CH$_2$N and N(CH$_3$)$_2$), 6.64-6.67 (2 H, d, J 9.0 Hz, H-2',6' or H-3',5'), 6.91-6.94 (2H, d, J 9.0 Hz, H-2',6' or H-3',5'), 7.49-7.52 (1 H, m, J 9.0 Hz, acridine), 7.60-7.64 (1 H, m, acridine), 7.73-7.76 (1 H, m, acridine) 7.91-7.92 (2 H, m, acridine), 8.40 (1 H, s, acridine) 11.33 (1 H, s, NHCO), 11.53 (1 H, s, NHCO).

Example 124

Tetrahydrochloride Salt (SB-ACI-18)

The tetrahydrochloride addition salt, SB-ACI-18, of the compound in the previous example, was also prepared by treatment with HCl.

Example 125

N-{9-[2-(N,N-Dimethyl)ethylamino]}-2,6-bis(3-pyrrolidinopropionamido)acridine (BSU-SB-36/190)

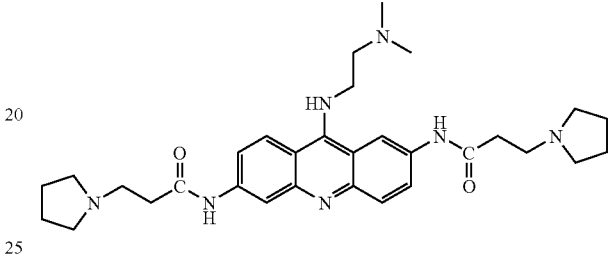

2,6-Bisamido-9-chloroacridine JH-ACI-98 (500 mg, 1.0 mmol) was treated with N,N-dimethylethylamine (0.33 mL) according to the general procedure to give the desired product BSU-SB-36/190 (410 mg, 75%) as a brown hygroscopic solid.

$^1$H-NMR (CDCl$_3$) δ 1.95 (8 H, m, N(CH$_2$CH$_2$)$_2$), 2.39 (6 H, s, CH$_3$), 2.61-2.67 (6 H, m, COCH$_2$CH$_2$N and HNCH$_2$CH$_2$N), 2.72 (8 H, s, N(CH$_2$CH$_2$)$_2$), 2.88-2.94 (4 H, m, COCH$_2$CH$_2$N), 3.91-3.96 (2 H, m, HNCH$_2$CH$_2$N), 7.32-7.33 (1 H, m, H-3/7), 7.78-7.79 (1H, m, H-3/7), 7.93-8.00 (2 H, m, H-8,1), 8.06-8.10 (1 H, m, J 9.4 Hz, H-4), 8.96-8.97 (1 H, m, H-5), 11.54-11.62 (2 H, s, NHCO).

Example 126

Tetrahydrochloride Salt (SB-ACI-19)

The tetrahydrochloride addition salt, SB-ACI-19, of the compound in the previous example, was also prepared by treatment with HCl.

Example 127

N-[9-(3'-Aminophenylamino)]-2,6-bis(3-pyrrolidinopropionamido)acridine (BSU-SB-36/194)

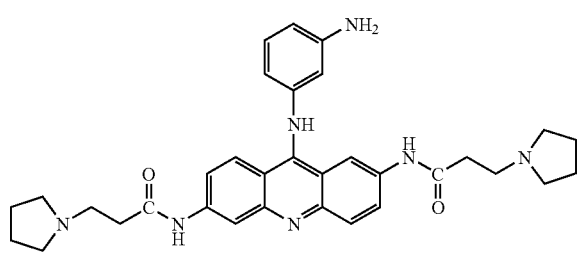

2,6-Bisamido-9-chloroacridine JH-ACI-98 (500 mg, 1.0 mmol) was treated with 1,3-phenylinediamine (0.32 g)

according to the general procedure to give the desired product BSU-SB-36/194 (110 mg, 19%) as an orange solid.

$^1$H-NMR (CDCl$_3$) δ 1.89-1.93 (8 H, m, N(CH$_2$CH$_2$)$_2$), 2.57-2.64 (4 H, m, COCH$_2$CH$_2$N), 2.73-2.79 (8 H, m, N(CH$_2$CH$_2$)$_2$), 2.90-2.94 (4 H, m, COCH$_2$CH$_2$N), 6.13 (1 H, s, H-2'), 6.25-6.29 (2 H, m, H-4',6'), 6.96-7.02 (1 H, t, J 7.9 Hz, H-5'), 7.52-7.62 (1 H, m, H-3,5 or 4,8), 7.65-7.66 (1 H, m, H-3,5 or 4,8), 7.87-791 (1 H, m, H-3,5 or 4,8), 7.96-8.00 (1 H, m, H-3,5 or 4,8), 8.11-8.12 (1 H, m, H-1/5), 839-8.40 (1 H, m, H-1/5), 11.37 (1 H, s, NHCO), 11.52 (1 H, s, NHCO).

Example 128

Trihydrochloride Salt (SB-ACI-17)

The trihydrochloride addition salt, SB-ACI-17, of the compound in the previous example, was also prepared by treatment with HCl.

Example 129

N-[9-(2'-Aminophenylamino)]2,6-bis(3-pyrrolidino-propionamido)acridine (BSU-SB-36/202)

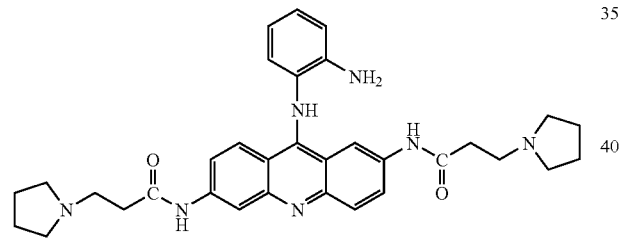

2,6-Bisamido-9-chloroacridine AR-ACO-10 (500 mg, 1.0 mmol) was treated with 1,3-phenylinediamine (0.32 g) according to the general procedure to give the desired product BSU-SB-36/202 (400 mg, 70%) as an orange solid.

$^1$H-NMR (CDCl$_3$) δ 1.86-1.88 (8 H, m, N(CH$_2$CH$_2$)$_2$), 2.53-2.57 (4 H, m, COCH$_2$CH$_2$N), 2.60-2.69 (8 H, m, N(CH$_2$CH$_2$)$_2$), 2.82-2.87 (4 H, t, J 5.8 Hz, COCH$_2$CH$_2$N), 6.55 (2 H, m, H-3'/4'/5'/6'), 6.83-6.95 (2 H, m, H-3'/4'/5'/6'), 7.11 (1 H, m), 7.59-7.71 (3 H, m), 7.95 (1 H, m), 8.25 (1 H, s), 11.13 (1 H, s, NHCO), 11.48 (1 H, s, NHCO).

Example 130

Trihydrochloride Salt (SB-ACI-16)

The trihydrochloride addition salt, SB-ACI-16, of the compound in the previous example, was also prepared by treatment with HCl.

Example 131

N-[9-(Phenylamino)]-2,6-bis(3-pyrrolidinopropiona-mido)acridine (BSU-SB-36/196)

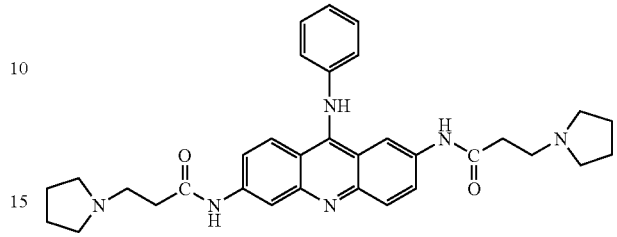

2,6-Bisamido-9-chloroacridine AR-ACO-10 (500 mg, 1.0 mmol) was treated with phenylamine (0.3 mL) according to the general procedure to give the desired product BSU-SB-36/196 (240 mg, 44%) as an orange solid;

$^1$H-NMR (CDCl$_3$) δ 1.86-1.92 (8 H, m, N(CH$_2$CH$_2$)$_2$), 2.55-2.62 (4 H, m, COCH$_2$CH$_2$N), 2.68-2.72 (8 H, m, N(CH$_2$CH$_2$)$_2$), 2.985-2.92 (4 H, m, COCH$_2$CH$_2$N), 6.82-6.85 (2 H, d, J 8.6 Hz, H-2, 6), 6.90-6.96 (1 H, t, H-3), 7.18-7.24 (2 H, dd, H-3, 5), 7.55-7.66 (2 H, m, J 9.3 and 2.2 Hz, H-3,6), 7.84-7.88 (1 H, d, J 9.3 Hz, H-4/7), 7.95-7.99 (1 H, d, J 9.3 Hz, H-4/7), 8.08 (1 H, m, H-1/5), 8.37 (1 H, m, H-1/5), 11.46 (1 H, s, NHCO), 11.59 (1 H, s, NHCO).

Example 132

Trihydrochloride Salt (SB-ACI-22)

The trihydrochloride addition salt, SB-ACI-22, of the compound in the previous example, was also prepared by treatment with HCl.

Example 133

N-{9-[3-(N,N-Dimethyl)propylamino]}-2,6-bis(3-pyrrolidinopropionamido)acridine (BSU-SB-36/198)

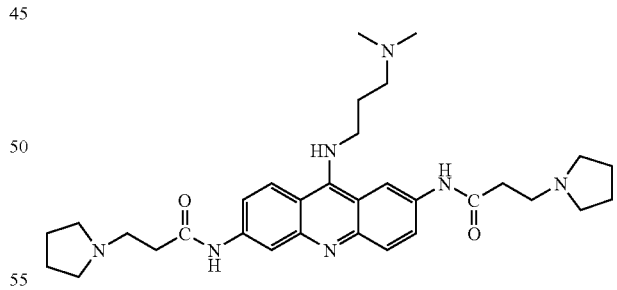

2,6-Bisamido-9-chloroacridine AR-ACO-10 (500 mg, 1.0 mmol) was treated with N, N-dimethylpropylamino (0.4 mL) according to the general procedure to give the desired product BSU-SB-36/198 (210 mg, 38%) as a yellow solid.

$^1$H-NMR (CDCl$_3$) δ 1.92-1.95 (10 H, m, N(CH$_2$CH$_2$)$_2$ and HNCH$_2$CH$_2$CH$_2$N), 2.39 (6 H, s, N(CH$_3$)$_2$), 2.58-2.66 (6 H, m, COCH$_2$CH$_2$N and HNCH$_2$CH$_2$CH$_2$N), 2.71 (8 H, s, N(CH$_2$CH$_2$)$_2$), 2.87-2.93 (4 H, m, COCH$_2$CH$_2$N), 4.12-4.17 (2 H, m, HNCH$_2$CH$_2$CH$_2$N), 7.70 (1 H, m), 7.88-8.07 (4 H, m), 8.96 (1 H, m), 11.48 (1 H, s, NHCO), 11.65 (1 H, s, NHCO).

Example 134

Tetrahydrochloride Salt (SB-ACI-20)

The tetrahydrochloride addition salt, SB-ACI-20, of the compound in the previous example, was also prepared by treatment with HCl.

Example 135

N-[9-(Cyclohexylamino)]-2,6-bis(3-pyrrolidinopropionamido)acridine (BSU-SB-36/200)

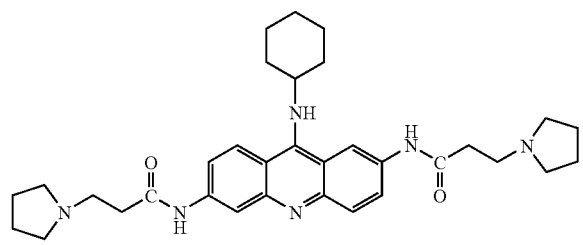

2,6-Bisamido-9-chloroacridine AR-ACO-10 (500 mg, 1.0 mmol) was treated with cyclohexylamine (0.35 mL) according to the general procedure to give the desired product BSU-SB-36/200 (230 mg, 41%) as a yellow solid.

$^1$H-NMR (CDCl$_3$) δ 1.06-1.66 (4 H, m, HNCH (CH$_2$CH$_2$)$_2$ CH$_2$), 1.77 (2 H, m, HNCH(CH$_2$CH$_2$)$_2$CH$_2$), 1.95 (8 H, m, N(CH$_2$CH$_2$)$_2$), 2.59-2.66 (4 H, m, COCH$_2$CH$_2$N), 2.73-2.75 (8 H, m, N(CH$_2$CH$_2$)$_2$), 2.89-2.96 (4 H, m, COCH$_2$CH$_2$N), 3.89 (1 H, m, HNCH(CH$_2$CH$_2$)$_2$ CH$_2$), 7.30-7.34 (1 H, m), 7.84-8.05 (4 H, m), 8.83-8.84 (1 H, m), 11.58 (1 H, s, NHCO), 11.60 (1 H, s, NHCO).

Example 136

Trihydrochloride Salt (SB-ACI-21)

The trihydrochloride addition salt, SB-ACI-21, of the compound in the previous example was also prepared by treatment with HCl.

Biological Data

Taq Polymerase Assay

All compounds were tested using a Taq assay to eliminate broad-spectrum polymerase inhibitors and thus filter out any false positives which might have occurred in the TRAP assay. Thus, preferred compounds are "Taq-negative." Compounds were tested as their acid addition salts at various final concentrations (0.1, 0.5, 1, 5, 10, 20 and 50 .μM) in a PCR 50 .μL master mix containing 10 ng pCl-neo mammalian expression vector (Promega, Southampton, UK) and forward (GGAGTTCCGCGTTACATAAC) (SEQ ID NO:1)) and reverse (GTCTGCTCGAAGCATTTAACC) (SEQ ID NO:2)) primers (200 nmol) as described in the art (see, e.g., Perry et al., 1998a). The product of approximately 1 kb was visualized on a 2% w/w agarose gel following amplification (30 cycles of 94° C. for 1 min, 55° C. for 1 min and 72° C. for 2.5 min). The Taq assay was carried out until no Taq polymerase inhibition was observed. All compounds were found to be Taq negative.

Modified Telomeric Repeat Amplification Protocol (TRAP) Assay

The ability of compounds to inhibit telomerase in a cell-free assay was assessed with a modified TRAP assay using extracts from exponentially growing A2780 human ovarian carcinoma cells. The TRAP assay was performed in 2 steps: (a) telomerase-mediated extension of the forward primer (TS: 5'-AATCCGTCGAGCAGAGTT (SEQ ID NO:3), Oswel Ltd., Southampton, UK) contained in a 40 . mu.L reaction mix comprising TRAP buffer (20 mM Tris-HCl (pH 8.3), 68 mM KCl, 1.5 mM MgCl.sub.2, 1 mM EGTA, 0.05% v/v Tween 20), 0.05 μg bovine serum albumin, 50 μM of each deoxynucleotide triphosphate, 0.1 μg TS primer, and 3 μCi of [α-$^{32}$P]dCTP (Amersham plc, UK). Protein (40 ng or 20 ng) was then incubated with the reaction mix+agent (acid addition and quaternary dimethiodide salts) at final concentrations of up to 50 μM for 20 min at 25° C. A lysis buffer (no protein) control, heat-inactivated protein control, and 50% protein (20 ng or 10 ng) control were included in each assay; and (b) while heating at 80° C. in a PCR block of a thermal cycler (Hybaid, UK) for 5 min to inactivate telomerase activity, 0.1 μg of reverse CX primer (3'-AATCCCATTCCCATTCCCATTCCC-5' (SEQ ID NO:4)) and 2 Units of Taq DNA polymerase ("red hot", Advanced Biotechnologies) were added. A 3-step PCR was then performed: 94° C. for 30 s, 50° C. for 30 s, and 72° C. for 1 min for 31 cycles. Telomerase-extended PCR products in the presence or absence of compounds were then determined either by electrophoretic separation using 8% w/w acrylamide denaturing gels and analysis by phosphorimaging or autoradiography, or by harvesting on Whatman filters (25 mm glass microfibre) and analysis by liquid scintillation counting. The data are summarized in Table 1.

Growth Inhibition Assay

Growth inhibition was measured in three human ovarian carcinoma cell lines (A2780, CH1, and SKOV-3) and one human cervix carcinoma cell line (A431) using the sulforhodamine B (SRB) assay. Briefly, between 3000 and 6000 cells were seeded into the wells of 96-well microtiter plates and allowed to attach overnight. Compounds (acid addition and quaternary dimethiodide salts) were dissolved at 500 μM in water and immediately added to wells in quadruplicate at final concentrations of 0.05, 0.25, 1, 5 and 25 μM. Following an incubation period of 96 hr, remaining cells were fixed with ice-cold 10% w/v trichloroacetic acid (30 min) and stained with 0.4% SRB in 1% v/v acetic acid (15 min). Mean absorbance at 540 nm for each drug concentration was expressed as a percentage of the control untreated well absorbance, and IC$_{50}$ values (concentration required to inhibit cell growth by 50%) were determined for each agent. The data are summarized in Table 1.

TABLE 1

Telomerase Inhibitory Activity and Cytotoxicity for Salts

| Class | Compound Ref. No. | $^{tel}$IC$_{50}$ (μM) | Cytotoxicity - IC$_{50}$ (μM) | | | |
|---|---|---|---|---|---|---|
| | | | A2780 | CH1 | SKOV-3 | A431 |
| 2,6,9-ine | JH-ACI-105 | 0.08 | >25 | 15.8 | >25 | >25 |
| 2,7-one | BR-ACO-10 | 5.8 | >25 | >25 | >25 | |
| 2,7-one | BR-ACO-9 | 2.8 | >25 | >25 | >25 | |
| 2,7-one | JH-ACO-22 | 1.92 | >25 | >25 | >25 | >25 |
| 2,7-one | JH-ACO-28 | 0.66 | >25 | >25 | >25 | >25 |
| 2,7-one | JM-ACO-07 | 1.97 | >25 | >25 | >25 | >25 |
| 2,7-one | JM-ACO-09 | 1.58 | >25 | >25 | >25 | >25 |
| 2,7-one | JM-ACO-12 | 2.33 | >25 | >25 | >25 | >25 |

TABLE 1-continued

Telomerase Inhibitory Activity and Cytotoxicity for Salts

| Class | Compound Ref. No. | $^{tel}IC_{50}$ (μM) | Cytotoxicity - $IC_{50}$ (μM) | | | |
|---|---|---|---|---|---|---|
| | | | A2780 | CH1 | SKOV-3 | A431 |
| 3,6,9-ine | BR-ACO-19 | 0.095 | 10 | 10.1 | 13 | 15.8 |
| 3,6,9-ine | BR-ACO-20 | 0.06 | >25 | >25 | >25 | |
| 3,6,9-ine | JC-ACI-3 | 0.07 | | | | 2.5 |
| 3,6,9-ine | JC-ACI-4 | 0.15 | | | | 2.5 |
| 3,6,9-ine | JC-ACI-5 | 0.1 | 2.8 | 0.6 | 3.2 | 1.3 |
| 3,6,9-ine | JC-ACI-9 | 0.012 | >25 | 20 | >25 | 20 |
| 3,6,9-ine | JH-ACI-101 | 0.16 | 1.6 | 2.3 | 1.2 | 2.5 |
| 3,6,9-ine | JH-ACI-103 | 0.14 | 1.0 | 3.2 | 2.0 | 2.5 |
| 3,6,9-ine | JH-ACI-65 | 0.06 | >25 | 17.0 | 15.8 | >25 |
| 3,6,9-ine | JH-ACI-69 | 0.05 | 12.6 | >25 | >25 | 11.2 |
| 3,6,9-ine | JH-ACI-74 | 0.06 | 12.6 | 15.8 | >25 | 12.6 |
| 3,6,9-ine | JH-ACI-76 | 0.02 | 11.0 | 10.0 | 15.8 | 7.1 |
| 3,6,9-ine | JH-ACI-78 | 0.1 | 7.9 | 2 | 4 | 2 |
| 3,6,9-ine | JH-ACI-82 | 0.09 | 12.5 | 2.8 | 1.1 | 2.5 |
| 3,6,9-ine | JH-ACI-86 | 0.14 | 10 | 3.2 | 17.8 | 10 |
| 3,6,9-ine | JH-ACI-88 | 0.21 | 3.2 | 2.8 | 9.3 | 3.2 |
| 3,6,9-ine | JH-ACI-90 | 0.04 | 3.2 | 1.8 | 3.4 | 2.2 |
| 3,6,9-ine | JM-ACI-14 | 0.05 | 19 | >25 | >25 | >25 |
| 3,6,9-ine | SB-ACI-11 | 0.018 | >25 | 17.0 | >25 | >25 |
| 3,6,9-ine | SB-ACI-12 | 0.018 | >25 | >25 | >25 | 25 |
| 3,6,9-ine | SB-ACI-13 | 0.066 | >25 | >25 | >25 | >25 |
| 3,6,9-ine | SB-ACI-14 | 0.1 | >25 | >25 | >25 | >25 |
| 3,6-one | BR-ACO-33 | 1.9 | 3 | 3 | 5.6 | |
| 3,6-one | BR-ACO-34 | 1.8 | >25 | >25 | >25 | |
| 3,6-one | BR-ACO-36 | 3.3 | 13 | 11.8 | 12 | |
| 3,6-one | BR-ACO-37 | 1.6 | 11.8 | 11 | 10.5 | |
| 3,6-one | BR-ACO-39 | 0.74 | >25 | >25 | >25 | |
| 3,6-one | BR-ACO-4 | 8 | >25 | >25 | >25 | |
| 3,6-one | BR-ACO-5 | 5.9 | 19 | 13 | 21 | |
| 3,6-one | BR-ACO-6 | 4.3 | >25 | >25 | >25 | |
| 3,6-one | BR-ACO-7 | 5.7 | >25 | >25 | >25 | |
| 3,6-one | BR-ACO-8 | 49 | >25 | >25 | >25 | |
| 3,6-one | JH-ACO-32 | 1.77 | 1.9 | 2.5 | 2.5 | 10 |

REFERENCES

A number of patents and publications are cited above in order to more fully describe and disclose the invention and the state of the art to which the invention pertains. Full citations for these references are provided below. Each of these references is incorporated herein by reference in its entirety into the present disclosure.

Autexier, 1999, "Telomerase as a Possible Target for Anticancer Therapy," *Chemistry & Biology*, November 1999, Vol. 6, pp. R299-R303.

Bogert et al., 1930, *Collect. Czech. Chem. Comm.*, Vol. 2, pp. 383-395.

Bostock-Smith et al., 1988, "Antitumour Polycyclic Acridines, Part 6," *Biochemistry*, Vol. 38, No. 21, pp. 6723-6731.

Gimenez-Arnau et al., 1998, "Antitumour Polycyclic Acridines, Part 2," *Anti-Cancer Drug Design*, Vol. 13, pp. 125-143.

Gimenez-Arnau et al., 1998, "Antitumour Polycyclic Acridines, Part 4," *Anti-Cancer Drug Design*, Vol. 13, pp. 431-451.

Goldberg and Kelly, 1946, *J. Chem. Soc.*, p. 102.

Goldstein and de Simo, 1927, *Helv. Chim. Acta.*, Vol. 10, p. 604.

Hagan et al., 1997, "Antitumour Polycyclic Acridines, Part 1," *J. Chem. Soc., Perkin Trans. I*, p. 2739.

Hagan et al., 1998, "Antitumour Polycyclic Acridines, Part 3," *J. Chem. Soc., Perkin Trans. I*, p. 915.

Harrison et al., 1999, "Human Telomerase Inhibition by Substituted Acridine Derivatives," *Bioorganic & Medicinal Chemistry Letters*, Vol. 9, pp. 2463-2468.

Julino et al., 1998, "Antitumour Polycyclic Acridines, Part 5," *J. Chem. Soc., Perkin Trans. I*, p. 1677.

Korolev et al., 1976, *J. Gen. Chem. USSR (Engl. Trans.)*, Vol. 46, pp. 2250-2252.

Korolev et al., 1977, *J. Gen. Chem. USSR (Engl. Trans.)*, Vol. 47, pp. 2118-2122.

Matsumura, 1929, *Journal*, Vol. V, No. N, pp. P-P.

Neidle et al., 1999, "Telomerase as an Anti-Cancer Target: Current Status and Future Prospects," *Anti-Cancer Drug Design*, Vol. 14, pp. 341-347.

Perry et al., 1998a, "1,4- and 2,6-Disubstituted Amidoanthracene-9,10-dione Derivatives as Inhibitors of Human Telomerase," *J. Med. Chem.*, Vol. 41, pp. 3253-3260.

Perry et al., 1998b, "Human Telomerase Inhibition by Regioisomeric Disubstitued Amidoanthracene-9,10-diones," *J. Med. Chem.*, Vol. 41, No. 24, pp. 4873-4884.

Perry et al., 1998c, "Telomeres and Telomerase: Targets for Cancer Chemotherapy?," *Exp. Opin. Ther. Patents*, Vol. 8, No. 12, pp. 1567-1586.

Perry et al., 1999a, "Design, Synthesis and Evaluation of Human Telomerase Inhibitors Based Upon a Tetracyclic Structural Motif," *Anti-Cancer Drug Design*, Vol. 14, pp. 373-382.

Perry et al., 1999b, "2,7-Disubstituted Amidofluorenone Derivatives as Inhibitors of Human Telomerase," *J. Med. Chem.*, Vol. 42, No. 14, pp. 2679-2684.

Read et al., 24 Apr. 2001, "Structure-based design of selective and potent G quadruplex-mediated telomerase inhibitors," *PNAS*, Vol. 98, No. 9, pp. 4844-4849.

Sharma et al., 1997, "Preclinical and Clinical Strategies for Development of Telomerase and Telomere Inhibitors," *Annals of Oncology*, Vol. 8, pp. 1063-1074.

Sun et al., 1997, "Inhibition of Human Telomerase by a G-Quadruplex-Interactive Compound," *J. Med. Chem.*, Vol. 40, pp. 2113-2116.

Urquidi et al., 1998, "Telomerase in Cancer: Clinical Applications," *Ann. Med.*, Vol. 30, pp. 419-430.

The invention claimed is:

1. A compound of the formula:

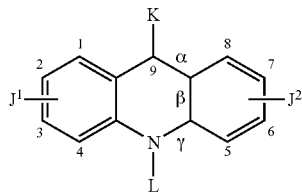

wherein either:
(a) K is =O, L is —H, α is a single bond, β is a double bond, γ is a single bond; or,
(b) K is a 9-substituent, L is absent, α is a double bond, β is a single bond, γ is a double bond;
and wherein:
$J^1$ is a 2- or 3-substituent;
$J^2$ is a 6- or 7-substituent;
$J^1$ and $J^2$ are each independently a group of the formula:

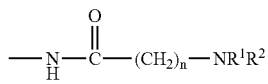

wherein:
n is an integer from 1 to 5; and,
$R^1$ and $R^2$, taken together with the nitrogen atom to which they are attached, form an optionally substituted piperidinyl ring, a morpholin-4-yl ring or an optionally substituted piperazin-1-yl ring;
and wherein, when K is a 9-substituent, K is a group of the formula:

wherein:
$R^N$ is an amino substituent, and is hydrogen, $C_{1-7}$alkyl, $C_{3-20}$heterocyclyl, or $C_{5-20}$aryl; and,
Q is $C_{1-7}$alkyl, $C_{3-20}$heterocyclyl, or $C_{5-20}$aryl, and is optionally substituted;
and pharmaceutically acceptable salts, esters, amides, solvates, hydrates, and protected forms thereof.

2. An acridone compound according to claim 1, wherein K is =O, L is —H, α is a single bond, β is a double bond, γ is a single bond, and having the formula:

(4)

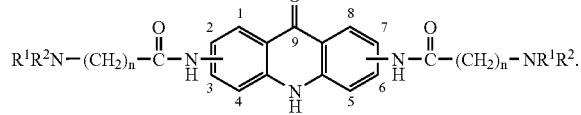

3. An acridine compound according to claim 1, wherein K is a 9-substituent, L is absent, α is a double bond, β is a single bond, γ is a double bond, and having the formula:

(9)

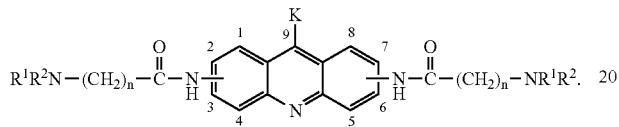

4. A compound according to claim 1, wherein $J^1$ is a 2-substituent and $J^2$ is a 7-substituent.

5. A compound according to claim 1, wherein $J^1$ is a 3-substituent and $J^2$ is a 6-substituent.

6. A compound according to claim 1, wherein $J^1$ is a 2-substituent and $J^2$ is a 6-substituent.

7. A compound according to claim 1, wherein $J^1$ and $J^2$ are the same.

8. A compound according to claim 1, wherein $J^1$ and $J^2$ are each independently a group of the formula:

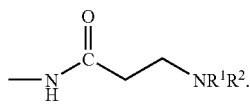

9. A compound according to claim 1, wherein neither $R^1$ nor $R^2$ is —H.

10. A compound according to claim 1, wherein the piperidinyl ring is optionally substituted.

11. A compound according to claim 10, wherein said piperidinyl ring is optionally substituted with at least one group selected from $C_{1-7}$alkyl, $C_{3-20}$aryl-$C_{1-7}$alkyl, $C_{3-20}$aryl, $C_{1-7}$alkyl-$C_{3-20}$aryl, hydroxy, $C_{1-7}$hydroxyalkyl and $C_{1-7}$aminoalkyl.

12. An acridine compound according to claim 3, wherein $R^N$ is hydrogen or aliphatic saturated $C_{1-7}$alkyl.

13. An acridine compound according to claim 3, wherein Q is a $C_{5-20}$aryl group, and is optionally substituted.

14. An acridine compound according to claim 3, wherein K is one of the following:

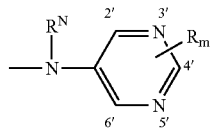 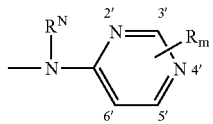

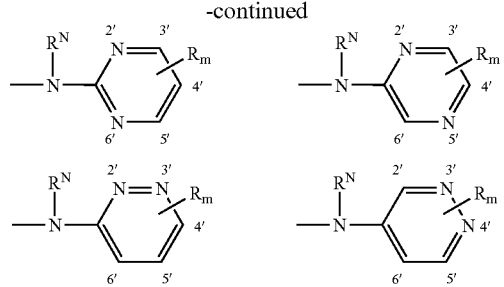

wherein m is an integer from 0 to 3, and each R is independently a substituent.

15. An acridine compound according to claim 3, wherein K is a group of the formula:

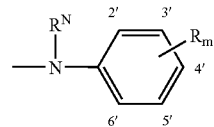

wherein m is an integer from 0 to 5, and each R is independently a substituent.

16. An acridine compound according to claim 15, wherein each R is independently selected from: halo, amino, hydroxy, ether, thio, thioether, $C_{1-7}$alkyl, $C_{1-7}$haloalkyl, acyl, amido, acylamido, carboxy, cyano, and aminoalkyl.

17. An acridine compound according to claim 15, wherein each R is independently a substituent selected from: —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

18. An acridine compound according to claim 3, wherein K is a group of the formula:

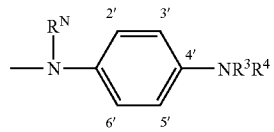

wherein —NR$^3$R$^4$ is as defined for —NR$^1$R$^2$.

19. An acridine compound according to claim 3, wherein K is a group of the formula:

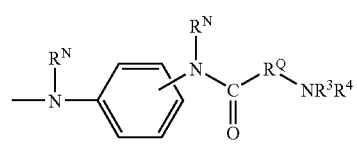

wherein $R^Q$ is a $C_{1-10}$alkylene group, and —NR$^3$R$^4$ is as defined for —NR$^1$R$^2$.

20. An acridine compound according to claim 3, wherein K is a group of the formula:

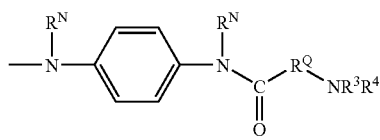

wherein $R^Q$ is a $C_{1-10}$alkylene group, and $-NR^3R^4$ is as defined for $-NR^1R^2$.

21. An acridine compound according to claim 3, wherein K is a group of the formula:

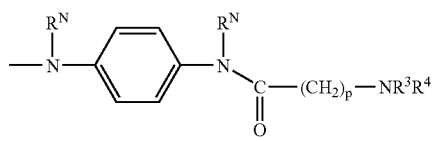

wherein p is an integer from 1 to 10, and $-NR^3R^4$ is as defined for $-NR^1R^2$.

22. An acridine compound according to claim 3, wherein K is a group of the formula:

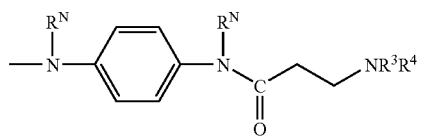

wherein $-NR^3R^4$ is as defined for $-NR^1R^2$.

23. An acridine compound according to claim 3, wherein K is a group of the formula:

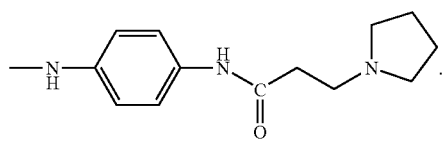

24. An acridine compound according to claim 3, wherein K is a group of the formula:

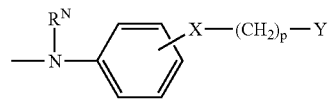

wherein:
X is $-N(N^R)-$, $-CH_2-$, $-O-$, or $-S-$;
Y is $-OH$, $-OR^Y$, or $-NR^3R^4$;
$R^Y$ is $C_{1-7}$alkyl, $C_{3-20}$heterocyclyl, or $C_{5-20}$aryl;
$-NR^3R^4$ is as defined above for $-NR^1R^2$; and,
p is an integer from 1 to 10.

25. An acridine compound according to claim 3, wherein Q is an optionally substituted $C_{1-7}$alkyl group.

26. An acridine compound according to claim 3, wherein Q is an $C_{1-7}$alkyl group substituted with one or more amino groups, one or more hydroxy groups, or one or more carboxy groups.

27. An acridine compound according to claim 3, wherein Q is an $C_{1-7}$alkyl group substituted with one or more amino groups.

28. An acridine compound according to claim 3, wherein K is a group of the formula:

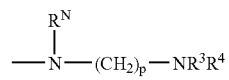

wherein p is an integer from 1 to 10, and $-NR^3R^4$ is as defined for $-NR^1R^2$.

29. An acridine compound according to claim 3, wherein K is a group of the formula:

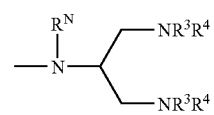

wherein $-NR^3R^4$ is as defined for $-NR^1R^2$.

30. An acridine compound according to claim 3, wherein Q is, or comprises, an alicyclic saturated $C_{1-7}$alkyl group, which is optionally substituted.

31. An acridine compound according to claim 3, wherein K is a group of the formula:

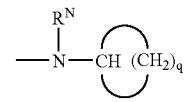

wherein q is an integer from 2 to 7, and wherein the cyclic group is optionally substituted.

32. An acridine compound according to claim 3, wherein K is a group of the formula:

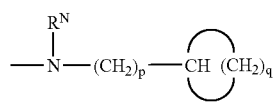

wherein p is an integer from 1 to 10; and q is an integer from 2 to 7, and wherein the cyclic group is optionally substituted.

33. An acridine compound according to claim 3, wherein K is a group of the formula:

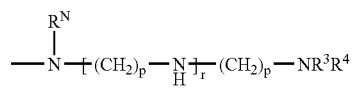

wherein p is an integer from 1 to 10, r is an integer from 1 to 4, and $-NR^3R^4$ is as defined for $-NR^1R^2$.

34. A compound according to claim 1, which is selected from the following compounds, and pharmaceutically acceptable salts, esters, amides, solvates, hydrates, and protected forms thereof:

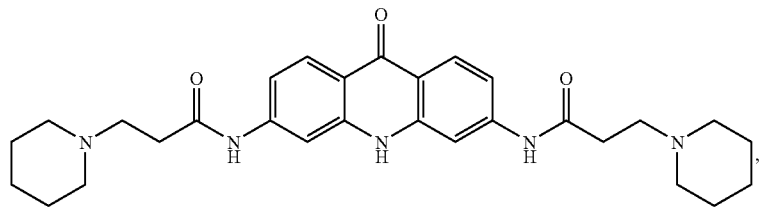,
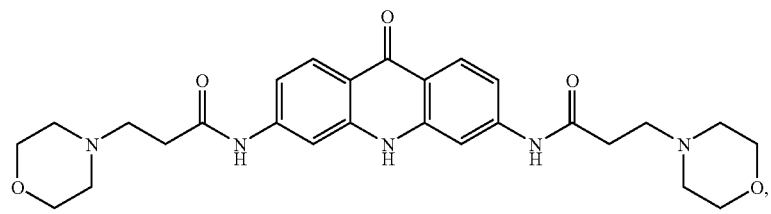,
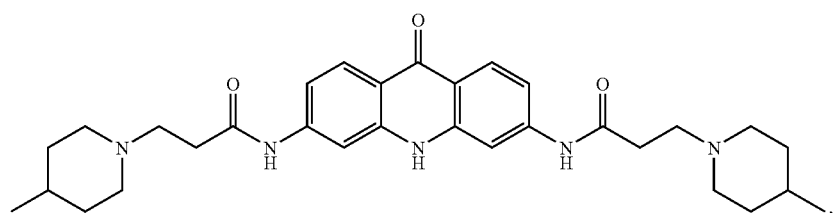,
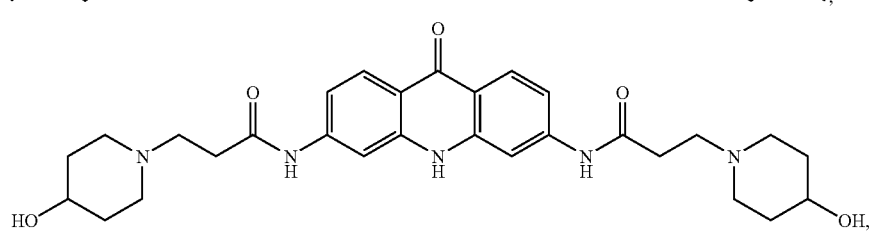,
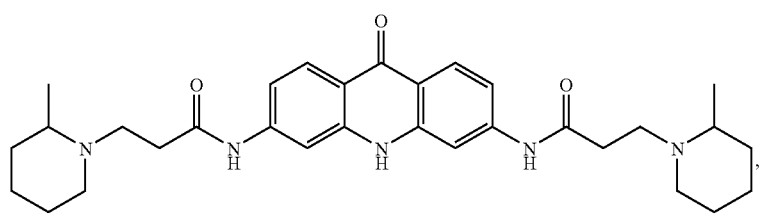,
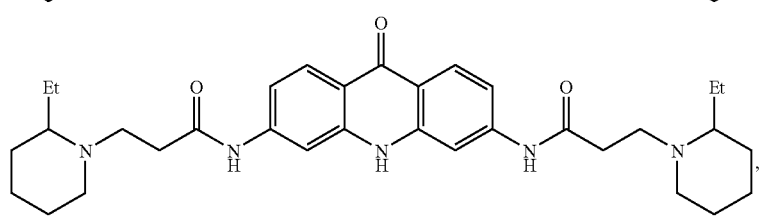,
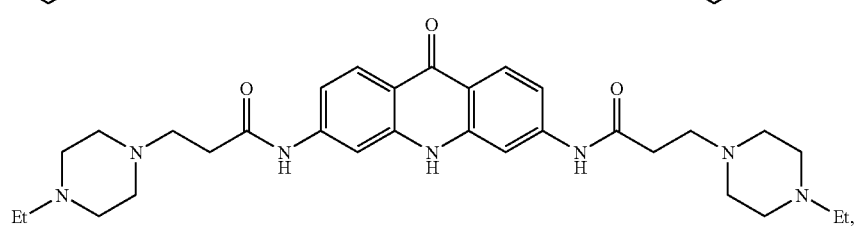,
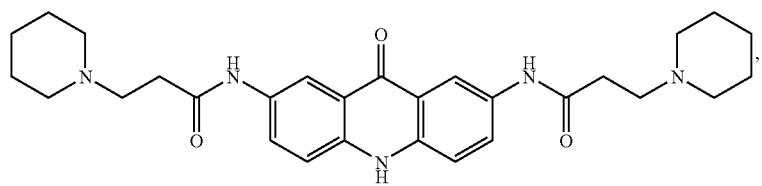, -continued

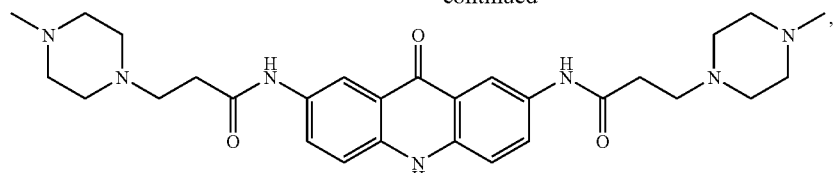

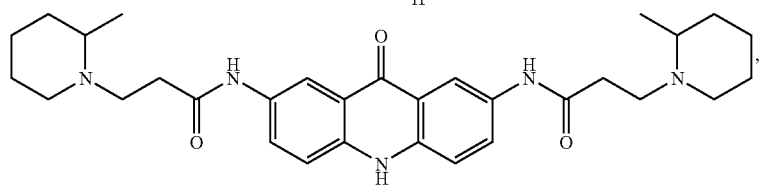

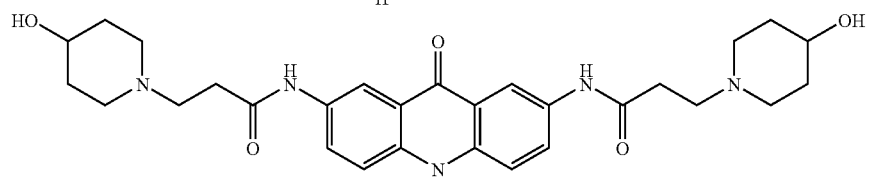

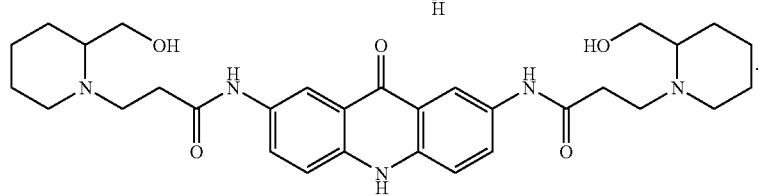

and

35. A composition comprising a compound according to claim 1 and a pharmaceutically acceptable carrier or diluent.

36. A compound of the formula:

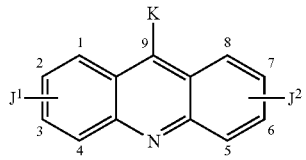

wherein:

$J^1$ is a 2- or 3-substituent;

$J^2$ is a 6- or 7-substituent;

$J^1$ and $J^2$ are each independently a group of the formula:

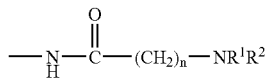

wherein:

n is an integer from 1 to 3; and, $R^1$ and $R^2$, taken together with the nitrogen atom to which they are attached, form an optionally substituted piperidinyl ring, a morpholin-4-yl ring or an optionally substituted piperazin-1-yl ring;

K is a group of the formula:

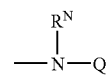

wherein:

$R^N$ is an amino substituent, and is hydrogen or $C_{1-7}$alkyl; and,

Q is $C_{1-7}$alkyl or $C_{5-20}$aryl, and is optionally substituted; and pharmaceutically acceptable salts, solvates, and hydrates thereof.

37. A compound according to claim 36, wherein Q is a $C_{1-7}$alkyl group.

38. A compound according to claim 36, wherein K is a group of the formula:

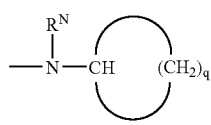

wherein q is an integer from 2 to 7.

39. A compound according to claim 36, wherein K is a group of the formula:

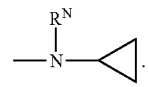

40. A compound according to claim 36, wherein Q is a $C_{1-7}$alkyl group substituted with one or more amino groups.

41. A compound according to claim 36, wherein K is a group of the formula:

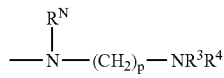

wherein:
p is an integer from 1 to 10; and
$R^3$ and $R^4$ are independently hydrogen, $C_{1-7}$alkyl, $C_{3-20}$heterocyclyl, or $C_{5-20}$aryl, or $R^3$ and $R^4$, taken together with the nitrogen atom to which they are attached, form a heterocyclic ring having from 3 to 8 ring atoms.

42. A compound according to claim 41, wherein p is an integer from 2 to 4.

43. A compound according to claim 36, wherein K is a group of the formula:

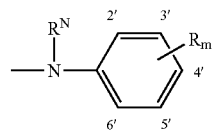

wherein m is an integer from 0 to 5, and each R is independently a substituent.

44. A compound according to claim 43, wherein each R is independently selected from: halo, amino, hydroxy, ether, thio, thioether, $C_{1-7}$alkyl, $C_{1-7}$haloalkyl, acyl, amido, carboxy, cyano, and aminoalkyl.

45. A compound according to claim 43, wherein each R is independently a substituent selected from: —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

46. A compound according to claim 36, wherein K is a group of the formula:

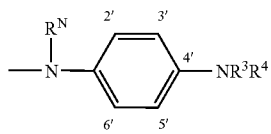

wherein $R^3$ and $R^4$ are independently hydrogen, $C_{1-7}$alkyl, $C_{3-20}$heterocyclyl, or $C_{5-20}$aryl, or $R^3$ and $R^4$, taken together with the nitrogen atom to which they are attached, form a heterocyclic ring having from 3 to 8 ring atoms.

47. A compound according to claim 36, wherein Q is a $C_{1-7}$alkyl group substituted with a $C_{5-6}$aryl group.

48. A compound according to claim 36, wherein Q is a $C_{1-7}$alkyl group substituted with an optionally substituted phenyl group.

49. A compound according to claim 36, wherein Q is a $C_{1-7}$alkyl group substituted with a substituted phenyl group.

50. A compound according to claim 36, wherein Q is a $C_{1-7}$alkyl group substituted with a phenyl group substituted with one or more groups selected from: —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

51. A compound according to claim 36, wherein Q is a $C_{1-7}$alkyl group substituted with an optionally substituted pyridyl group.

52. A compound according to claim 36, wherein Q is a $C_{1-7}$alkyl group substituted with an unsubstituted pyridyl group.

53. A compound according to claim 36, wherein Q is a methyl group substituted with a $C_{5-6}$aryl group.

54. A compound according to claim 36, wherein Q is a methyl group substituted with a substituted phenyl group.

55. A compound according to claim 36, wherein Q is a methyl group substituted with a phenyl group substituted with one or more groups selected from: —F, —Cl, —Br, —I, —OH, —OMe, —OEt, —SH, —SMe, —SEt, —C(=O)Me, —C(=O)OH, —C(=O)OMe, —CONH$_2$, —CONHMe, —NH$_2$, —NMe$_2$, —NEt$_2$, —N(nPr)$_2$, —N(iPr)$_2$, —CN, —NO$_2$, -Me, -Et, —CF$_3$, —OCF$_3$, —CH$_2$OH, —CH$_2$CH$_2$OH, —CH$_2$NH$_2$, —CH$_2$CH$_2$NH$_2$, and -Ph.

56. A compound according to claim 36, wherein Q is a methyl group substituted with an optionally substituted pyridyl group.

57. A compound according to claim 36, wherein Q is a methyl group substituted with an unsubstituted pyridyl group.

58. A composition comprising a compound according to claim 36 and a pharmaceutically acceptable carrier or diluent.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:

```
<223> OTHER INFORMATION: Forward primer

<400> SEQUENCE: 1
ggagttccgc gttacataac                                               20

<210> SEQ ID NO 2
<211> LENGTH: 20
<212> TYPE: DNA
<213> ORGANISM: Artificial Sequence
<220> FEATURE:
<223> OTHER INFORMATION: Reverse primer

<400> SEQUENCE: 2
gtctgctcga agcattaacc                                               20

<210> SEQ ID NO 3
<211> LENGTH: 18
<212> TYPE: DNA
<213> ORGANISM: Artificial Sequence
<220> FEATURE:
<223> OTHER INFORMATION: TS Forward primer

<400> SEQUENCE: 3
aatccgtcga gcagagtt                                                 18

<210> SEQ ID NO 4
<211> LENGTH: 24
<212> TYPE: DNA
<213> ORGANISM: Artificial Sequence
<220> FEATURE:
<223> OTHER INFORMATION: Reverse CX primer

<400> SEQUENCE: 4
aatcccattc ccattcccat tccc                                          24
```